US012630637B2

(12) United States Patent
Rainey et al.

(10) Patent No.: US 12,630,637 B2
(45) Date of Patent: \*May 19, 2026

(54) ANTIGEN-BINDING PROTEINS AND RELATED METHODS OF USE

(71) Applicant: Gritstone bio, Inc., Jackson, WY (US)

(72) Inventors: Godfrey Jonah Anderson Rainey, San Diego, CA (US); Karin Jooss, San Diego, CA (US); Roman Yelensky, Newton, MA (US); Wade Blair, Gaithersburg, MD (US); Heungnam Kim, Jackson, WY (US); Christine Janson, Jackson, WY (US); Anne Van Abbema, Jackson, WY (US); Isaac J. Rondon, Jackson, WY (US)

(73) Assignee: Gritstone bio, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/284,312

(22) Filed: Jul. 29, 2025

(65) Prior Publication Data

US 2025/0353914 A1     Nov. 20, 2025

Related U.S. Application Data

(63) Continuation of application No. 18/300,747, filed on Apr. 14, 2023, which is a continuation of application No. PCT/US2021/055261, filed on Oct. 15, 2021.

(60) Provisional application No. 63/092,457, filed on Oct. 15, 2020.

(51) Int. Cl.
*C07K 16/28*          (2006.01)

(52) U.S. Cl.
CPC ...... *C07K 16/2833* (2013.01); *C07K 16/2809* (2013.01); *C07K 2317/24* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/622* (2013.01)

(58) Field of Classification Search
CPC ....................... C07K 16/2833; C07K 16/2809
See application file for complete search history.

(56) References Cited

U.S. PATENT DOCUMENTS

| | | | |
|---|---|---|---|
| 3,843,638 A | 10/1974 | Nicki et al. |
| 4,452,773 A | 6/1984 | Molday |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,795,698 A | 1/1989 | Owen et al. |
| 4,816,567 A | 3/1989 | Cabilly et al. |
| 4,927,762 A | 5/1990 | Darfler |
| 4,946,778 A | 8/1990 | Ladner et al. |
| 5,122,469 A | 6/1992 | Mather et al. |
| 5,132,405 A | 7/1992 | Huston et al. |
| 5,200,084 A | 4/1993 | Liberti et al. |
| 5,204,244 A | 4/1993 | Fell et al. |
| 5,219,740 A | 6/1993 | Miller et al. |
| 5,229,275 A | 7/1993 | Goroff |
| 5,500,362 A | 3/1996 | Robinson et al. |
| 5,514,578 A | 5/1996 | Hogness et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,589,369 A | 12/1996 | Seidman et al. |
| 5,591,669 A | 1/1997 | Krimpenfort et al. |
| 5,624,821 A | 4/1997 | Winter et al. |
| 5,648,260 A | 7/1997 | Winter et al. |
| 5,662,907 A | 9/1997 | Kubo et al. |
| 5,693,761 A | 12/1997 | Queen et al. |
| 5,693,762 A | 12/1997 | Queen et al. |
| 5,731,168 A | 3/1998 | Carter et al. |
| 5,821,337 A | 10/1998 | Carter et al. |
| 5,849,589 A | 12/1998 | Tedder et al. |
| 6,040,177 A | 3/2000 | Riddell et al. |
| 6,171,586 B1 | 1/2001 | Lam et al. |
| 6,180,370 B1 | 1/2001 | Queen et al. |
| 6,194,551 B1 | 2/2001 | Idusogie et al. |

(Continued)

FOREIGN PATENT DOCUMENTS

| | | |
|---|---|---|
| EP | 0452342 A1 | 10/1991 |
| EP | 0453082 A1 | 10/1991 |

(Continued)

OTHER PUBLICATIONS

GSRS Substance J43DL56H6M; "Foralumab"; https://gsrs.ncats.nih.gov/ginas/app/ui/substances/J43DL56H6M (Year: 2025).*
DrugBank ID DB00075; "Muromonab"; https://go.drugbank.com/drugs/DB00075 (Year: 2005).*
Emanuel et al. "A fibronectin scaffold approach to bispecific inhibitors of epidermal growth factor receptor and insulin-like growth factor-I receptor." MAbs. vol. 3. No. 1. Taylor & Francis (2011): 38-48.
Eng et al. "A deeper look into Comet—implementation and features." Journal of the American Society for Mass Spectrometry 26.11 (2015): 1865-1874.

(Continued)

*Primary Examiner* — Julie Wu
*Assistant Examiner* — Bryan William Heck
(74) *Attorney, Agent, or Firm* — The Marbury Law Group, PLLC

(57)          ABSTRACT

Provided herein are antigen binding proteins (ABPs) that bind HLA-PEPTIDE targets. Also disclosed are methods for identifying the HLA-PEPTIDE targets and methods of treating cancers and other diseases using the disclosed ABPs.

27 Claims, 11 Drawing Sheets

Specification includes a Sequence Listing.

(56) References Cited

U.S. PATENT DOCUMENTS

| | | | |
|---|---|---|---|
| 6,207,453 B1 | 3/2001 | Maass et al. | |
| 6,245,531 B1 | 6/2001 | Hogness et al. | |
| 6,267,958 B1 | 7/2001 | Andya et al. | |
| 6,410,319 B1 | 6/2002 | Raubitschek et al. | |
| 6,451,995 B1 | 9/2002 | Cheung et al. | |
| 6,737,056 B1 | 5/2004 | Presta | |
| 7,070,995 B2 | 7/2006 | Jensen | |
| 7,091,038 B2 | 8/2006 | Palli et al. | |
| 7,129,330 B1 | 10/2006 | Little et al. | |
| 7,250,297 B1 | 7/2007 | Beste et al. | |
| 7,265,209 B2 | 9/2007 | Jensen | |
| 7,332,581 B2 | 2/2008 | Presta | |
| 7,354,762 B2 | 4/2008 | Jensen | |
| 7,371,826 B2 | 5/2008 | Presta | |
| 7,446,179 B2 | 11/2008 | Jensen et al. | |
| 7,446,190 B2 | 11/2008 | Sadelain et al. | |
| 7,446,191 B2 | 11/2008 | Jensen | |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,550,143 B2 | 6/2009 | Chang et al. | |
| 7,569,664 B2 | 8/2009 | Jakobsen et al. | |
| 7,585,940 B2 | 9/2009 | Skerra et al. | |
| 7,612,181 B2 | 11/2009 | Wu et al. | |
| 7,695,936 B2 | 4/2010 | Carter et al. | |
| 8,258,082 B2 | 9/2012 | Ladner | |
| 8,324,353 B2 | 12/2012 | Jensen | |
| 8,339,645 B2 | 12/2012 | Nakawaki | |
| 8,389,282 B2 | 3/2013 | Sadelain et al. | |
| 8,398,282 B2 | 3/2013 | Kuhlman et al. | |
| 8,479,118 B2 | 7/2013 | Lyndersay et al. | |
| 8,586,713 B2 | 11/2013 | Davis et al. | |
| 8,592,562 B2 | 11/2013 | Kannan et al. | |
| 8,592,563 B2 | 11/2013 | Bates et al. | |
| 8,691,730 B2 | 4/2014 | Vasquez et al. | |
| 8,858,931 B2 | 10/2014 | Langlade-Demoyen et al. | |
| 8,911,993 B2 | 12/2014 | June et al. | |
| 8,969,526 B2 | 3/2015 | Baehner et al. | |
| 9,150,641 B2 | 10/2015 | Kettenberger et al. | |
| 9,309,326 B2 | 4/2016 | Davis et al. | |
| 9,587,020 B2 | 3/2017 | Wu et al. | |
| 9,644,025 B2 | 5/2017 | Black et al. | |
| 9,683,052 B2 | 6/2017 | Blein et al. | |
| 9,809,958 B2 | 11/2017 | Shang et al. | |
| 9,822,186 B2 | 11/2017 | Bernett et al. | |
| 9,982,013 B2 | 5/2018 | Davis et al. | |
| 10,055,540 B2 | 8/2018 | Yelensky et al. | |
| 10,611,842 B2 | 4/2020 | Liu et al. | |
| 11,792,145 B2 | 10/2023 | Lapic et al. | |
| 2002/0131960 A1 | 9/2002 | Sadelain et al. | |
| 2003/0215914 A1 | 11/2003 | Houtzager et al. | |
| 2005/0014934 A1 | 1/2005 | Hinton et al. | |
| 2006/0122119 A1 | 6/2006 | Linard et al. | |
| 2007/0123479 A1 | 5/2007 | Kufer et al. | |
| 2007/0196369 A1 | 8/2007 | Hoogenboom et al. | |
| 2008/0069820 A1 | 3/2008 | Fuh et al. | |
| 2008/0206312 A1 | 8/2008 | Robertson et al. | |
| 2009/0215991 A1 | 8/2009 | Lazar et al. | |
| 2009/0253694 A1 | 10/2009 | Ono et al. | |
| 2010/0228007 A1 | 9/2010 | Hoogenboom et al. | |
| 2010/0316653 A1 | 12/2010 | Slifka et al. | |
| 2011/0003380 A1 | 1/2011 | Miltenyi et al. | |
| 2011/0014213 A1 | 1/2011 | Torikai et al. | |
| 2011/0091489 A1 | 4/2011 | Andersen | |
| 2011/0245209 A1 | 10/2011 | Xiao et al. | |
| 2012/0058906 A1 | 3/2012 | Smider et al. | |
| 2013/0149337 A1 | 6/2013 | Cooper et al. | |
| 2013/0287748 A1 | 10/2013 | June et al. | |
| 2013/0315935 A1 | 11/2013 | Schwabe | |
| 2015/0018530 A1 | 1/2015 | Miao et al. | |
| 2016/0024147 A1 | 1/2016 | Tustian et al. | |
| 2016/0152725 A1 | 6/2016 | Cheung et al. | |
| 2016/0176953 A1 | 6/2016 | Purcell et al. | |
| 2017/0166877 A1 | 6/2017 | Bayle et al. | |
| 2017/0199961 A1 | 7/2017 | Yelensky et al. | |
| 2017/0218078 A1 | 8/2017 | Raum et al. | |
| 2017/0292952 A1 | 10/2017 | Hantash | |
| 2018/0118827 A1 | 5/2018 | Moore et al. | |
| 2018/0142040 A1 | 5/2018 | Moore et al. | |
| 2018/0153975 A1 | 6/2018 | Fritsch et al. | |
| 2018/0179283 A1 | 6/2018 | Peled Kamar et al. | |
| 2018/0326002 A1 | 11/2018 | Powlesland et al. | |
| 2018/0330055 A1 | 11/2018 | Yelensky et al. | |
| 2019/0031713 A1 | 1/2019 | Davis et al. | |
| 2019/0034585 A1 | 1/2019 | Yelensky et al. | |
| 2019/0065675 A1 | 2/2019 | Yelensky et al. | |
| 2019/0135891 A1 | 5/2019 | Stevanovic et al. | |
| 2019/0279742 A1 | 9/2019 | Bulik-Sullivan et al. | |
| 2020/0390899 A1 | 12/2020 | Ackerman et al. | |
| 2021/0061914 A1 | 3/2021 | Jooss et al. | |
| 2021/0147550 A1 | 5/2021 | Jooss et al. | |
| 2021/0196806 A1 | 7/2021 | Yelensky et al. | |
| 2021/0213122 A1 | 7/2021 | Blair et al. | |
| 2022/0162320 A1 | 5/2022 | Jooss et al. | |
| 2022/0213196 A1 | 7/2022 | Jooss et al. | |
| 2023/0041030 A1 | 2/2023 | Jooss et al. | |
| 2023/0287128 A1 | 9/2023 | Rainey et al. | |
| 2023/0295305 A1* | 9/2023 | Rainey | C07K 16/18 424/133.1 |
| 2023/0382997 A1 | 11/2023 | Jooss et al. | |
| 2024/0059797 A1 | 2/2024 | Rainey et al. | |
| 2024/0279343 A1 | 8/2024 | Rondon et al. | |

FOREIGN PATENT DOCUMENTS

| | | | |
|---|---|---|---|
| EP | 0517805 B1 | 7/2002 | |
| EP | 2537416 A1 | 12/2012 | |
| EP | 1746107 B1 | 12/2014 | |
| EP | 2975051 A1 | 1/2016 | |
| WO | 8700185 A1 | 1/1987 | |
| WO | 8700195 A1 | 1/1987 | |
| WO | 9003430 A1 | 4/1990 | |
| WO | 9308829 A1 | 5/1993 | |
| WO | 9316185 A2 | 8/1993 | |
| WO | 9429351 A2 | 12/1994 | |
| WO | 9839482 A1 | 9/1998 | |
| WO | 9951642 A1 | 10/1999 | |
| WO | 9958572 A1 | 11/1999 | |
| WO | 0014257 A1 | 3/2000 | |
| WO | 0162908 A2 | 8/2001 | |
| WO | 2004044004 A2 | 5/2004 | |
| WO | 2005100402 A1 | 10/2005 | |
| WO | 2005116646 A1 | 12/2005 | |
| WO | 2006029879 A2 | 3/2006 | |
| WO | 2006044908 A2 | 4/2006 | |
| WO | 2006076594 A2 | 7/2006 | |
| WO | 2008118017 A2 | 10/2008 | |
| WO | 2008134046 A1 | 11/2008 | |
| WO | 2009051555 A2 | 4/2009 | |
| WO | 2009072003 A2 | 6/2009 | |
| WO | 2009089004 A1 | 7/2009 | |
| WO | 2010033140 A2 | 3/2010 | |
| WO | 2011143545 A1 | 11/2011 | |
| WO | 2012013913 A1 | 2/2012 | |
| WO | 2012129514 A1 | 9/2012 | |
| WO | 2013039889 A1 | 3/2013 | |
| WO | 2013041865 A1 | 3/2013 | |
| WO | 2013071154 A1 | 5/2013 | |
| WO | 2013123061 A1 | 8/2013 | |
| WO | 2013126726 A1 | 8/2013 | |
| WO | 2013151666 A2 | 10/2013 | |
| WO | 2013165690 A1 | 11/2013 | |
| WO | 2013166321 A1 | 11/2013 | |
| WO | 2014018863 A1 | 1/2014 | |
| WO | 2014031687 A1 | 2/2014 | |
| WO | 2014055668 A1 | 4/2014 | |
| WO | 2014138449 A1 | 9/2014 | |
| WO | 2014165818 A2 | 10/2014 | |
| WO | 2015103072 A1 | 7/2015 | |
| WO | 2015136072 A1 | 9/2015 | |
| WO | 2016069283 A1 | 5/2016 | |
| WO | 2016085904 A1 | 6/2016 | |
| WO | 2016154047 A2 | 9/2016 | |
| WO | 2016154246 A1 | 9/2016 | |

(56) References Cited

FOREIGN PATENT DOCUMENTS

| WO | 2016187508 | A2 | 11/2016 | |
| WO | 2016191246 | A2 | 12/2016 | |
| WO | 2016201124 | A2 | 12/2016 | |
| WO | 2017046198 | A1 | 3/2017 | |
| WO | 2017089756 | A1 | 6/2017 | |
| WO | 2017106638 | A1 | 6/2017 | |
| WO | 2017124001 | A2 | 7/2017 | |
| WO | 2017156178 | A1 | 9/2017 | |
| WO | 2017173321 | A1 | 10/2017 | |
| WO | 2017184590 | A1 | 10/2017 | |
| WO | 2017189254 | A1 | 11/2017 | |
| WO | 2017196432 | A1 | 11/2017 | |
| WO | 2018164637 | A1 | 9/2018 | |
| WO | 2018195357 | A1 | 10/2018 | |
| WO | 2018227030 | A1 | 12/2018 | |
| WO | 2019007974 | A1 | 1/2019 | |
| WO | 2019036688 | A1 | 2/2019 | |
| WO | 2019046316 | A1 | 3/2019 | |
| WO | 2019050994 | A1 | 3/2019 | |
| WO | 2019075112 | A1 | 4/2019 | |
| WO | 2019075392 | A1 | 4/2019 | |
| WO | WO-2019133853 | A1 * | 7/2019 | ......... C07K 16/2833 |
| WO | 2019168984 | A1 | 9/2019 | |
| WO | 2020037302 | A1 | 2/2020 | |
| WO | 2020160189 | A1 | 8/2020 | |
| WO | WO-2020236792 | A1 * | 11/2020 | ....... C07K 14/70528 |
| WO | 2021092094 | A1 | 5/2021 | |
| WO | 2021168355 | A1 | 8/2021 | |
| WO | 2022026772 | A1 | 2/2022 | |
| WO | 2022082030 | A2 | 4/2022 | |
| WO | 2022155503 | A1 | 7/2022 | |

OTHER PUBLICATIONS

Extended European Search Report in EP20748612.7, mailed Feb. 7, 2023, 12 pages.

Extended European Search Report in EP21756615.7, mailed Feb. 19, 2024, 6 pages.

Extended European Search Report in EP21850618.6, mailed Nov. 29, 2024, 12 pages.

Extended European Search Report in EP21881209.7, mailed Nov. 8, 2024, 7 pages.

Extended European Search Report in EP22740170.0, mailed May 12, 2025, 9 pages.

Fedorov et al. "PD-1- and CTLA-4-based inhibitory chimeric antigen receptors (iCARs) divert off-target immunotherapy responses." Science translational medicine 5.215 (2013): 215ra172-215ra172.

Fernandez, L. "Prokaryotic expression of antibodies and affibodies." Current opinion in biotechnology 15.4 (2004): 364-373.

Fitzgerald et al. "Improved tumour targeting by disulphide stabilized diabodies expressed in Pichia pastoris." Protein engineering vol. 10. No. 10 (1997): 1221-1225.

Frattini et al. "The integrated landscape of driver genomic alterations in glioblastoma." Nature genetics 45.10 (2013): 1141-1149.

Fukuyama et al. "Expression of KK-LC-1, a cancer/testis antigen, at non-tumour sites of the stomach carrying a tumour." Scientific reports 8.1 (2018): 6131.

Fukuyama et al. "Identification of a new cancer/germline gene, KK-LC-1, encoding an antigen recognized by autologous CTL induced on human lung adenocarcinoma." Cancer research 66.9 (2006): 4922-4928.

Futawatari et al. "Early gastric cancer frequently has high expression of KK-LC-1, a cancer-testis antigen." World Journal of Gastroenterology 23.46 (2017): 8200.

Garboczi et al. "HLA-A2-peptide complexes: refolding and crystallization of molecules expressed in *Escherichia coli* and complexed with single antigenic peptides." Proceedings of the National Academy of Sciences 89.8 (1992): 3429-3433.

Gazzano-Santoro et al. "A non-radioactive complement-dependent cytotoxicity assay for anti-CD20 monoclonal antibody." Journal of immunological methods 202.2 (1997): 163-171.

Geyer et al. "[13] Selection of genetic agents from random peptide aptamer expression libraries." Methods in enzymology. vol. 328. Academic Press, 2000. 171-208.

Godin et al. "Microfluidics and photonics for Bio-System-on-a-Chip: A review of advancements in technology towards a microfluidic flow cytometry chip." Journal of biophotonics 1.5 (2008): 355-376 GSO-001C2.

Goding, J.W., Monoclonal Antibodies: Principles and Practice 3rd ed. (1986) Academic Press, San Diego, CA.

Govers et al. "T cell receptor fused to CD3ζ: transmembrane domain of CD3ζ prevents TCR mis-pairing, whereas complete CD3ζ directs functional TCR expression." The Open Gene Therapy Journal 4.1 (2011): 11-22.

Gramer et al. "Production of stable bispecific IgG1 by controlled Fab-arm exchange: scalability from bench to large-scale manufacturing by application of standard approaches." MAbs. vol. 5. No. 6. Taylor & Francis (2013): 962-972.

Graversen et al. "Mutational Analysis of Affinity and Selectivity of Kringle-Tetranectin Interaction: Grafting Novel Kringle Affinity Onto The Tetranectin Lectin Scaffold." Journal of Biological Chemistry 275.48 (2000): 37390-37396.

Griffioen et al. "Retroviral transfer of human CD20 as a suicide gene for adoptive T-cell therapy." haematologica 94.9 (2009): 1316-1320.

Grotenbreg et al. "Discovery of CD8+ T cell epitopes in Chlamydia trachomatis infection through use of caged class I MHC tetramers." Proceedings of the National Academy of Sciences 105.10 (2008): 3831-3836.

Gruber et al. "Efficient tumor cell lysis mediated by a bispecific single chain antibody expressed in *Escherichia coli*." The journal of immunology 152.11 (1994): 5368-5374.

Gunasekaran et al. "Enhancing antibody Fc heterodimer formation through electrostatic steering effects: applications to bispecific molecules and monovalent IgG." Journal of Biological Chemistry 285.25 (2010): 19637-19646.

Haga-Friedman et al. "Incorporation of transmembrane hydrophobic mutations in the TCR enhance its surface expression and T cell functional avidity." The Journal of Immunology 188.11 (2012): 5538-5546.

Hegde et al. "The surprising complexity of signal sequences." Trends in biochemical sciences 31.10 (2006): 563-571.

Hellstrom et al. "Antitumor effects of L6, an IgG2a antibody that reacts with most human carcinomas." Proceedings of the National Academy of Sciences 83.18 (1986): 7059-7063.

Hellstrom et al. "Strong antitumor activities of IgG3 antibodies to a human melanoma-associated ganglioside." Proceedings of the National Academy of Sciences 82.5 (1985): 1499-1502.

Hinton et al. "An engineered human IgG1 antibody with longer serum half-life." The Journal of Immunology 176.1 (2006): 346-356.

Hippisley-Cox et al. "Development and validation of risk prediction equations to estimate future risk of heart failure in patients with diabetes: a prospective cohort study." BMJ open 5.9 (2015): 1-25.

Holland et al. "Specificity of bispecific T cell receptors and antibodies targeting peptide-HLA." The Journal of clinical investigation 130.5 (2020): 2673-2688.

Holliger et al. ""Diabodies": small bivalent and bispecific antibody fragments." Proceedings of the National Academy of Sciences 90.14 (1993): 6444-6448.

Hsu et al. "Cytokine-independent growth and clonal expansion of a primary human CD8+ T-cell clone following retroviral transduction with the IL-15 gene." Blood, The Journal of the American Society of Hematology 109.12 (2007): 5168-5177 GSO-001C2.

Hsu et al. "Primary human T lymphocytes engineered with a codon-optimized IL-15 gene resist cytokine withdrawal-induced apoptosis and persist long-term in the absence of exogenous cytokine." The Journal of Immunology 175.11 (2005): 7226-7234.

Huang et al. "DNA transposons for modification of human primary T lymphocytes." Methods Mol Biol 506 (2009): 115-126.

Huang et al. "Systematic and integrative analysis of large gene lists using DAVID bioinformatics resources." Nature protocols 4.1 (2009): 44-57.

(56) References Cited

OTHER PUBLICATIONS

Hudecek et al. "Receptor affinity and extracellular domain modifications affect tumor recognition by ROR1-specific chimeric antigen receptor T cells." Clinical cancer research 19.12 (2013): 3153-3164.

Hudson et al. "Engineered antibodies." Nature medicine 9.1 (2003): 129-134.

International Preliminary Report on Patentability in PCT/US2018/046997, mailed Feb. 20, 2020, 11 pages.

International Preliminary Report on Patentability in PCT/US2018/067931, mailed Jul. 9, 2020, 14 pages.

International Preliminary Report on Patentability in PCT/US2019/046967, mailed Jan. 21, 2020, 9 pages.

International Preliminary Report on Patentability in PCT/US2020/015736, mailed Aug. 12, 2021, 18 pages.

International Preliminary Report on Patentability in PCT/US2021/018912, mailed Sep. 1, 2022, 9 pages.

International Preliminary Report on Patentability in PCT/US2021/043796, mailed Feb. 9, 2023, 14 pages.

International Preliminary Report on Patentability in PCT/US2021/055261, mailed Apr. 27, 2023, 12 pages.

International Preliminary Report on Patentability in PCT/US2022/012573, mailed Jul. 27, 2023, 9 pages.

International Search Report and Written Opinion in PCT/US2018/046997, mailed Dec. 20, 2018, 22 pages.

International Search Report and Written Opinion in PCT/US2018/067931, mailed Apr. 30, 2019, 22 pages.

International Search Report and Written Opinion in PCT/US2019/046967, mailed Jan. 21, 2020, 13 pages.

International Search Report and Written Opinion in PCT/US2020/015736, mailed Jul. 1, 2020, 18 pages.

International Search Report and Written Opinion in PCT/US2020/058982, mailed Mar. 26, 2021, 15 pages.

International Search Report and Written Opinion in PCT/US2021/018912, mailed May 21, 2021, 9 pages.

International Search Report and Written Opinion in PCT/US2021/043796, mailed Dec. 29, 2021, 14 pages.

International Search Report and Written Opinion in PCT/US2021/055261, mailed Apr. 5, 2022, 18 pages.

International Search Report and Written Opinion in PCT/US2022/012573, mailed May 13, 2022, 11 pages.

Invitation to Pay Additional Fees in PCT/US2019/046967, mailed Nov. 27, 2019, 2 pages.

Jin et al. "Establishment of cancer/testis antigen profiling based on clinicopathological characteristics in resected pathological stage III non-small cell lung cancer." Cancer management and research (2018): 2031-2046.

Kerry et al. "Interplay between TCR affinity and necessity of coreceptor ligation: high-affinity peptide-MHC/TCR interaction overcomes lack of CD8 engagement." The Journal of Immunology 171.9 (2003): 4493-4503.

Kessels et al. "Changing T cell specificity by retroviral T cell receptor display." Proceedings of the National Academy of Sciences 97.26 (2000): 14578-14583.

Kipriyanov et al. "Bispecific tandem diabody for tumor therapy with improved antigen binding and pharmacokinetics." Journal of molecular biology 293.1 (1999): 41-56.

Klebanoff et al. "Sorting through subsets: which T-cell populations mediate highly effective adoptive immunotherapy?." Journal of immunotherapy 35.9 (2012): 651-660.

Kohler et al. "Continuous cultures of fused cells secreting antibody of predefined specificity." nature 256.5517 (1975): 495-497.

Koste et al. "T-cell receptor transfer into human T cells with ecotropic retroviral vectors." Gene therapy 21.5 (2014): 533-538.

Kuball et al. "Facilitating matched pairing and expression of TCR chains introduced into human T cells." Blood 109.6 (2007): 2331-2338.

Kuball et al. "Increasing functional avidity of TCR-redirected T cells by removing defined N-glycosylation sites in the TCR constant domain." Journal of Experimental Medicine 206.2 (2009): 463-475.

Labrijn et al. "Efficient generation of stable bispecific IgG1 by controlled Fab-arm exchange." Proceedings of the National Academy of Sciences 110.13 (2013): 5145-5150.

Lafleur et al. "Monoclonal antibody therapeutics with up to five specificities: functional enhancement through fusion of target-specific peptides." MAbs. vol. 5. No. 2. Taylor & Francis (2013): 208-218.

Lazar et al. "Engineered antibody Fc variants with enhanced effector function." Proceedings of the National Academy of Sciences 103.11 (2006): 4005-4010.

Lefranc at al. "Human Gm, Km, and Am allotypes and their molecular characterization: a remarkable demonstration of polymorphism." Immunogenetics: Methods and Applications in Clinical Practice. Totowa, NJ: Humana Press, 2012. 635-680.

Legut et al. "CRISPR-mediated TCR replacement generates superior anticancer transgenic T cells." Blood, The Journal of the American Society of Hematology 131.3 (2018): 311-322.

Li et al. "Increasing the safety and efficacy of chimeric antigen receptor T cell therapy." Protein & cell 8.8 (2017): 573-589.

Li et al. "RSEM: accurate transcript quantification from RNA-Seq data with or without a reference genome." BMC bioinformatics 12.1 (2011): 323.

Lloyd et al. "Modelling the human immune response: performance of a 1011 human antibody repertoire against a broad panel of therapeutically relevant antigens." Protein Engineering, Design & Selection 22.3 (2009): 159-168.

Lonsdale et al. "The genotype-tissue expression (GTEx) project." Nature genetics 45.6 (2013): 580-585.

Luimstra et al. "A flexible MHC class I multimer loading system for large-scale detection of antigen-specific T cells." Journal of Experimental Medicine 215.5 (2018): 1493-1504.

Lupton et al. "Dominant positive and negative selection using a hygromycin phosphotransferase-thymidine kinase fusion gene." Molecular and Cellular Biology 11.6 (1991): 3374-3378.

Manuri et al. "piggyBac transposon/transposase system to generate CD19-specific T cells for the treatment of B-lineage malignancies." Human gene therapy 21.4 (2010): 427-437.

Marcinkowski et al. "Cancer targeting by TCR gene-engineered T cells directed against Kita-Kyushu Lung Cancer Antigen-1." Journal for immunotherapy of cancer 7.1 (2019): 229.

Marks et al. "By-passing immunization: human antibodies from V-gene libraries displayed on phage." Journal of molecular biology 222.3 (1991): 581-597.

McKinney, P. "Brain tumours: incidence, survival, and aetiology." Journal of Neurology, Neurosurgery & Psychiatry 75.suppl 2 (2004): ii12-ii17.

Merchant et al. "An efficient route to human bispecific IgG." Nature biotechnology 16.7 (1998): 677-681.

Meyer et al. "New insights in Type I and II CD 20 antibody mechanisms-of-action with a panel of novel CD 20 antibodies." British Journal of Haematology 180.6 (2018): 808-820.

Moon et al. "Expression of a functional CCR2 receptor enhances tumor localization and tumor eradication by retargeted human T cells expressing a mesothelin-specific chimeric antibody receptor." Clinical cancer research 17.14 (2011): 4719-4730.

Moore et al. "A novel bispecific antibody format enables simultaneous bivalent and monovalent co-engagement of distinct target antigens." MAbs. vol. 3. No. 6. Taylor & Francis (2011): 546-557.

Moore et al. "Application of dual affinity retargeting molecules to achieve optimal redirected T-cell killing of B-cell lymphoma." Blood, The Journal of the American Society of Hematology 117.17 (2011): 4542-4551.

Moretti et al. "BEAT® the bispecific challenge: a novel and efficient platform for the expression of bispecific IgGs." BMC Proceedings. vol. 7. No. Suppl 6. London: BioMed Central, 2013.

Morrison et al. "Chimeric human antibody molecules: mouse antigen-binding domains with human constant region domains." Proceedings of the National Academy of Sciences 81.21 (1984): 6851-6855.

Mosaad, Y. "Clinical role of human leukocyte antigen in health and disease." Scandinavian journal of immunology 82.4 (2015): 283-306.

(56)                References Cited

OTHER PUBLICATIONS

Mullen et al. "Transfer of the bacterial gene for cytosine deaminase to mammalian cells confers lethal sensitivity to 5-fluorocytosine: a negative selection system." Proceedings of the National Academy of Sciences 89.1 (1992): 33-37.

Murphy et al. (2017). Janeway's Immunobiology (9th ed.). Ch. 4 on pp. 139-172. New York: Garland Science.

Nih, "New T-Cell Immunotherapy that targets Aggressive Epithelial Tumors," National Institutes of Health, 2017 [retrieved on Apr. 28, 2020]. Retrieved from the Internet: <https://www.ott.nih.gov/ technology/e-153-2016/>, 2 pages.

Ochi et al. "Novel adoptive T-cell immunotherapy using a WT1-specific TCR vector encoding silencers for endogenous TCRs shows marked antileukemia reactivity and safety." Blood, The Journal of the American Society of Hematology 118.6 (2011): 1495-1503.

Office Action in CN201980060989.6, mailed Apr. 29, 2024, 7 pages.

Office Action in CN201980060989.6, mailed Jan. 11, 2025, 2 pages.

Office Action in CN201980060989.6, mailed Aug. 13, 2025, 6 pages.

Office Action in EP19849564.0, mailed Apr. 7, 2022, 3 pages.

Office Action in EP20748612.7, mailed Sep. 27, 2022, 4 pages.

Office Action in EP20748612.7, mailed Feb. 24, 2023, 1 page.

Office Action in EP21756615.7, mailed Mar. 7, 2024, 1 page.

Office Action in EP21850618.6, mailed Jul. 30, 2024, 4 pages.

Office Action in EP21850618.6, mailed Dec. 17, 2024, 1 page.

Office Action in EP22740170.0, mailed May 30, 2025, 1 page.

Office Action in IL280890, mailed Jan. 14, 2025, 3 pages.

Office Action in IL320680, mailed May 13, 2025, 3 pages.

Office Action in U.S. Appl. No. 17/269,246, mailed Mar. 7, 2025, 119 pages.

Oganesyan et al. "Structural characterization of a human Fc fragment engineered for lack of effector functions." Biological Crystallography 64.6 (2008): 700-704.

Okamoto et al. "A promising vector for TCR gene therapy: differential effect of siRNA, 2A peptide, and disulfide bond on the introduced TCR expression." Molecular therapy Nucleic acids 1 (2012).

Olsen et al. "TANTIGEN: a comprehensive database of tumor T cell antigens." Cancer Immunology, Immunotherapy 66.6 (2017): 731-735.

Oxford, "Treating," Oxford English Dictionary, 2025, [retrieved on Feb. 24, 2025]. Retrieved from the Internet: <URL: https://www. oed.com/dictionary/treat>, 1 page.

Paret et al. "CXorf61 is a target for T cell based immunotherapy of triple-negative breast cancer." Oncotarget 6.28 (2015): 25356-25367.

Park et al. "Treating cancer with genetically engineered T cells." Trends in biotechnology 29.11 (2011): 550-557.

Paul, W. Fundamental Immunology. "(textbook),"Fv Structure and Diversity in Three Dimensions" pp. 292-295." (1993).

PCT/US2020/015736, filed Jan. 29, 2020, 534 pages.

Petkova et al. "Enhanced half-life of genetically engineered human IgG1 antibodies in a humanized FcRn mouse model: potential application in humorally mediated autoimmune disease." International immunology 18.12 (2006): 1759-1769.

Pino et al. "The Skyline Ecosystem: Informatics for Quantitative Mass Spectrometry Proteomics," HHS Public Access, Author Manuscript, Mass Spectrom Rev. (2019): 1-32.

Pluckthun et al. "New protein engineering approaches to multivalent and bispecific antibody fragments." Immunotechnology 3.2 (1997): 83-105.

Pluckthun, A. "Antibodies from Escherichia coli." The Pharmacology of Monoclonal Antibodies. Berlin, Heidelberg: Springer Berlin Heidelberg, 1994. 269-315.

Queen et al. "A humanized antibody that binds to the interleukin 2 receptor." Proceedings of the National Academy of Sciences 86.24 (1989): 10029-10033.

Quintarelli et al. "Co-expression of cytokine and suicide genes to enhance the activity and safety of tumor-specific cytotoxic T lymphocytes." Blood, The Journal of the American Society of Hematology 110.8 (2007): 2793-2802.

Rader et al. "A phage display approach for rapid antibody humanization: designed combinatorial V gene libraries." Proceedings of the National Academy of Sciences 95.15 (1998): 8910-8915.

Ravetch et al. "Fc receptors." Annual review of immunology 9 (1991): 457-492.

Riddell et al. "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington." Human gene therapy 3.3 (1992): 319-338.

Ridgway et al. "'Knobs-into-holes' engineering of antibody CH3 domains for heavy chain heterodimerization." Protein Engineering, Design and Selection 9.7 (1996): 617-621.

Rodenko et al. "Class I major histocompatibility complexes loaded by a periodate trigger." Journal of the American Chemical Society 131.34 (2009): 12305-12313.

Roth et al. "Reprogramming human T cell function and specificity with non-viral genome targeting." Nature 559.7714 (2018): 405-409.

Rothe et al. "Anticalin® proteins as therapeutic agents in human diseases." BioDrugs 32.3 (2018): 233-243.

Rothenberg et al. "Improving the evaluation of new cancer treatments: challenges and opportunities." Nature Reviews Cancer 3.4 (2003): 303-309.

Rudikoff et al. "Single amino acid substitution altering antigen-binding specificity." Proceedings of the National Academy of Sciences 79.6 (1982): 1979-1983.

Sadelain et al. "The basic principles of chimeric antigen receptor design." Cancer discovery 3.4 (2013): 388-398.

Saini et al. "Dipeptides catalyze rapid peptide exchange on MHC class I molecules." Proceedings of the National Academy of Sciences 112.1 (2015): 202-207.

Saini et al. "Dipeptides promote folding and peptide binding of MHC class I molecules." Proceedings of the National Academy of Sciences 110.38 (2013): 15383-15388.

Sebestyen et al. "Human TCR that incorporate CD3ζ induce highly preferred pairing between TCRα and β chains following gene transfer." The Journal of Immunology 180.11 (2008): 7736-7746.

Shapiro et al. "Single-cell sequencing-based technologies will revolutionize whole-organism science." Nature Reviews Genetics 14.9 (2013): 618-630.

Sharma et al. "Efficient sleeping beauty DNA transposition from DNA minicircles." Molecular therapy Nucleic acids 2 (2013).

Silacci et al. "Linker length matters, fynomer-Fc fusion with an optimized linker displaying picomolar IL-17A inhibition potency." Journal of Biological Chemistry 289.20 (2014): 14392-14398.

Silverman et al. "Multivalent avimer proteins evolved by exon shuffling of a family of human receptor domains." Nature biotechnology 23.12 (2005): 1556-1561.

Smith et al. "A novel, native-format bispecific antibody triggering T-cell killing of B-cells is robustly active in mouse tumor models and cynomolgus monkeys." Scientific reports 5.1 (2015): 17943.

Staerz et al. "Hybrid antibodies can target sites for attack by T cells." Nature 314.6012 (1985): 628-631.

Steinberger et al. "Generation and characterization of a recombinant human CCR5-specific antibody: A phage display approach for rabbit antibody humanization." Journal of Biological Chemistry 275.46 (2000): 36073-36078.

Stevanovic et al. "Landscape of immunogenic tumor antigens in successful immunotherapy of virally induced epithelial cancer." Science 356.6334 (2017): 200-205.

Stewart et al. "The role of Fc gamma receptors in the activity of immunomodulatory antibodies for cancer." Journal for ImmunoTherapy of Cancer 2.1 (2014): 29.

Strop et al. "Generating bispecific human IgG1 and IgG2 antibodies from any antibody pair." Journal of molecular biology 420.3 (2012): 204-219.

Terakura et al. "Generation of CD19-chimeric antigen receptor modified CD8+ T cells derived from virus-specific central memory T cells." Blood, The Journal of the American Society of Hematology 119.1 (2012): 72-82.

(56)                    References Cited

OTHER PUBLICATIONS

Thirdborough et al. "Vaccination with DNA encoding a single-chain TCR fusion protein induces anticlonotypic immunity and protects against T-cell lymphoma." Cancer research 62.6 (2002): 1757-1760.

Thompson et al. "Preventing the spontaneous modification of an HLA-A2-restricted peptide at an N-terminal glutamine or an internal cysteine residue enhances peptide antigenicity." Journal of Immunotherapy 27.3 (2004): 177-183.

Todorovska et al. "Design and application of diabodies, triabodies and tetrabodies for cancer targeting." Journal of immunological methods 248.1-2 (2001): 47-66.

Torikai et al. "A foundation for universal T-cell based immunotherapy: T cells engineered to express a CD19-specific chimeric-antigen-receptor and eliminate expression of endogenous TCR." Blood, The Journal of the American Society of Hematology 119.24 (2012): 5697-5705.

Torikai et al. "HLA and TCR Knockout by Zinc Finger Nucleases: Toward "off-the-Shelf" Allogeneic T-Cell Therapy for CD19+ Malignancies." Blood 116.21 (2010): 3766.

Traunecker et al. "Bispecific single chain molecules (Janusins) target cytotoxic lymphocytes on HIV infected cells." The EMBO Journal 10.12 (1991): 3655-3659.

Turtle et al. "Engineered T cells for anti-cancer therapy." Current opinion in immunology 24.5 (2012): 633-639.

Tutt et al. "Trispecific F (ab') 3 derivatives that use cooperative signaling via the TCR/CD3 complex and CD2 to activate and redirect resting cytotoxic T cells." Journal of immunology (Baltimore, Md.: 1950) 147.1 (1991): 60-69.

U.S. Appl. No. 17/426,627, filed Sep. 16, 2022, 404 pages.

U.S. Appl. No. 17/820,434, filed Aug. 17, 2022, 120 pages.

U.S. Appl. No. 18/018,400, filed Jul. 27, 2023, 374 pages.

Liu et al., "A Molecular Basis for the Interplay between T Cells, Viral Mutants, and Human Leukocyte Antigen Micropolymorphism," The Journal of Biologcal Chemistry, vol. 289, No. 24, pp. 16688-15598, Jun. 13, 2014.

U.S. Appl. No. 18/351,184, filed Jul. 12, 2023, 163 pages.

U.S. Appl. No. 19/284,186, filed Jul. 29, 2025, 325 pages.

Vajdos et al. "Comprehensive functional maps of the antigen-binding site of an anti-ErbB2 antibody obtained with shotgun scanning mutagenesis." Journal of molecular biology 320.2 (2002): 415-428.

Van Tendeloo et al. "High-level transgene expression in primary human T lymphocytes and adult bone marrow CD34+ cells via electroporation-mediated gene delivery." Gene therapy 7.16 (2000): 1431-1437.

Verhoeyen et al. "Lentiviral vector gene transfer into human T cells." Genetic modification of hematopoietic stem cells: methods and protocols. Totowa, NJ: Humana Press, 2009. 97-114.

Vita et al. "The immune epitope database (IEDB) 3.0." Nucleic acids research 43.D1 (2015): D405-D412.

Von Kreudensnein et al. "Improving biophysical properties of a bispecific antibody scaffold to aid developability: quality by molecular design." mAbs. vol. 5. No. 5. Taylor & Francis (2013): 646-54.

Wang et al. "Identification of T-cell receptors targeting KRAS-mutated human tumors." Cancer immunology research 4.3 (2016): 204-214.

Wang et al. "Immune targets and neoantigens for cancer immunotherapy and precision medicine." Cell research 27.1 (2017): 11-37.

Wang et al. "Phenotypic and functional attributes of lentivirus-modified CD19-specific human CD8+ central memory T cells manufactured at clinical scale." Journal of immunotherapy 35.9 (2012): 689-701.

Wieczorek et al. "Major histocompatibility complex (MHC) class I and MHC class II proteins: conformational plasticity in antigen presentation." Frontiers in immunology 8 (2017): 292.

Wigler et al. "Transfer of purified herpes virus thymidine kinase gene to cultured mouse cells." Cell 11.1 (1977): 223-232.

Willemsen et al. "Grafting primary human T lymphocytes with cancer-specific chimeric single chain and two chain TCR." Gene therapy 7.16 (2000): 1369-1377.

Willemsen et al. "Selection of human antibody fragments directed against tumor T-cell epitopes for adoptive T-cell therapy." Cytometry Part A 73.11 (2008): 1093-1099.

Wines et al. "The IgG Fc contains distinct Fc receptor (FcR) binding sites: the leukocyte receptors FcγRI and FcγRIIa bind to a region in the Fc distinct from that recognized by neonatal FcR and protein A." The Journal of Immunology 164.10 (2000): 5313-5318.

Winter et al. "Man-made antibodies." Nature 349.6307 (1991): 293-299.

Wong et al. "Novel antibody-like single-chain TCR antibody Fc fusion protein." The Journal of Immunology 198. Supplement_1 (2017): 120-9.

Wozniak-Knopp et al. "Introducing antigen-binding sites in structural loops of immunoglobulin constant domains: Fc fragments with engineered HER2/neu-binding sites and antibody properties." Protein Engineering, Design & Selection 23.4 (2010): 289-297.

Wu et al. "Adoptive T-cell therapy using autologous tumor-infiltrating lymphocytes for metastatic melanoma: current status and future outlook." The Cancer Journal 18.2 (2012): 160-175.

Wu et al. "Fab-based bispecific antibody formats with robust biophysical properties and biological activity." mAbs. vol. 7. No. 3. Taylor & Francis, 2015, 14 pages.

Wu et al. "Remote control of therapeutic T cells through a small molecule-gated chimeric receptor." Science 350.6258 (2015): aab4077.

Yin et al. "Aglycosylated antibodies and antibody fragments produced in a scalable in vitro transcription-translation system." mAbs. vol. 4. No. 2. Taylor & Francis (2012): 217-225.

Zahnd et al. "A designed ankyrin repeat protein evolved to picomolar affinity to Her2." Journal of molecular biology 369.4 (2007): 1015-1028.

Zarling et al. "Identification of class I MHC-associated phosphopeptides as targets for cancer immunotherapy." Proceedings of the National Academy of Sciences 103.40 (2006): 14889-14894.

Zhang et al. "Transgenic TCR expression: comparison of single chain with full-length receptor constructs for T-cell function." Cancer gene therapy 11.7 (2004): 487-496.

Zhukovsky et al. "A phase I study of an anti-CD30 x Anti-CD16A bispecific Tandab antibody, AFM13, in patients with relapsed or refractory Hodgkin lymphoma." Blood 122.21 (2013): 5116.

Mertens, N. "Tribodies: fab-scfv fusion proteins as a platform to create multifunctional pharmaceuticals." Bispecific antibodies. Berlin, Heidelberg: Springer Berlin Heidelberg, 2011. 135-149.

Office Action in U.S. Appl. No. 17/426,627, mailed Sep. 16, 2025, 71 pages.

Weatherill et al. "Towards a universal disulphide stabilised single chain Fv format: importance of interchain disulphide bond location and vL—vH orientation." Protein Engineering, Design & Selection 25.7 (2012): 321-329.

An et al. "IgG2m4, an engineered antibody isotype with reduced Fc function." MAbs. vol. 1. No. 6. Taylor & Francis, 2009, 572-579.

Carlring et al. "A novel redox method for rapid production of functional bi-specific antibodies for use in early pilot studies." PLoS One 6.7 (2011): 1-8.

Muyldermans et al. "Recognition of antigens by single-domain antibody fragments: the superfluous luxury of paired domains." Trends in biochemical sciences 26.4 (2001): 230-235.

First Examination Report received from the EP Patent Office in European Application No. EP 20748612.7 dated Oct. 28, 2025.

Galluzzi, et al., "Trial Watch: Monoclonal antibodies in cancer therapy", OncoImmunology 1(1): 23-37, (2012).

GenCore version 6.5.2, Copyright © 1993-2025; Biocceleration Ltd., citation Sequence 248, Publication No. US20220213194A1 (Year: 2020).

GenCore version 6.5.2, Copyright © 1993-2025; Biocceleration Ltd., citation BGN95135; Sequence 124, Publication No. WO2019133851A1 (Year: 2019).

Kabat, "Sequences of Proteins of Immunological Interest", vol. 1, 5th Edition, pp. 670-699 (1991).

Lazar et al., Engineered antibody Fc variants with enhanced effector function, Proc. Natl. Acad. Sci. USA., 2006, 103:4005-4010.

(56)         References Cited

OTHER PUBLICATIONS

Robbie, et al., "A Novel Investigational Fc-Modified Humanized Monoclonal Antibody, Motavizumab-YTE, Has an Extended Half-Life in Healthy Adults", Antimicrobial Agents Chemother. vol. 57, No. 12, pp. 6147-6153 (2013).

Non-Final Office Action for copending U.S. Appl. No. 18/300,747, dated Nov. 19, 2025, 14 pages.

U.S. Appl. No. 17/269,246, filed Feb. 17, 2021, 256 pages.

Final Office Action for copending U.S. Appl. No. 17/269,246, dated Nov. 20, 2025.

Aalberse et al. "IgG4 breaking the rules." Immunology 105.1 (2002): 9-19.

Abelin et al. "Complementary IMAC enrichment methods for HLA-associated phosphopeptide identification by mass spectrometry." Nature protocols 10.9 (2015): 1308-1318.

Ahmed et al. "TCR-mimic bispecific antibodies targeting LMP2A show potent activity against EBV malignancies." JCI insight 3.4 (2018): e97805.

Alonso-Camino et al. "CARbodies: human antibodies against cell surface tumor antigens selected from repertoires displayed on T cell chimeric antigen receptors." Molecular Therapy Nucleic Acids 2 (2013).

Amore et al. "Development of a hypersensitive periodate-cleavable amino acid that is methionine-and disulfide-compatible and its application in MHC exchange reagents for T cell characterisation." Chembiochem 14.1 (2013): 123-131.

An et al. "Construction of a new anti-CD19 chimeric antigen receptor and the anti-leukemia function study of the transduced T cells." Oncotarget 7.9 (2016): 10638.

Armour et al. "Differential binding to human FcγRIIa and FcγRIIb receptors by human IgG wildtype and mutant antibodies." Molecular immunology 40.9 (2003): 585-593.

Armour et al. "Recombinant human IgG molecules lacking Fcγ receptor I binding and monocyte triggering activities." European journal of immunology 29.8 (1999): 2613-2624.

Atwell et al. "Stable heterodimers from remodeling the domain interface of a homodimer using a phage display library." Journal of molecular biology 270.1 (1997): 26-35.

Bakker et al. "Conditional MHC class I ligands and peptide exchange technology for the human MHC gene products HLA-A1,-A3,-A11, and-B7." Proceedings of the National Academy of Sciences 105.10 (2008): 3825-3830.

Bassani-Sternberg et al. "Mass spectrometry of human leukocyte antigen class I peptidomes reveals strong effects of protein abundance and turnover on antigen presentation[S]." Molecular & Cellular Proteomics 14.3 (2015): 658-673.

Benlalam et al. "Identification of five new HLA-B 3501-restricted epitopes derived from common melanoma-associated antigens, spontaneously recognized by tumor-infiltrating lymphocytes." The Journal of Immunology 171.11 (2003): 6283-6289.

Bialer et al. "Selected murine residues endow human TCR with enhanced tumor recognition." The Journal of Immunology 184.11 (2010): 6232-6241.

Binz et al. "Engineering novel binding proteins from nonimmunoglobulin domains." Nature biotechnology 23.10 (2005): 1257-1268.

Borrok et al. "An "Fc-Silenced" IgG1 format with extended half-life designed for improved stability." Journal of Pharmaceutical Sciences 106.4 (2017): 1008-1017.

Brash et al. "Strontium phosphate transfection of human cells in primary culture: stable expression of the simian virus 40 large-T-antigen gene in primary human bronchial epithelial cells." Molecular and cellular biology 7.5 (1987): 2031-2034.

Bruggemann et al. "Comparison of the effector functions of human immunoglobulins using a matched set of chimeric antibodies." The Journal of experimental medicine 166.5 (1987): 1351-1361.

Cassett et al. "A peptide mimetic of an anti-CD4 monoclonal antibody by rational design." Biochemical and biophysical research communications 307.1 (2003): 198-205.

Cavalieri et al. "Human T lymphocytes transduced by lentiviral vectors in the absence of TCR activation maintain an intact immune competence." Blood 102.2 (2003): 497-505.

Cereghino et al. "New selectable marker/auxotrophic host strain combinations for molecular genetic manipulation of Pichia pastoris." Gene 263.1-2 (2001): 159-169.

Chames et al. "TCR-like human antibodies expressed on human CTLs mediate antibody affinity-dependent cytolytic activity." The Journal of Immunology 169.2 (2002): 1110-1118.

Chang et al. "A general method for facilitating heterodimeric pairing between two proteins: application to expression of alpha and beta T-cell receptor extracellular segments." Proceedings of the National Academy of Sciences 91.24 (1994): 11408-11412.

Chang et al. "Conditional ligands for A sian HLA variants facilitate the definition of CD 8+ T-cell responses in acute and chronic viral diseases." European journal of immunology 43.4 (2013): 1109-1120.

Chang et al. "Opportunities and challenges for TCR mimic antibodies in cancer therapy." Expert opinion on biological therapy 16.8 (2016): 979-987.

Chicaybam et al. "An efficient low cost method for gene transfer to T lymphocytes." PloS one 8.3 (2013): e60298.

Choo et al. "Bioorthogonal cleavage and exchange of major histocompatibility complex ligands by employing azobenzene-containing peptides." Angewandte Chemie International Edition 53.49 (2014): 13390-13394.

Clarke et al. "Multispecific antibody development platform based on human heavy chain antibodies." Frontiers in immunology 9 (2019): 3037.

Clynes et al. "Fc receptors are required in passive and active immunity to melanoma." Proceedings of the National Academy of Sciences 95.2 (1998): 652-656.

Cohen et al. "Enhanced antitumor activity of murine-human hybrid T-cell receptor (TCR) in human lymphocytes is associated with improved pairing and TCR/CD3 stability." Cancer research 66.17 (2006): 8878-8886.

Cohen et al. "Enhanced antitumor activity of T cells engineered to express T-cell receptors with a second disulfide bond." Cancer research 67.8 (2007): 3898-3903.

Cohen et al. "Recombinant antibodies with MHC-restricted, peptide-specific, T-cell receptor-like specificity: new tools to study antigen presentation and TCR—peptide—MHC interactions." Journal of Molecular Recognition 16.5 (2003): 324-332.

Coloma et al. "Design and production of novel tetravalent bispecific antibodies." Nature biotechnology 15.2 (1997): 159-163.

Cooper et al. "T-cell clones can be rendered specific for CD19: Toward the selective augmentation of the graft-versus-B—lineage leukemia effect." Blood, The Journal of the American Society of Hematology 101.4 (2003): 1637-1644.

Craddock et al. "Enhanced tumor trafficking of GD2 chimeric antigen receptor T cells by expression of the chemokine receptor CCR2b." Journal of immunotherapy 33.8 (2010): 780-788.

Cragg et al. "Antibody specificity controls in vivo effector mechanisms of anti-CD20 reagents." Blood 103.7 (2004): 2738-2743.

Cragg et al. "Complement-mediated lysis by anti-CD20 mAb correlates with segregation into lipid rafts." Blood, The Journal of the American Society of Hematology 101.3 (2003): 1045-1052.

Database GenBank: 4PRN_A, "Chain A, Hla Class I Histocompatibility Antigen, B-35 Alpha Chain," Accession No. 4PRN_A, Jun. 18, 2014 [retrieved on Apr. 28, 2024]. Retrieved from the Internet: <URL: https://www.ncbi.nlm.nih.gov/protein/618855286>, 3 pages.

Database GenBank: AGP00831.1, "immunoglobulin A heavy chain variable region, partial [*Homo sapiens*]," Accession No. AGP00831, Jul. 7, 2013 [retrieved on Apr. 8, 2022]. Retrieved from the Internet: <https://www.ncbi.nlm.nih.gov/protein/AGP00831.1>, 2 pages.

Database UniProt: A0A1D3TZM3_HUMAN, "MHC class I antigen {ECO:0000313 | EMBL:SCQ05563.1}," Accession No. A0A1D3TZM3, Nov. 30, 2016 [retrieved on Mar. 7, 2022]. Retrieved from the internet: <URL: https://www.uniprot.org/uniprot/A0A1D3TZM3.txt?version=5>, 2 pages.

Database UniProt: A0A357ARF6_9FIRM, "SGL domain-containing protein," Accession No. A0A357ARF6, Nov. 7, 2018

(56)         References Cited

OTHER PUBLICATIONS

[retrieved on Mar. 1, 2021]. Retrieved from the internet: <URL: https://www.uniprot.org/uniprot/A0A357ARF6>, 3 pages.

Database UniProt: CD28_HUMAN, "Full=T-cell-specific surface glycoprotein CD28," Accession No. P10747, Jul. 1, 1989 [retrieved on Apr. 29, 2020]. Retrieved from the internet: <URL: https://www.uniprot.org/uniprot/P10747.txt>, 8 pages.

Database UniProt: O19626_HUMAN, "B-3501 {ECO:0000313|EMBL:AAA19925.1}," Accession No. 019626, Jan. 1, 1998 [retrieved on Dec. 9, 2019]. Retrieved from the internet: <URL: https://www.uniprot.org/uniprot/O19626.txt?version=113>, 6 pages.

Database UniProt: TNR9_HUMAN, "Full=Tumor necrosis factor receptor superfamily member 9," Accession No. Q07011, Feb. 1, 1995 [retrieved on Apr. 29, 2020]. Retrieved from the internet: <URL: https://www.uniprot.org/uniprot/Q07011.txt>, 6 pages.

Davila et al. "CD19 CAR-targeted T cells induce long-term remission and B Cell Aplasia in an immunocompetent mouse model of B cell acute lymphoblastic leukemia." PloS one 8.4 (2013): e61338.

Davis et al. "SEEDbodies: fusion proteins based on strand-exchange engineered domain (SEED) CH3 heterodimers in an Fc analogue platform for asymmetric binders or immunofusions and bispecific antibodies." Protein Engineering, Design & Selection 23.4 (2010): 195-202.

De Pascalis et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.

Dhanik et al. "In-silico discovery of cancer-specific peptide-HLA complexes for targeted therapy." BMC bioinformatics 17.1 (2016): 286.

Doerr, A. "Mass spectrometry-based targeted proteomics." Nature methods 10.1 (2013): 23.

Doppalapudi et al. "Chemical generation of bispecific antibodies." Proceedings of the National Academy of Sciences 107.52 (2010): 22611-22616.

Edwards et al. "The remarkable flexibility of the human antibody repertoire; isolation of over one thousand different antibodies to a single protein, BLyS." Journal of molecular biology 334.1 (2003): 103-118.

Non-Final Office Action for copending U.S. Appl. No. 17/820,434, dated Jan. 15, 2026, 75 pages.

* cited by examiner

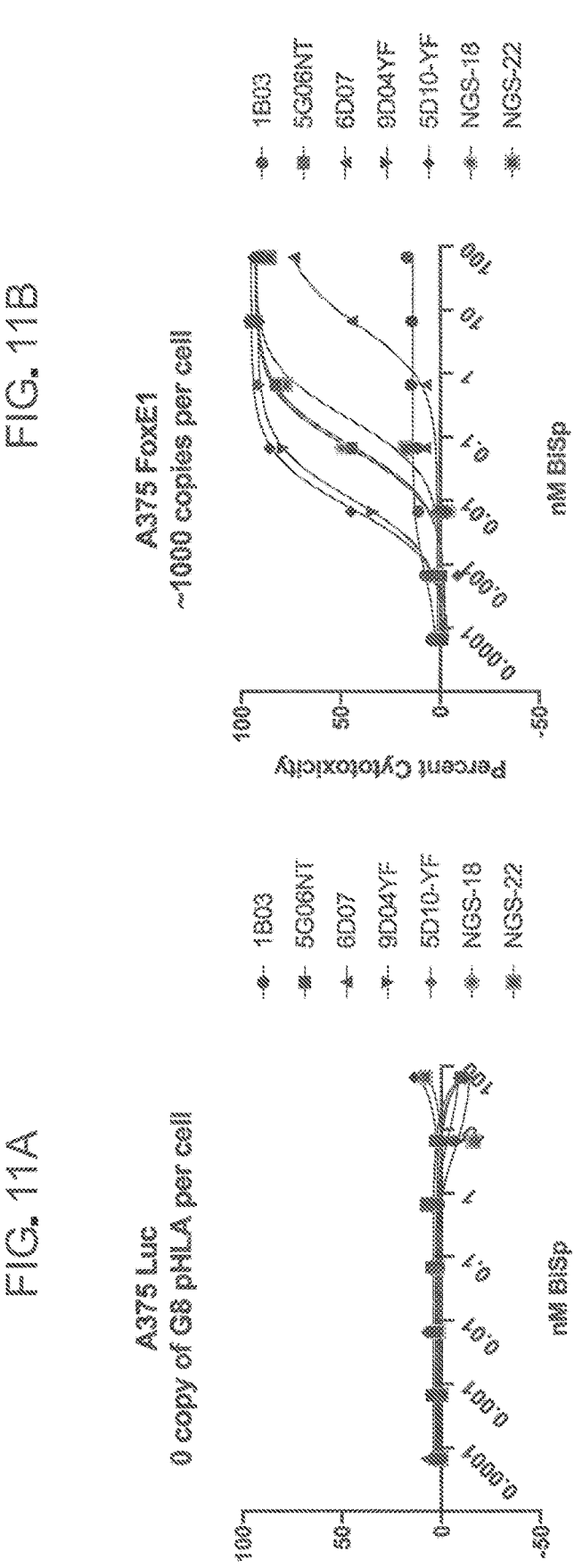

SEQUENCE LISTING

Sequence total quantity: 87
SEQ ID NO: 1          moltype = AA   length = 124
FEATURE               Location/Qualifiers
REGION                1..124
                      note = Description of Artificial Sequence: Synthetic
                       polypeptide
source                1..124
                      mol_type = protein
                      organism = synthetic construct
SEQUENCE: 1
EVQLLESGGG LVQPGGSLRL SCAASGYTFS DYYMSWVRQA PGKGLEWVSG INWPGGSTGY   60
ADSVKGRFTI SRDNSKNTLY LQMNSLRAED TAVYYCARVE QGYDIYYYYY MDVWGKGTTV   120
TVSS                                                                124

SEQ ID NO: 2          moltype = AA   length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 2
DIQMTQSPSS LSASVGDRVT ITCRASQSIS SYLNWYQQKP GKAPKLLIYK ASSLESGVPS   60
RFSGSGSGTD FTLTISSLQP EDFATYYCQQ SYSAPYTFGP GTKVDIK                 107

SEQ ID NO: 3          moltype = AA   length = 124
FEATURE               Location/Qualifiers
REGION                1..124
                      note = Description of Artificial Sequence: Synthetic
                       polypeptide
source                1..124
                      mol_type = protein
                      organism = synthetic construct
SEQUENCE: 3
EVQLLESGGG LVQPGGSLRL SCAASGYTFS DYYMSWVRQA PGKGLEWVGN INWNGGSTLY   60
ADSVKGRFTI SRDNSKNTLY LQMNSLRAED TAVYYCARVE QGYDNYYYYY MDVWGKGTTV   120
TVSS                                                                124

SEQ ID NO: 4          moltype = AA   length = 124
FEATURE               Location/Qualifiers
REGION                1..124
                      note = Description of Artificial Sequence: Synthetic
                       polypeptide
source                1..124
                      mol_type = protein
                      organism = synthetic construct
SEQUENCE: 4
EVQLLESGGG LVQPGGSLRL SCAASGYTFS DYYMSWVRQA PGKGLEWVSG INWPGGYTGY   60
ADSVKGRFTI SRDNSKNTLY LQMNSLRAED TAVYYCARVE QGYDIYYYYY MDVWGKGTTV   120
TVSS                                                                124

-continued

```
SEQ ID NO: 5                moltype = AA  length = 124
FEATURE                     Location/Qualifiers
REGION                      1..124
                            note = Description of Artificial Sequence: Synthetic
                             polypeptide
source                      1..124
                            mol_type = protein
                            organism = synthetic construct
SEQUENCE: 5
EVQLLESGGG LVQPGGSLRL SCAASGYTFS DYYMSWVRQA PGKGLEWVSG INWYSGSTGY   60
ADSVKGRFTI SRDNSKNTLY LQMNSLRAED TAVYYCARVE QGYDIYYYYY MDVWGKGTTV  120
TVSS                                                               124

SEQ ID NO: 6                moltype = AA  length = 124
FEATURE                     Location/Qualifiers
REGION                      1..124
                            note = Description of Artificial Sequence: Synthetic
                             polypeptide
source                      1..124
                            mol_type = protein
                            organism = synthetic construct
SEQUENCE: 6
EVQLLESGGG LVQPGGSLRL SCAASGYTFS DYYMSWVRQA PGKGLEWVSG INWPGSSTGY   60
ADSVKGRFTI SRDNSKNTLY LQMNSLRAED TAVYYCARVE QGYDIYYYYY MDVWGKGTTV  120
TVSS                                                               124

SEQ ID NO: 7                moltype = AA  length = 124
FEATURE                     Location/Qualifiers
REGION                      1..124
                            note = Description of Artificial Sequence: Synthetic
                             polypeptide
source                      1..124
                            mol_type = protein
                            organism = synthetic construct
SEQUENCE: 7
EVQLLESGGG LVQPGGSLRL SCAASGFTFS DYYMSWVRQA PGKGLEWVSG INWPGGSTGY   60
ADSVKGRFNI SRDNSKNTLY LQMNSLRAED TAVYYCARVE QGYDIYYFYY MDVWGKGTTV  120
TVSS                                                               124

SEQ ID NO: 8                moltype = AA  length = 124
FEATURE                     Location/Qualifiers
REGION                      1..124
                            note = Description of Artificial Sequence: Synthetic
                             polypeptide
source                      1..124
                            mol_type = protein
                            organism = synthetic construct
SEQUENCE: 8
EVQLLESGGG LVQPGGSLRL SCAASGFTFS DYYMSWVRQA PGKGLEWVGG INWPGGSTDY   60
ADSVKGRFTI SRDNSKNTLY LQMNSLRAED TAVYYCARVE QGYDIYYYYY MDVWGKGTTV  120
TVSS                                                               124

SEQ ID NO: 9                moltype = AA  length = 124
FEATURE                     Location/Qualifiers
REGION                      1..124
                            note = Description of Artificial Sequence: Synthetic
                             polypeptide
source                      1..124
                            mol_type = protein
                            organism = synthetic construct
SEQUENCE: 9
EVQLLESGGG LVQPGGSLRL SCAASGFTFS DYYMSWVRQA PGKGLEWVSG INWNGGSTGY   60
ADSVKGRFTI SRDNSKNTLY LQMNSLRDED TAVYYCARVE QGYDIYYYYY MDVWGKGTTV  120
TVSS                                                               124

SEQ ID NO: 10               moltype = AA  length = 107
FEATURE                     Location/Qualifiers
REGION                      1..107
                            note = Description of Artificial Sequence: Synthetic
                             polypeptide
source                      1..107
                            mol_type = protein
                            organism = synthetic construct
SEQUENCE: 10
DIQMTQSPSS LSASVGDRVT ITCRASQSIH SYLNWYQQKP GKAPKLLIYK ASTPYSGVPS   60
RFSGSGSGTD FTLTISSLQP EDFATYYCQQ SYSYPHNFGP GTKVDIK                107

SEQ ID NO: 11               moltype = AA  length = 124
FEATURE                     Location/Qualifiers
```

-continued

```
REGION                   1..124
                         note = Description of Artificial Sequence: Synthetic
                          polypeptide
source                   1..124
                         mol_type = protein
                         organism = synthetic construct
SEQUENCE: 11
EVQLLESGGG LVQPGGSLRL SCAASGFTFS DYYMSWVRQA PGKGLEWVSG INWHHGSTGY   60
ADSVKGRFTI SRDNSKNTLY LQMNSLRAED TAVYYCARVE QGYDIYYYYY MDVWGKGTTV  120
TVSS                                                               124

SEQ ID NO: 12            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 12
EVQLLESGGG LVQPGGSLRL SCAASGYTFS DYYMSWVRQA PGKGLEWVSG INWPGYSTGY   60
ADSVKGRFTI SRDNSKNTLY LQMNSLRAED TAVYYCARVE QGYDNYYYYY MDVWGKGTTV  120
TVSS                                                               124

SEQ ID NO: 13            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 13
EVQLLESGGG LVQPGGSLRL SCAASGFTFS DYYMSWVRQA PGKGLEWVSG INWPGSSTGY   60
ADSVKGRFTI SRDNSKNTLY LQMNSLRAED TAVYYCARVR QGYDYYYYYY MDVWGKGTTV  120
TVSS                                                               124

SEQ ID NO: 14            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 14
EVQLLESGGG LVQPGGSLRL SCAASGFTFS DYYMSWVRQA PGKGLEWVSV INWPGSSTGY   60
ADSVKGRFTI SRDNSKNTLY LQMNSLRAED TAVYYCARVE QGYDIYYYYY MDVWGKGTTV  120
TVSS                                                               124

SEQ ID NO: 15            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 15
EVQLLESGGG LVQPGGSLRL SCAASGFTFS DYYMSWVRQA PGKGLEWVSG INWNGGSTGY   60
ADSVKGRFTI SRDNSKNTLY LQMNSLRAED TAVYYCARVE QGYDIYYYYY MDVWGKGTTV  120
TVSS                                                               124

SEQ ID NO: 16            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 16
DYYMS                                                                5

SEQ ID NO: 17            moltype = AA  length = 17
FEATURE                  Location/Qualifiers
REGION                   1..17
                         note = Description of Artificial Sequence: Synthetic peptide
source                   1..17
                         mol_type = protein
```

-continued

```
                              organism = synthetic construct
SEQUENCE: 17
GINWYSGSTG YADSVKG                                                  17

SEQ ID NO: 18          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 18
VINWPGSSTG YADSVKG                                                  17

SEQ ID NO: 19          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 19
GINWPGGSTG YADSVKG                                                  17

SEQ ID NO: 20          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 20
GINWHHGSTG YADSVKG                                                  17

SEQ ID NO: 21          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 21
GINWPGGSTD YADSVKG                                                  17

SEQ ID NO: 22          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 22
GINWPGSSTG YADSVKG                                                  17

SEQ ID NO: 23          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 23
NINWNGGSTL YADSVKG                                                  17

SEQ ID NO: 24          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 24
GINWPGGYTG YADSVKG                                                  17

SEQ ID NO: 25          moltype = AA  length = 17
FEATURE                Location/Qualifiers
REGION                 1..17
                       note = Description of Artificial Sequence: Synthetic peptide
source                 1..17
```

```
                            mol_type = protein
                            organism = synthetic construct
SEQUENCE: 25
GINWPGYSTG YADSVKG                                              17

SEQ ID NO: 26               moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 26
GINWNGGSTG YADSVKG                                              17

SEQ ID NO: 27               moltype = AA  length = 15
FEATURE                     Location/Qualifiers
REGION                      1..15
                            note = Description of Artificial Sequence: Synthetic peptide
source                      1..15
                            mol_type = protein
                            organism = synthetic construct
SEQUENCE: 27
VEQGYDIYYY YYMDV                                                15

SEQ ID NO: 28               moltype = AA  length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 28
RASQSISSYL N                                                   11

SEQ ID NO: 29               moltype = AA  length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 29
RASQSIHSYL N                                                   11

SEQ ID NO: 30               moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 30
KASSLES                                                         7

SEQ ID NO: 31               moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 31
KASTPYS                                                         7

SEQ ID NO: 32               moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 32
QQSYSAPYT                                                       9

SEQ ID NO: 33               moltype = AA  length = 9
FEATURE                     Location/Qualifiers
REGION                      1..9
                            note = Description of Artificial Sequence: Synthetic peptide
```

-continued

```
source                  1..9
                        mol_type = protein
                        organism = synthetic construct
SEQUENCE: 33
QQSYSYPHN                                                             9

SEQ ID NO: 34           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 34
VEQGYDIYYF YYMDV                                                      15

SEQ ID NO: 35           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 35
VRQGYDYYYY YYMDV                                                      15

SEQ ID NO: 36           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 36
VEQGYDNYYY YYMDV                                                      15

SEQ ID NO: 37           moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 37
EVQLLESGGG LVQPGGSLRL SCAASGFTFS DYYMSWVRQA PGKGLEWVSG INWPGSSTGY     60
ADSVKGRFTI SRDNSKNTLY LQMNSLRAED TAVYYCARVE QGYDIYYYYY MDVWGKGTTV     120
TVSS                                                                  124

SEQ ID NO: 38           moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 38
EVQLLESGGG LVQPGGSLRL SCAASGFTFS DYYMSWVRQA PGKGLEWVSG INWPGGSTGY     60
ADSVKGRFTI SRDNSKNTLY LQMNSLRAED TAVYYCARVE QGYDIYYFYY MDVWGKGTTV     120
TVSS                                                                  124

SEQ ID NO: 39           moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 39
EVQLLESGGG LVQPGGSLRL SCAASGFTFS DYYMSWVRQA PGKGLEWVSG INWPGYSTGY     60
ADSVKGRFTI SRDNSKNTLY LQMNSLRAED TAVYYCARVE QGYDNYYYYY MDVWGKGTTV     120
TVSS                                                                  124

SEQ ID NO: 40           moltype = AA   length = 124
FEATURE                 Location/Qualifiers
REGION                  1..124
                        note = Description of Artificial Sequence: Synthetic
```

-continued

```
                         polypeptide
source                   1..124
                         mol_type = protein
                         organism = synthetic construct
SEQUENCE: 40
EVQLLESGGG LVQPGGSLRL SCAASGFTFS DYYMSWVRQA PGKGLEWVSG INWPGGSTGY   60
ADSVKGRFTI SRDNSKNTLY LQMNSLRAED TAVYYCARVE QGYDIYYYYY MDVWGKGTTV   120
TVSS                                                               124

SEQ ID NO: 41            moltype = AA  length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 41
EVQLLESGGG LVQPGGSLRL SCAASGFTFS DYYMSWVRQA PGKGLEWVSG INWYSGSTGY   60
ADSVKGRFTI SRDNSKNTLY LQMNSLRAED TAVYYCARVE QGYDIYYYYY MDVWGKGTTV   120
TVSS                                                               124

SEQ ID NO: 42            moltype = AA  length = 10
FEATURE                  Location/Qualifiers
source                   1..10
                         mol_type = protein
                         organism = Homo sapiens
SEQUENCE: 42
AIFPGAVPAA                                                          10

SEQ ID NO: 43            moltype = AA  length = 5
FEATURE                  Location/Qualifiers
source                   1..5
                         mol_type = protein
                         organism = synthetic construct
REGION                   5
                         note = The entire sequence of amino acids 1-5 can be
                          repeated one to six times.
SEQUENCE: 43
GGGGS                                                               5

SEQ ID NO: 44            moltype = AA  length = 4
FEATURE                  Location/Qualifiers
REGION                   1..4
                         note = Description of Artificial Sequence: Synthetic
                          polypeptide
source                   1..4
                         mol_type = protein
                         organism = synthetic construct
REGION                   4
                         note = The entire sequence of amino acids 1-4 can be
                          repeated one to twenty times.
SEQUENCE: 44
GSGS                                                                4

SEQ ID NO: 45            moltype = AA  length = 6
FEATURE                  Location/Qualifiers
REGION                   1..6
                         note = Description of Artificial Sequence: Synthetic
                          polypeptide
source                   1..6
                         mol_type = protein
                         organism = synthetic construct
REGION                   6
                         note = The entire sequence of amino acids 1-6 can be
                          repeated one to twenty times.
SEQUENCE: 45
GGSGGS                                                              6

SEQ ID NO: 46            moltype = AA  length = 4
FEATURE                  Location/Qualifiers
REGION                   1..4
                         note = Description of Artificial Sequence: Synthetic
                          polypeptide
source                   1..4
                         mol_type = protein
                         organism = synthetic construct
REGION                   4
                         note = The entire sequence of amino acids 1-4 can be
```

```
                      repeated one to twenty times.
SEQUENCE: 46
GGGS                                                            4

SEQ ID NO: 47         moltype = AA  length = 4
FEATURE               Location/Qualifiers
REGION                1..4
                      note = Description of Artificial Sequence: Synthetic
                       polypeptide
source                1..4
                      mol_type = protein
                      organism = synthetic construct
REGION                4
                      note = The entire sequence of amino acids 1-4 can be
                       repeated one to twenty times.

SEQUENCE: 47
GGSG                                                            4

SEQ ID NO: 48         moltype = AA  length = 5
FEATURE               Location/Qualifiers
REGION                1..5
                      note = Description of Artificial Sequence: Synthetic
                       polypeptide
source                1..5
                      mol_type = protein
                      organism = synthetic construct
REGION                5
                      note = The entire sequence of amino acids 1-5 can be
                       repeated one to twenty times.

SEQUENCE: 48
GGSGG                                                           5

SEQ ID NO: 49         moltype = AA  length = 5
FEATURE               Location/Qualifiers
REGION                1..5
                      note = Description of Artificial Sequence: Synthetic
                       polypeptide
source                1..5
                      mol_type = protein
                      organism = synthetic construct
REGION                5
                      note = The entire sequence of amino acids 1-5 can be
                       repeated one to twenty times.

SEQUENCE: 49
GGGGS                                                           5

SEQ ID NO: 50         moltype = AA  length = 5
FEATURE               Location/Qualifiers
REGION                1..5
                      note = Description of Artificial Sequence: Synthetic
                       polypeptide
source                1..5
                      mol_type = protein
                      organism = synthetic construct
REGION                5
                      note = The entire sequence of amino acids 1-5 can be
                       repeated one to twenty times.

SEQUENCE: 50
GSGGG                                                           5

SEQ ID NO: 51         moltype = AA  length = 5
FEATURE               Location/Qualifiers
REGION                1..5
                      note = Description of Artificial Sequence: Synthetic
                       polypeptide
source                1..5
                      mol_type = protein
                      organism = synthetic construct
REGION                5
                      note = The entire sequence of amino acids 1-5 can be
                       repeated one to twenty times.

SEQUENCE: 51
GGGSG                                                           5

SEQ ID NO: 52         moltype = AA  length = 5
FEATURE               Location/Qualifiers
REGION                1..5
                      note = Description of Artificial Sequence: Synthetic
                       polypeptide
```

-continued

```
source                  1..5
                        mol_type = protein
                        organism = synthetic construct
REGION                  5
                        note = The entire sequence of amino acids 1-5 can be
                         repeated one to twenty times.
SEQUENCE: 52
GGGGG                                                                  5

SEQ ID NO: 53           moltype = AA  length = 10
FEATURE                 Location/Qualifiers
source                  1..10
                        mol_type = protein
                        organism = Homo sapiens
SEQUENCE: 53
ALFPSGVPAA                                                             10

SEQ ID NO: 54           moltype = AA  length = 10
FEATURE                 Location/Qualifiers
source                  1..10
                        mol_type = protein
                        organism = Homo sapiens
SEQUENCE: 54
TVFPGAVPVL                                                             10

SEQ ID NO: 55           moltype = AA  length = 10
FEATURE                 Location/Qualifiers
source                  1..10
                        mol_type = protein
                        organism = Homo sapiens
SEQUENCE: 55
FIFPGLLPEA                                                             10

SEQ ID NO: 56           moltype = AA  length = 10
FEATURE                 Location/Qualifiers
source                  1..10
                        mol_type = protein
                        organism = Homo sapiens
SEQUENCE: 56
GIGPGGVAAA                                                             10

SEQ ID NO: 57           moltype = AA  length = 10
FEATURE                 Location/Qualifiers
source                  1..10
                        mol_type = protein
                        organism = Homo sapiens
SEQUENCE: 57
SAFAGAVRAA                                                             10

SEQ ID NO: 58           moltype = DNA  length = 43
FEATURE                 Location/Qualifiers
misc_feature            1..43
                        note = Description of Artificial Sequence: Synthetic primer
source                  1..43
                        mol_type = other DNA
                        organism = synthetic construct
SEQUENCE: 58
ctttctctcc acaggtgtac actccgaggt tcagctcctg gag                        43

SEQ ID NO: 59           moltype = DNA  length = 47
FEATURE                 Location/Qualifiers
misc_feature            1..47
                        note = Description of Artificial Sequence: Synthetic primer
source                  1..47
                        mol_type = other DNA
                        organism = synthetic construct
SEQUENCE: 59
agagcccct ccgccggatc cccctccgcc cttgatgtcc accttag                     47

SEQ ID NO: 60           moltype = AA  length = 9
FEATURE                 Location/Qualifiers
source                  1..9
                        mol_type = protein
                        organism = Homo sapiens
SEQUENCE: 60
NTDNNLAVY                                                              9

SEQ ID NO: 61           moltype = AA  length = 9
FEATURE                 Location/Qualifiers
```

-continued

```
source                   1..9
                         mol_type = protein
                         organism = Homo sapiens
SEQUENCE: 61
LLASSILCA                                                             9

SEQ ID NO: 62            moltype = AA   length = 9
FEATURE                  Location/Qualifiers
source                   1..9
                         mol_type = protein
                         organism = Homo sapiens
SEQUENCE: 62
EVDPIGHVY                                                             9

SEQ ID NO: 63            moltype = AA   length = 10
FEATURE                  Location/Qualifiers
source                   1..10
                         mol_type = protein
                         organism = Homo sapiens
SEQUENCE: 63
ASSLPTTMNY                                                            10

SEQ ID NO: 64            moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 64
cagctgtgcc gccagcggc                                                  19

SEQ ID NO: 65            moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 65
gtcacggtgg ttcccttgc                                                  19

SEQ ID NO: 66            moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 66
tagggtgacc ataacctgc                                                  19

SEQ ID NO: 67            moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 67
ccttagttcc agggccgaa                                                  19

SEQ ID NO: 68            moltype = DNA   length = 372
FEATURE                  Location/Qualifiers
misc_feature             1..372
                         note = Description of Artificial Sequence: Synthetic
                          polynucleotide
source                   1..372
                         mol_type = other DNA
                         organism = synthetic construct
SEQUENCE: 68
gaggttcagc tcctggagag cggcggaggt ctggtgcagc cgggtggctc actgaggctc    60
agctgtgccg ccagcggcta caccttcagc gattattaca tgagctgggt gcgacaggcc   120
ccaggaaaag gcctggagtg ggtgagcggc atcaactggc cgggcgggag caccggctac   180
gccgacagcg tgaagggcag gttcaccatc agcagggaca acagcaagaa caccctgtac   240
ctgcagatga acagcctgag ggccgaggac accgccgtgt actactcgc cagggtggag   300
cagggctacg acatatacta ttactactac atggacgtgt ggggcaaggg aaccaccgtg   360
accgtgagca gc                                                        372
```

-continued

```
SEQ ID NO: 69          moltype = DNA   length = 321
FEATURE                Location/Qualifiers
misc_feature           1..321
                       note = Description of Artificial Sequence: Synthetic
                       polynucleotide
source                 1..321
                       mol_type = other DNA
                       organism = synthetic construct
SEQUENCE: 69
gacatccaga tgacccagag ccccagcagc ctgagcgcca gcgtgggcga tagggtgacc   60
ataacctgcc gagccagcca gagcatcagc agctacctga actggtatca acagaagccc  120
ggcaaggccc ccaagctcct gatctacaag gccagcagtc tggagagcgg cgtgccctcc  180
aggttcagcg gcagcggaag cggcaccgac tttaccctga ccatcagctc cttgcagccc  240
gaggacttcg ccacctacta ctgccagcaa agctactcag ccccctacac cttcggccct  300
ggaactaagg tggacatcaa g                                            321

SEQ ID NO: 70          moltype = DNA   length = 372
FEATURE                Location/Qualifiers
misc_feature           1..372
                       note = Description of Artificial Sequence: Synthetic
                       polynucleotide
source                 1..372
                       mol_type = other DNA
                       organism = synthetic construct
SEQUENCE: 70
gaggttcagc tcctggagag cggcggaggt ctggtgcagc cgggtggctc actgaggctc   60
agctgtgccg ccagcggcta caccttcagc gattattaca tgagctgggt gcgacaggcc  120
ccaggaaaag gcctggagtg ggtgggtaat atcaactgga acggcgggag caccttgtac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acaattacta ttactactac atggacgtgt ggggcaaggg aaccaccgtg  360
accgtgagca gc                                                      372

SEQ ID NO: 71          moltype = DNA   length = 372
FEATURE                Location/Qualifiers
misc_feature           1..372
                       note = Description of Artificial Sequence: Synthetic
                       polynucleotide
source                 1..372
                       mol_type = other DNA
                       organism = synthetic construct
SEQUENCE: 71
gaggttcagc tcctggagag cggcggaggt ctggtgcagc cgggtggctc actgaggctc   60
agctgtgccg ccagcggcta caccttcagc gattattaca tgagctgggt gcgacaggcc  120
ccaggaaaag gcctggagtg ggtgagcggc atcaactggc cgggcgggta taccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 72          moltype = DNA   length = 372
FEATURE                Location/Qualifiers
misc_feature           1..372
                       note = Description of Artificial Sequence: Synthetic
                       polynucleotide
source                 1..372
                       mol_type = other DNA
                       organism = synthetic construct
SEQUENCE: 72
gaggttcagc tcctggagag cggcggaggt ctggtgcagc cgggtggctc actgaggctc   60
agctgtgccg ccagcggcta caccttcagc gattattaca tgagctgggt gcgacaggcc  120
ccaggaaaag gcctggagtg ggtgagcggc atcaactggt attccgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 73          moltype = DNA   length = 372
FEATURE                Location/Qualifiers
misc_feature           1..372
                       note = Description of Artificial Sequence: Synthetic
                       polynucleotide
source                 1..372
                       mol_type = other DNA
                       organism = synthetic construct
SEQUENCE: 73
gaggttcagc tcctggagag cggcggaggt ctggtgcagc cgggtggctc actgaggctc   60
agctgtgccg ccagcggcta caccttcagc gattattaca tgagctgggt gcgacaggcc  120
ccaggaaaag gcctggagtg ggtgagcggc atcaactggc cgggctctag caccggctac  180
```

-continued

```
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                       372
```

```
SEQ ID NO: 74            moltype = DNA   length = 372
FEATURE                  Location/Qualifiers
misc_feature             1..372
                         note = Description of Artificial Sequence: Synthetic
                          polynucleotide
source                   1..372
                         mol_type = other DNA
                         organism = synthetic construct
SEQUENCE: 74
gaggttcagc tcctggagag cggcggaggt ctggtgcagc cgggtggctc actgaggctc  60
agctgtgccg ccagcggctt caccttcagc gattattaca tgagctgggt gcgacaggcc  120
ccaggaaaag gcctggagtg ggtgagcggc atcaactggc ctggcgggag caccggctac  180
gccgacagcg tgaagggcag gttcaacatc agcagggaca acagcaagaa caccctgtac  240
ctgcagatga acagcctgag ggccgaggac accgccgtgt actactgcgc cagggtggag  300
cagggctacg acatatacta tttctactac atggacgtgt ggggcaaggg aaccaccgtg  360
accgtgagca gc                                                       372
```

```
SEQ ID NO: 75            moltype = DNA   length = 372
FEATURE                  Location/Qualifiers
misc_feature             1..372
                         note = Description of Artificial Sequence: Synthetic
                          polynucleotide
source                   1..372
                         mol_type = other DNA
                         organism = synthetic construct
SEQUENCE: 75
gaggttcagc tcctggagag cggcggaggt ctggtgcagc cgggtggctc actgaggctc  60
agctgtgccg ccagcggctt caccttcagc gattattaca tgagctgggt gcgacaggcc  120
ccaggaaaag gcctggagtg ggtgggaggc atcaactggc cgggcgggag caccgactac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                       372
```

```
SEQ ID NO: 76            moltype = DNA   length = 372
FEATURE                  Location/Qualifiers
misc_feature             1..372
                         note = Description of Artificial Sequence: Synthetic
                          polynucleotide
source                   1..372
                         mol_type = other DNA
                         organism = synthetic construct
SEQUENCE: 76
gaggttcagc tcctggagag cggcggaggt ctggtgcagc cgggtggctc actgaggctc  60
agctgtgccg ccagcggctt caccttcagc gattattaca tgagctgggt gcgacaggcc  120
ccaggaaaag gcctggagtg ggtgagcggc atcaactgga acggcgggag caccggctac  180
gccgacagcg tgaagggcag gttcaccatc agcagggaca acagcaagaa caccctgtac  240
ctgcagatga acagcctgag ggacgaggac accgccgtgt actactgcgc cagggtggag  300
cagggctacg acatatacta ttactactac atggacgtgt ggggcaaggg aaccaccgtg  360
accgtgagca gc                                                       372
```

```
SEQ ID NO: 77            moltype = DNA   length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 77
gacatccaga tgacccagag cccccagcagc ctgagcgcca gcgtgggcga tagggtgacc  60
ataacctgcc gagccagcca gagcatccac agctacctga actggtatca acagaagccc  120
ggcaaggccc ccaagctcct gatctacaag gccagcactc cctacagcgg cgtgccctcc  180
aggttcagcg gcagcggaag cggcaccgac tttaccctga ccatcagctc cttgcagccc  240
gaggacttcg ccacctacta ctgccagcaa agctactcat accccataa tttcggccct  300
ggaactaagg tggacatcaa g                                             321
```

```
SEQ ID NO: 78            moltype = DNA   length = 372
FEATURE                  Location/Qualifiers
misc_feature             1..372
                         note = Description of Artificial Sequence: Synthetic
                          polynucleotide
source                   1..372
                         mol_type = other DNA
```

```
                        organism = synthetic construct
SEQUENCE: 78
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactgac atcatgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 79           moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 79
gaggttcagc tcctggagag cggcggaggt ctggtgcagc cgggtggctc actgaggctc   60
agctgtgccg ccagcggcta caccttcagc gattattaca tgagctgggt gcgacaggcc  120
ccaggaaaag gcctggagtg ggtgagcggc atcaactggc atcatgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acaattacta ttactactac atggacgtgt ggggcaaggg aaccaccgtg  360
accgtgagca gc                                                      372

SEQ ID NO: 80           moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 80
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggc caggctctag caccggctac  180
gccgacagcg tgaagggcag gttcaccatc agcagggaca acagcaagaa caccctgtac  240
ctgcagatga acagcctgag ggccgaggac accgccgtgt actactgcgc cagggtgcgg  300
cagggctacg actattacta ttactactac atggacgtgt ggggcaaggg aaccaccgtg  360
accgtgagca gc                                                      372

SEQ ID NO: 81           moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 81
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcgtg atcaactggc cgggctctag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 82           moltype = DNA  length = 372
FEATURE                 Location/Qualifiers
misc_feature            1..372
                        note = Description of Artificial Sequence: Synthetic
                         polynucleotide
source                  1..372
                        mol_type = other DNA
                        organism = synthetic construct
SEQUENCE: 82
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactgga acggcgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 83           moltype = DNA  length = 372
```

-continued

```
FEATURE              Location/Qualifiers
misc_feature         1..372
                     note = Description of Artificial Sequence: Synthetic
                     polynucleotide
source               1..372
                     mol_type = other DNA
                     organism = synthetic construct SEQUENCE: 83
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggc cgggctctag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 84         moltype = DNA   length = 372
FEATURE              Location/Qualifiers
misc_feature         1..372
                     note = Description of Artificial Sequence: Synthetic
                     polynucleotide
source               1..372
                     mol_type = other DNA
                     organism = synthetic construct SEQUENCE: 84
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggc ctggcgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta tttctactac atggacgtgt ggggcaaggg aaccaccgtg  360
accgtgagca gc                                                      372

SEQ ID NO: 85         moltype = DNA   length = 372
FEATURE              Location/Qualifiers
misc_feature         1..372
                     note = Description of Artificial Sequence: Synthetic
                     polynucleotide
source               1..372
                     mol_type = other DNA
                     organism = synthetic construct SEQUENCE: 85
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggc caggctatag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acaattacta ttactactac atggacgtgt ggggcaaggg aaccaccgtg  360
accgtgagca gc                                                      372

SEQ ID NO: 86         moltype = DNA   length = 372
FEATURE              Location/Qualifiers
misc_feature         1..372
                     note = Description of Artificial Sequence: Synthetic
                     polynucleotide
source               1..372
                     mol_type = other DNA
                     organism = synthetic construct SEQUENCE: 86
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggc caggcgggag caccggctac  180
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                      372

SEQ ID NO: 87         moltype = DNA   length = 372
FEATURE              Location/Qualifiers
misc_feature         1..372
                     note = Description of Artificial Sequence: Synthetic
                     polynucleotide
source               1..372
                     mol_type = other DNA
                     organism = synthetic construct SEQUENCE: 87
gaggttcagc tcctggagag cggcggaggt ctggtgcagc cgggtggctc actgaggctc   60
agctgtgccg ccagcggctt caccttcagc gattattaca tgagctgggt gcgacaggcc  120
ccaggaaaag gcctggagtg ggtgagcggc atcaactggt attccgggag caccggctac  180
```

US 12,630,637 B2

-continued

```
gccgacagcg tgaagggcag gttcaccatc agcagggaca acagcaagaa caccctgtac  240
ctgcagatga acagcctgag ggccgaggac accgccgtgt actactgcgc cagggtggag  300
cagggctacg acatatacta ttactactac atggacgtgt ggggcaaggg aaccaccgtg  360
accgtgagca gc                                                     372
```

1

ANTIGEN-BINDING PROTEINS AND RELATED METHODS OF USE

CROSS REFERENCE TO RELATED APPLICATIONS

This application is a continuation of U.S. application Ser. No. 18/300,747, filed on Apr. 14, 2023, which is a continuation of International Application No. PCT/US2021/055261, filed on Oct. 15, 2021, which claims the benefit of U.S. Provisional Application No. 63/092,457, filed on Oct. 15, 2020, the disclosure of each of which is incorporated by reference herein in its entirety.

SEQUENCE LISTING

The instant application contains a Sequence Listing which has been submitted via EFS-Web and is hereby incorporated by reference in its entirety. Said .XML copy, created on Apr. 12, 2023, is named GSO-039WOC1, and is 1,22,189 bytes in size.

BACKGROUND

Specific antigen recognition is essential for antibodies to function in the adaptive immune system. The specificity of antibodies and antibody fragments for a particular antigen or antigens makes antibodies desirable therapeutic agents. Antibodies and antibody fragments can be used to target specific tissues, for example, tumor tissue or infected tissue, thereby minimizing potential side effects of non-specific targeting. Thousands of antigens are capable of eliciting responses, each almost exclusively directed to the particular antigen which elicited it.

Tumor cells can express antigens and may display such antigens on the surface of the tumor cell. Such tumor antigens can be used for development of novel immunotherapeutic reagents for the specific targeting of tumor cells. For example, tumor antigens can be used to identify therapeutic antigen binding proteins, e.g., TCRs, antibodies, or antigen-binding fragments. Such tumor antigens may also be utilized in pharmaceutical compositions, e.g., vaccines.

Included in potential antigens for immunotherapeutic applications are major histocompatibility complex class I molecules. Major histocompatibility complex class I molecules are expressed on the surface of virtually all nucleated cells in the body and are dimeric molecules comprising a transmembrane heavy chain, comprising the peptide antigen binding cleft, and a smaller extracellular chain termed beta2-microglobulin. MHC class I molecules present peptides derived from the degradation of cytosolic proteins by the proteasome, a multi-unit structure in the cytoplasm, (Niedermann G., 2002. *Curr Top Microbiol Immunol.* 268: 91-136; for processing of bacterial antigens, refer to Wick M J, and Ljunggren H G., 1999. *Immunol Rev.* 172:153-62, each of which is incorporated by reference in its entirety). Cleaved peptides are transported into the lumen of the endoplasmic reticulum (ER) by the transporter associated with antigen processing (TAP) where they are bound to the groove of the assembled class I molecule, and the resultant MHC/peptide complex is transported to the cell membrane to enable antigen presentation to T lymphocytes (Yewdell J W., 2001. *Trends Cell Biol.* 11:294-7; Yewdell J W. and Bennink J R., 2001. *Curr Opin Immunol.* 13:13-8, each of which is incorporated by reference in its entirety). Alternatively, cleaved peptides can be loaded onto MHC class I molecules in a TAP-independent manner and can also present extracellularly-derived proteins through a process of cross-presentation. As such, a given MHC/peptide complex presents a novel protein structure on the cell surface that can be targeted by a novel antigen-binding protein (e.g., antibodies or TCRs) once the identity of the complex's structure (peptide sequence and MHC subtype) is determined.

Isolated antibodies at high purity, exhibiting potency and high specificity, are in demand for therapeutic applications. Conventional approaches to cancer treatment include chemotherapy, radiation therapy, and surgical removal of solid tumors or tumor-tissue. There is a clear need for the development of more effective chemotherapeutic agents and the use and development of antibodies that target tumor associated antigens is a potential solution.

SUMMARY

Provided herein is an isolated antigen binding protein (ABP) that specifically binds to a human leukocyte antigen (HLA)-PEPTIDE target, wherein the HLA-PEPTIDE target comprises an HLA-restricted peptide complexed with an HLA Class I molecule, wherein the HLA-restricted peptide is located in the peptide binding groove of an α1/α2 heterodimer portion of the HLA Class I molecule, and wherein: the HLA Class I molecule is HLA subtype A*02:01 and the HLA-restricted peptide comprises the sequence AIFPGAVPAA (SEQ ID NO: 42).

In some embodiments, In one aspect, provided herein is an isolated antigen binding protein (ABP) that specifically binds to a human leukocyte antigen (HLA)-PEPTIDE target comprising HLA subtype A*02:01 and a peptide comprising the sequence AIFPGAVPAA (SEQ ID NO: 42), the ABP comprising an antigen-binding site comprising a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3, wherein:

a. the CDR-H1 comprises the sequence set forth in SEQ ID NO:16, the CDR-H2 comprises the sequence set forth in SEQ ID NO:17, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

b. the CDR-H1 comprises the sequence set forth in SEQ ID NO:16, the CDR-H2 comprises the sequence set forth in SEQ ID NO:18, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

c. the CDR-H1 comprises the sequence set forth in SEQ ID NO: 16, the CDR-H2 comprises the sequence set forth in SEQ ID NO:19, the CDR-H3 comprises the sequence set forth in SEQ ID NO:34, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

d. the CDR-H1 comprises the sequence set forth in SEQ ID NO:16, the CDR-H2 comprises the sequence set forth in SEQ ID NO:20, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

e. the CDR-H1 comprises the sequence set forth in SEQ ID NO:16, the CDR-H2 comprises the sequence set forth in SEQ ID NO:21, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

f. the CDR-H1 comprises the sequence set forth in SEQ ID NO:16, the CDR-H2 comprises the sequence set forth in SEQ ID NO:22, the CDR-H3 comprises the sequence set forth in SEQ ID NO:35, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

g. the CDR-H1 comprises the sequence set forth in SEQ ID NO:16, the CDR-H2 comprises the sequence set forth in SEQ ID NO:23, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

h. the CDR-H1 comprises the sequence set forth in SEQ ID NO:16, the CDR-H2 comprises the sequence set forth in SEQ ID NO:19, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

i. the CDR-H1 comprises the sequence set forth in SEQ ID NO:16, the CDR-H2 comprises the sequence set forth in SEQ ID NO:24, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

j. the CDR-H1 comprises the sequence set forth in SEQ ID NO:16, the CDR-H2 comprises the sequence set forth in SEQ ID NO:22, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

k. the CDR-H1 comprises the sequence set forth in SEQ ID NO:16, the CDR-H2 comprises the sequence set forth in SEQ ID NO:25, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32; or l. the CDR-H1 comprises the sequence set forth in SEQ ID NO: 16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:29, the CDR-L2 comprises the sequence set forth in SEQ ID NO:31, and the CDR-L3 comprises the sequence set forth in SEQ ID NO:33.

In some embodiments, the peptide consists of the sequence AIFPGAVPAA (SEQ ID NO: 42). In some embodiments, the ABP binds to any one or more of amino acid positions 1-5 of the sequence AIFPGAVPAA (SEQ ID NO: 42). In some embodiments, the ABP binds to one or both of amino acid positions 4 and 5 of the sequence AIFPGAVPAA (SEQ ID NO: 42). In some embodiments, the ABP binds to any one or more of amino acid positions 45-60 of HLA subtype A*02:01. In some embodiments, the ABP binds to any one or more of amino acid positions 56, 59, 60, 63, 64, 66, 67, 70, 73, 74, 132, 150-153, 155, 156, 158-160, 162-164, 166-168, 170, and 171 of HLA subtype A*02:01.

In some embodiments, the three heavy chain CDR sequences and the three light chain CDR sequences are selected from the clones designated 05A03, 05D07, 05D10, 05G06, 06D07, 09D01, 09D04, or 09G01, and wherein the three heavy chain CDR sequences and the three light chain CDR sequences are selected from the same clone. In some embodiments:

a. the CDR-H1 comprises the sequence set forth in SEQ ID NO:16, the CDR-H2 comprises the sequence set forth in SEQ ID NO:17, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

b. the CDR-H1 comprises the sequence set forth in SEQ ID NO:16, the CDR-H2 comprises the sequence set forth in SEQ ID NO:18, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

c. the CDR-H1 comprises the sequence set forth in SEQ ID NO:16, the CDR-H2 comprises the sequence set forth in SEQ ID NO:19, the CDR-H3 comprises the sequence set forth in SEQ ID NO:34, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

d. the CDR-H1 comprises the sequence set forth in SEQ ID NO:16, the CDR-H2 comprises the sequence set forth in SEQ ID NO:20, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

e. the CDR-H1 comprises the sequence set forth in SEQ ID NO:16, the CDR-H2 comprises the sequence set forth in SEQ ID NO:19, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

f. the CDR-H1 comprises the sequence set forth in SEQ ID NO:16, the CDR-H2 comprises the sequence set forth in SEQ ID NO:22, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

g. the CDR-H1 comprises the sequence set forth in SEQ ID NO:16, the CDR-H2 comprises the sequence set forth in SEQ ID NO:25, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32; or h. the CDR-H1 comprises the sequence set forth in SEQ ID NO:16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:29, the CDR-L2 comprises the sequence set forth in SEQ ID NO:31, and the CDR-L3 comprises the sequence set forth in SEQ ID NO:33.

In some embodiments, the VH sequence comprises an N to T substitution at position 69 of the sequence shown in SEQ ID NO: 7 and/or a Y to F substitution at position 27 of the sequence shown in SEQ ID NO: 6 or 12.

In some embodiments, the VH sequence comprises any one of the sequences set forth in SEQ ID NOS:1, 3-9, 11-14, 37, 38, 39, 40, or 41.

In some embodiments, the VH sequence comprises any one of the sequences set forth in SEQ ID NOS:1, 5-7, 9, 11, 12, 14, 38, 39, 40, or 41.

In some embodiments:

a. the VH sequence comprises the sequence set forth in SEQ ID NO:1 and the VL sequence comprises the sequence set forth in SEQ ID NO:2;

b. the VH sequence comprises the sequence set forth in SEQ ID NO:3 and the VL sequence comprises the sequence set forth in SEQ ID NO:2;

c. the VH sequence comprises the sequence set forth in SEQ ID NO:4 and the VL sequence comprises the sequence set forth in SEQ ID NO:2;

d. the VH sequence comprises the sequence set forth in SEQ ID NO:5 and the VL sequence comprises the sequence set forth in SEQ ID NO:2;

e. the VH sequence comprises the sequence set forth in SEQ ID NO:6 and the VL sequence comprises the sequence set forth in SEQ ID NO:2;

f. the VH sequence comprises the sequence set forth in SEQ ID NO:7 and the VL sequence comprises the sequence set forth in SEQ ID NO:2;

g. the VH sequence comprises the sequence set forth in SEQ ID NO:8 and the VL sequence comprises the sequence set forth in SEQ ID NO:2;

h. the VH sequence comprises the sequence set forth in SEQ ID NO:9 and the VL sequence comprises the sequence set forth in SEQ ID NO:10;

i. the VH sequence comprises the sequence set forth in SEQ ID NO:11 and the VL sequence comprises the sequence set forth in SEQ ID NO:2;

j. the VH sequence comprises the sequence set forth in SEQ ID NO:12 and the VL sequence comprises the sequence set forth in SEQ ID NO:2;

k. the VH sequence comprises the sequence set forth in SEQ ID NO:13 and the VL sequence comprises the sequence set forth in SEQ ID NO:2; or l. the VH sequence comprises the sequence set forth in SEQ ID NO:14 and the VL sequence comprises the sequence set forth in SEQ ID NO:2.

In some embodiments:

a. the VH sequence comprises the sequence set forth in SEQ ID NO:1 and the VL sequence comprises the sequence set forth in SEQ ID NO:2;

b. the VH sequence comprises the sequence set forth in SEQ ID NO:5 and the VL sequence comprises the sequence set forth in SEQ ID NO:2;

c. the VH sequence comprises the sequence set forth in SEQ ID NO:6 and the VL sequence comprises the sequence set forth in SEQ ID NO:2;

d. the VH sequence comprises the sequence set forth in SEQ ID NO:7 and the VL sequence comprises the sequence set forth in SEQ ID NO:2;

e. the VH sequence comprises the sequence set forth in SEQ ID NO:9 and the VL sequence comprises the sequence set forth in SEQ ID NO:10;

f. the VH sequence comprises the sequence set forth in SEQ ID NO:11 and the VL sequence comprises the sequence set forth in SEQ ID NO:2;

g. the VH sequence comprises the sequence set forth in SEQ ID NO:12 and the VL sequence comprises the sequence set forth in SEQ ID NO:2; or h. the VH sequence comprises the sequence set forth in SEQ ID NO:14 and the VL sequence comprises the sequence set forth in SEQ ID NO:2.

In some embodiments, the antigen binding protein binds to the HLA-PEPTIDE target through at least one contact point with the HLA Class I molecule and through at least one contact point with the HLA-restricted peptide of the HLA-PEPTIDE target. In some embodiments, the peptide is an HLA-restricted peptide complexed with the HLA subtype A*02:01; wherein the HLA-restricted peptide is located in the peptide binding groove of an α1/α2 heterodimer portion of HLA subtype A*02:01; and wherein the HLA subtype A*02:01 is an HLA Class I molecule. In some embodiments, the amino acid binding positions of the ABP to the peptide or the HLA subtype A*02:01 are determined via one or more of positional scanning, hydrogen-deuterium exchange, and protein crystallography.

In some embodiments, the ABP binds greater than one antigen or greater than one epitope on a single antigen. In some embodiments, the antigen-binding site comprises an scFv fragment. In some embodiments, the antigen-binding site comprises a Fab fragment.

In some embodiments, the ABP is multispecific. In some embodiments, the ABP is bispecific or trispecific. In some embodiments, the ABP further comprises an additional antigen-binding site, and the additional antigen-binding site binds an additional antigen. In some embodiments, the antigen-binding site that binds to the HLA-peptide target is a Fab fragment, and the additional antigen-binding site is an scFv fragment. In some embodiments, the antigen-binding site that binds to the HLA-peptide target is an scFv fragment, and the additional antigen-binding site is a Fab fragment. In some embodiments, the antigen-binding site that binds to the HLA-peptide target and the additional antigen-binding site are each a Fab fragment. In some embodiments, the antigen-binding site that binds to the HLA-peptide target and the additional antigen-binding site are each an scFv fragment.

In some embodiments, the ABP comprises a first polypeptide and a second polypeptide. In some embodiments, the first polypeptide comprises, in an N→C direction, an scFv and a CH2-CH3 domain. In some embodiments, the first polypeptide comprises, in an N→C direction, an scFv, a VH domain of a Fab fragment, a CH1 domain of the Fab fragment, and a CH2-CH3 domain. In some embodiments, the first polypeptide comprises, in an N→C direction, a VH domain of a Fab fragment, a CH1 domain of the Fab fragment, and a CH2-CH3 domain. In some embodiments, the second polypeptide comprises, in an N→C direction, an scFv and a CH2-CH3 domain. In some embodiments, the second polypeptide comprises, in an N→C direction, an scFv, a VH domain of a Fab fragment, a CH1 domain of the Fab fragment, and a CH2-CH3 domain. In some embodiments, the second polypeptide comprises, in an N→C direction, an scFv, a VH domain of a Fab fragment, a CH1 domain of the Fab fragment, and a CH2-CH3 domain.

In some embodiments, the ABP further comprises a third polypeptide comprising, in an N→C direction, a VL domain of the Fab fragment of the first polypeptide and a CL domain of the Fab fragment of the first polypeptide. In some embodiments, the ABP further comprises a fourth polypeptide comprising, in an N→C direction, a VL domain of the Fab fragment of the second polypeptide and a CL domain of the Fab fragment of the second polypeptide.

In another aspect, provided herein is an isolated antigen binding protein (ABP) comprising a first scFv and a second scFv that each specifically bind a first target antigen, a Fab that specifically binds an additional target antigen that is distinct from the first target antigen, and an Fc domain, wherein the ABP comprises a first polypeptide, a second polypeptide, and a third polypeptide, wherein the first polypeptide comprises, in an N→C direction, the first scFv-CH2-CH3, wherein the second polypeptide comprises, in an N→C direction, a VH domain of the Fab-a CH1 domain of the Fab-CH2-CH3, wherein the third polypeptide comprises, in an N→C direction, a VL domain of the Fab-a CL domain of the Fab, and wherein the second scFv is attached, directly or indirectly, to the N-terminus of the second polypeptide or the third polypeptide;

wherein the first target antigen is a human leukocyte antigen (HLA)-PEPTIDE target and wherein the first and second scFvs comprise a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3, wherein:

a. the CDR-H1 comprises the sequence set forth in SEQ ID NO:16, the CDR-H2 comprises the sequence set forth in SEQ ID NO:17, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

b. the CDR-H1 comprises the sequence set forth in SEQ ID NO:16, the CDR-H2 comprises the sequence set forth in SEQ ID NO:18, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

c. the CDR-H1 comprises the sequence set forth in SEQ ID NO:16, the CDR-H2 comprises the sequence set forth in SEQ ID NO:19, the CDR-H3 comprises the sequence set forth in SEQ ID NO:34, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

d. the CDR-H1 comprises the sequence set forth in SEQ ID NO:16, the CDR-H2 comprises the sequence set forth in SEQ ID NO:20, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

e. the CDR-H1 comprises the sequence set forth in SEQ ID NO: 16, the CDR-H2 comprises the sequence set forth in SEQ ID NO:21, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

f. the CDR-H1 comprises the sequence set forth in SEQ ID NO:16, the CDR-H2 comprises the sequence set forth in SEQ ID NO:22, the CDR-H3 comprises the sequence set forth in SEQ ID NO:35, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

g. the CDR-H1 comprises the sequence set forth in SEQ ID NO:16, the CDR-H2 comprises the sequence set forth in SEQ ID NO:23, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

h. the CDR-H1 comprises the sequence set forth in SEQ ID NO:16, the CDR-H2 comprises the sequence set forth in SEQ ID NO:19, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

i. the CDR-H1 comprises the sequence set forth in SEQ ID NO:16, the CDR-H2 comprises the sequence set forth in SEQ ID NO:24, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

j. the CDR-H1 comprises the sequence set forth in SEQ ID NO:16, the CDR-H2 comprises the sequence set forth in SEQ ID NO:22, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

k. the CDR-H1 comprises the sequence set forth in SEQ ID NO:16, the CDR-H2 comprises the sequence set forth in SEQ ID NO:25, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32; or l. the CDR-H1 comprises the sequence set forth in SEQ ID NO:16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:29, the CDR-L2 comprises the sequence set forth in SEQ ID NO:31, and the CDR-L3 comprises the sequence set forth in SEQ ID NO:33.

In some embodiments, the second scFv is attached, directly or indirectly, to the N-terminus of the second polypeptide. In some embodiments, the second scFv is attached, directly or indirectly, to the N-terminus of the third polypeptide.

In another aspect, provided herein is an isolated antigen binding protein (ABP) comprising a first scFv and a second scFv that each specifically bind a first target antigen and a first Fab and a second Fab that each specifically bind an additional target antigen that is distinct from the first target antigen, wherein the ABP comprises a first polypeptide, a second polypeptide, a third polypeptide, and a fourth polypeptide, wherein the first polypeptide comprises, in an N→C direction, a VH domain of the first Fab-CH1-CH2-CH3, wherein the second polypeptide comprises, in an N→C direction, a VH domain of the second Fab-CH1-CH2-CH3, wherein the third polypeptide comprises, in an N→C direction, a VL domain of the first Fab-a CL domain of the first Fab, and wherein the fourth polypeptide comprises, in an N→C direction, a VL domain of the second Fab-a CL domain of the second Fab, and wherein the first scFv is attached, directly or indirectly, to the N-terminus of the first or third polypeptide, and wherein the second scFv is attached, directly or indirectly, to the N-terminus of the second or fourth polypeptide;

wherein the first target antigen is a human leukocyte antigen (HLA)-PEPTIDE target and wherein the first and second scFvs comprise a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3, wherein:

a. the CDR-H1 comprises the sequence set forth in SEQ ID NO:16, the CDR-H2 comprises the sequence set forth in SEQ ID NO:17, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

b. the CDR-H1 comprises the sequence set forth in SEQ ID NO:16, the CDR-H2 comprises the sequence set forth in SEQ ID NO:18, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

c. the CDR-H1 comprises the sequence set forth in SEQ ID NO:16, the CDR-H2 comprises the sequence set forth in SEQ ID NO:19, the CDR-H3 comprises the sequence set forth in SEQ ID NO:34, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

d. the CDR-H1 comprises the sequence set forth in SEQ ID NO:16, the CDR-H2 comprises the sequence set forth in SEQ ID NO:20, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

e. the CDR-H1 comprises the sequence set forth in SEQ ID NO:16, the CDR-H2 comprises the sequence set forth in SEQ ID NO:21, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

f. the CDR-H1 comprises the sequence set forth in SEQ ID NO:16, the CDR-H2 comprises the sequence set forth in SEQ ID NO:22, the CDR-H3 comprises the sequence set forth in SEQ ID NO:35, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

g. the CDR-H1 comprises the sequence set forth in SEQ ID NO:16, the CDR-H2 comprises the sequence set forth in SEQ ID NO:23, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

h. the CDR-H1 comprises the sequence set forth in SEQ ID NO:16, the CDR-H2 comprises the sequence set forth in SEQ ID NO:19, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

i. the CDR-H1 comprises the sequence set forth in SEQ ID NO:16, the CDR-H2 comprises the sequence set forth in SEQ ID NO:24, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

j. the CDR-H1 comprises the sequence set forth in SEQ ID NO:16, the CDR-H2 comprises the sequence set forth in SEQ ID NO:22, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

k. the CDR-H1 comprises the sequence set forth in SEQ ID NO:16, the CDR-H2 comprises the sequence set forth in SEQ ID NO:25, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32; or l. the CDR-H1 comprises the sequence set forth in SEQ ID NO:16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:29, the CDR-L2 comprises the sequence set forth in SEQ ID NO:31, and the CDR-L3 comprises the sequence set forth in SEQ ID NO:33.

In some embodiments:

a. the CDR-H1 comprises the sequence set forth in SEQ ID NO: 16, the CDR-H2 comprises the sequence set forth in SEQ ID NO:17, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

b. the CDR-H1 comprises the sequence set forth in SEQ ID NO:16, the CDR-H2 comprises the sequence set forth in SEQ ID NO:18, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

c. the CDR-H1 comprises the sequence set forth in SEQ ID NO:16, the CDR-H2 comprises the sequence set forth in SEQ ID NO:19, the CDR-H3 comprises the sequence set forth in SEQ ID NO:34, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

d. the CDR-H1 comprises the sequence set forth in SEQ ID NO:16, the CDR-H2 comprises the sequence set forth in SEQ ID NO:20, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

e. the CDR-H1 comprises the sequence set forth in SEQ ID NO:16, the CDR-H2 comprises the sequence set forth in SEQ ID NO:19, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

f. the CDR-H1 comprises the sequence set forth in SEQ ID NO:16, the CDR-H2 comprises the sequence set forth in SEQ ID NO:22, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32;

g. the CDR-H1 comprises the sequence set forth in SEQ ID NO:16, the CDR-H2 comprises the sequence set forth in SEQ ID NO:25, the CDR-H3 comprises the sequence set forth in SEQ ID NO:36, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32; or h. the CDR-H1 comprises the sequence set forth in SEQ ID NO:16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:29, the CDR-L2 comprises the sequence set forth in SEQ ID NO:31, and the CDR-L3 comprises the sequence set forth in SEQ ID NO:33.

In some embodiments, the VH sequence comprises any one of the sequences set forth in SEQ ID NOS:1, 3-9, and 11-14. In some embodiments, the VH sequence comprises any one of the sequences set forth in SEQ ID NOS:1, 5-7, 9, 11, 12, and 14. In some embodiments, the VL sequence the sequences set forth in SEQ ID NO:2 or SEQ ID NO:10.

In some embodiments:

a. the VH sequence comprises the sequence set forth in SEQ ID NO:1 and the VL sequence comprises the sequence set forth in SEQ ID NO:2;

b. the VH sequence comprises the sequence set forth in SEQ ID NO:3 and the VL sequence comprises the sequence set forth in SEQ ID NO:2;

c. the VH sequence comprises the sequence set forth in SEQ ID NO:4 and the VL sequence comprises the sequence set forth in SEQ ID NO:2;

d. the VH sequence comprises the sequence set forth in SEQ ID NO:5 and the VL sequence comprises the sequence set forth in SEQ ID NO:2;

e. the VH sequence comprises the sequence set forth in SEQ ID NO:6 and the VL sequence comprises the sequence set forth in SEQ ID NO:2;

f. the VH sequence comprises the sequence set forth in SEQ ID NO:7 and the VL sequence comprises the sequence set forth in SEQ ID NO:2;

g. the VH sequence comprises the sequence set forth in SEQ ID NO:8 and the VL sequence comprises the sequence set forth in SEQ ID NO:2;

h. the VH sequence comprises the sequence set forth in SEQ ID NO:9 and the VL sequence comprises the sequence set forth in SEQ ID NO:10;

i. the VH sequence comprises the sequence set forth in SEQ ID NO:11 and the VL sequence comprises the sequence set forth in SEQ ID NO:2;

j. the VH sequence comprises the sequence set forth in SEQ ID NO:12 and the VL sequence comprises the sequence set forth in SEQ ID NO:2;

k. the VH sequence comprises the sequence set forth in SEQ ID NO:13 and the VL sequence comprises the sequence set forth in SEQ ID NO:2; or l. the VH sequence comprises the sequence set forth in SEQ ID NO:14 and the VL sequence comprises the sequence set forth in SEQ ID NO:2.

In some embodiments:

a. the VH sequence comprises the sequence set forth in SEQ ID NO:1 and the VL sequence comprises the sequence set forth in SEQ ID NO:2;

b. the VH sequence comprises the sequence set forth in SEQ ID NO:5 and the VL sequence comprises the sequence set forth in SEQ ID NO:2;

c. the VH sequence comprises the sequence set forth in SEQ ID NO:6 and the VL sequence comprises the sequence set forth in SEQ ID NO:2;

d. the VH sequence comprises the sequence set forth in SEQ ID NO:7 and the VL sequence comprises the sequence set forth in SEQ ID NO:2;

e. the VH sequence comprises the sequence set forth in SEQ ID NO:9 and the VL sequence comprises the sequence set forth in SEQ ID NO:10;

f. the VH sequence comprises the sequence set forth in SEQ ID NO:11 and the VL sequence comprises the sequence set forth in SEQ ID NO:2;

g. the VH sequence comprises the sequence set forth in SEQ ID NO:12 and the VL sequence comprises the sequence set forth in SEQ ID NO:2; or h. the VH sequence comprises the sequence set forth in SEQ ID NO:14 and the VL sequence comprises the sequence set forth in SEQ ID NO:2.

In some embodiments, the first scFv and the second scFv each comprise identical CDR sequences. In some embodiments, the first scFv and the second scFv each bind the same epitope of the first target antigen. In some embodiments, the first scFv and the second scFv each comprise identical VH and VL sequences. In some embodiments, the first Fab and the second Fab each bind the additional antigen. In some embodiments, the first Fab and the second Fab each bind to the same epitope of the additional antigen. In some embodiments, the first Fab and the second Fab each comprise identical CDR sequences.

In some embodiments, the first Fab and the second Fab each comprise identical VH and VL sequences. In some embodiments, the first and second polypeptides are identical. In some embodiments, the third and fourth polypeptides are identical. In some embodiments, a sequence comprising the CH2-CH3 domains of the first polypeptide is distinct from a sequence comprising the CH2-CH3 domains of the second polypeptide.

In some embodiments, the ABP comprises a molecule selected from the group consisting of a single domain antibody, a DVD-Ig™, a DART™, a Duobody®, a CovX-Body, an Fcab antibody, a TandAb® antibody, a tandem Fab, a Zybody™, a BEAT® molecule, a diabody, a triabody, a tetrabody, a tandem diabody, and an alternative scaffold. In some embodiments, the alternative scaffold is selected from an Anticalin®, an Adnectin™, an iMab, an EETI-II/AGRP, a Kunitz domain, a thioredoxin peptide aptamer, an Affibody®, a DARPin, an Affilin, a Tetranectin, a Fynomer, and an Avimer. In some embodiments, the ABP comprises a diabody, a triabody, a tetrabody, or a tandem diabody.

In some embodiments, the additional antigen is a cell surface molecule present on a T cell or NK cell. In some embodiments, the cell surface molecule is present on a T cell. In some embodiments, the cell surface molecule is CD3, optionally CD3ε. In some embodiments, the cell surface molecule is CD16.

In some embodiments, the ABP comprises a variant Fc region. In some embodiments, the variant Fc region comprises a modification that alters an affinity of the ABP for an Fc receptor as compared to a multispecific ABP with a non-variant Fc region. In some embodiments, unfavorable but heterodimerization favorable.

In some embodiments, the ABP is selected from: a monoclonal antibody, a neutral antibody, an antagonistic antibody, an agonist antibody, a polyclonal antibody, an afucosylated antibody, a human antibody, a humanized antibody, a chimeric antibody, and a full-length antibody. In some embodiments, the ABP is a monoclonal antibody. In some embodiments, the ABP is a human antibody. In some embodiments, the ABP is a humanized antibody. In some embodiments, the ABP is a chimeric antibody.

In some embodiments, the ABP is linked to a scaffold. In some embodiments, the scaffold comprises serum albumin or an Fc region. In some embodiments, the scaffold comprises an Fc region. In some embodiments, the Fc region is a human Fc region. In some embodiments, the Fc region is an active human Fc region. In some embodiments, the Fc region is an isotype selected from: an IgG (IgG1, IgG2, IgG3 or IgG4), an IgA (IgA1 or IgA2), an IgD, an IgE, and an IgM. In some embodiments, the Fc region is an IgG and is of a subclass selected from IgG1, IgG2, IgG3, and IgG4. In some embodiments, the ABP is linked to a scaffold via a linker, optionally wherein the linker comprises a peptide linker, optionally wherein the peptide linker comprises a hinge region of a human antibody.

In some embodiments, the ABP comprises an Fv fragment, a Fab fragment, a F(ab')$_2$ fragment, a Fab' fragment, an scFv fragment, an scFv-Fc fragment, and/or a single-domain antibody or antigen binding fragment thereof. In some embodiments, the antigen binding protein comprises an scFv fragment. In some embodiments, the antigen binding protein comprises a heavy chain constant region of a class selected from IgG, IgA, IgD, IgE, and IgM. In some embodiments, a heavy chain constant region of the class human IgG and a subclass selected from IgG1, IgG4, IgG2, and IgG3.

In some embodiments, the ABP binds to HLA-peptide targets on cells at a higher affinity relative to a reference ABP. In some embodiments, the relative affinity is measured by one or more of: Meso Scale Discovery (MSD), biolayer interferometry (BLI), or surface plasmon resonance (SPR). In some embodiments, the ABP binds to the additional antigen target on an effector cell, optionally CD3, with a dissociation constant ($K_D$) less than or equal to 100 nM, as measured by FACS. In some embodiments, the ABP binds to the additional antigen target on an effector cell, optionally CD3, at a higher affinity relative to a reference ABP. In some embodiments, the effector cell is a T cell or NK cell. In some embodiments, contacting the ABP with cancer cells results in greater cytotoxicity upon contact relative to a reference ABP. In some embodiments, contacting the ABP with cancer cells results in at least 50%, 60%, 70%, 80%, 90% or 95% cytotoxicity upon contact. In some embodiments, the concentration of ABP is less than 0.1 nM or less than 1 nM. In some embodiments, the cancer cells express the HLA-peptide target on their cell surface. In some embodiments, the cancer cells are A375 cells or LN229 cells. In some embodiments, the ABP binds to the HLA-peptide target on cells with a higher antigen specificity relative to a reference ABP. In some embodiments, the antigen specificity of the ABP is at least 1, 2 or 3 fold greater than a reference ABP. In some embodiments, the antigen specificity is measured by flow cytometry.

In some embodiments, the ABP is a portion of a chimeric antigen receptor (CAR) comprising: an extracellular portion comprising the ABP and an intracellular signaling domain. In some embodiments, the ABP comprises an scFv and the intracellular signaling domain comprises an ITAM. In some embodiments, the intracellular signaling domain comprises a signaling domain of a CD3 zeta chain. In some embodiments, the ABP further comprises a transmembrane domain linking the extracellular domain and the intracellular signaling domain. In some embodiments, the ABP further comprises an intracellular signaling domain of a T cell costimulatory molecule. In some embodiments, the T cell costimulatory molecule is CD28, 4-1BB, OX-40, ICOS, or any combination thereof.

In some embodiments, the ABP described herein is for use as a medicament. In some embodiments, the ABP described herein is for use in the treatment of a cancer. In some embodiments, the cancer expresses or is predicted to express the HLA-PEPTIDE target. In some embodiments, the cancer is selected from a solid tumor and a hematological tumor.

In another aspect, provided herein is an ABP that is a conservatively modified variant of any one of the ABPs described herein.

In another aspect, provided herein is an ABP that competes for binding with any one of the ABPs described herein.

In another aspect, provided herein is an isolated polynucleotide or set of polynucleotides encoding any one of the disclosed ABPs, a VH thereof, a VL thereof, a light chain thereof, a heavy chain thereof, or an antigen-binding portion thereof; optionally cDNA.

In another aspect, provided herein is a virus comprising any one of the isolated polynucleotides or set of polynucleotides disclosed herein. In some embodiments, the virus is a filamentous phage.

In another aspect, provided herein is a yeast cell comprising any one of the isolated polynucleotides or set of polynucleotides disclosed herein.

In another aspect, provided herein is a vector or set of vectors comprising any one of the polynucleotides or set of polynucleotides disclosed herein.

In another aspect, provided herein is a host cell comprising any one of the polynucleotides or set of polynucleotides disclosed herein or any one of the vectors or set of vectors disclosed herein. In some embodiments, the host cell does not comprise endogenous major histocompatibility complex (MHC). In some embodiments, the host cell comprises exogenous HLA. In some embodiments, the host cell is CHO, HEK293, K-562 or A375 cell. In some embodiments, the host cell is a T cell. In some embodiments, the host cell is a cultured cell from a tumor cell line. In some embodiments, the tumor cell line is selected from the group consisting of HCC-1599, NCI-H510A, A375, LN229, NCI-H358, ZR-75-1, MS751, OE19, MOR, BV173, MCF-7, NCI-H82, Colo829, and NCI-H146.

In another aspect, provided herein is a cell culture system comprising a host cell as disclosed herein and a cell culture medium.

In another aspect, provided herein is an engineered cell expressing a receptor comprising any one of the ABPs disclosed herein. In some embodiments, the engineered cell is a T cell, optionally a cytotoxic T cell (CTL). In some embodiments, the ABP is expressed from a heterologous promoter In another aspect, provided herein is a method of producing an antigen binding protein (ABP) comprising expressing the ABP within a host cell as disclosed herein and isolating the expressed ABP.

In another aspect, provided herein is a pharmaceutical composition comprising any one of the ABPs disclosed herein and a pharmaceutically acceptable excipient.

In another aspect, provided herein is a kit comprising any one of the ABPs disclosed herein or a pharmaceutical composition as disclosed herein and instructions for use.

In another aspect, provided herein is a method of treating a disease in a subject, comprising administering to the subject an effective amount of any one of the ABPs as disclosed herein or a pharmaceutical composition as disclosed herein. In some embodiments, the disease is cancer, optionally wherein the cancer is selected from a solid tumor and a hematological tumor. In some embodiments, the cancer expresses or is predicted to express the HLA-PEPTIDE target.

BRIEF DESCRIPTION OF DRAWINGS

These and other features, aspects, and advantages of the present invention will become better understood with regard to the following description, and accompanying drawings, where:

FIG. 11A shows the cytotoxicity of Format 41 diabody against control cells. FIG. 11B shows the cytotoxicity against target-expressing cells.

DETAILED DESCRIPTION

Figure 1:
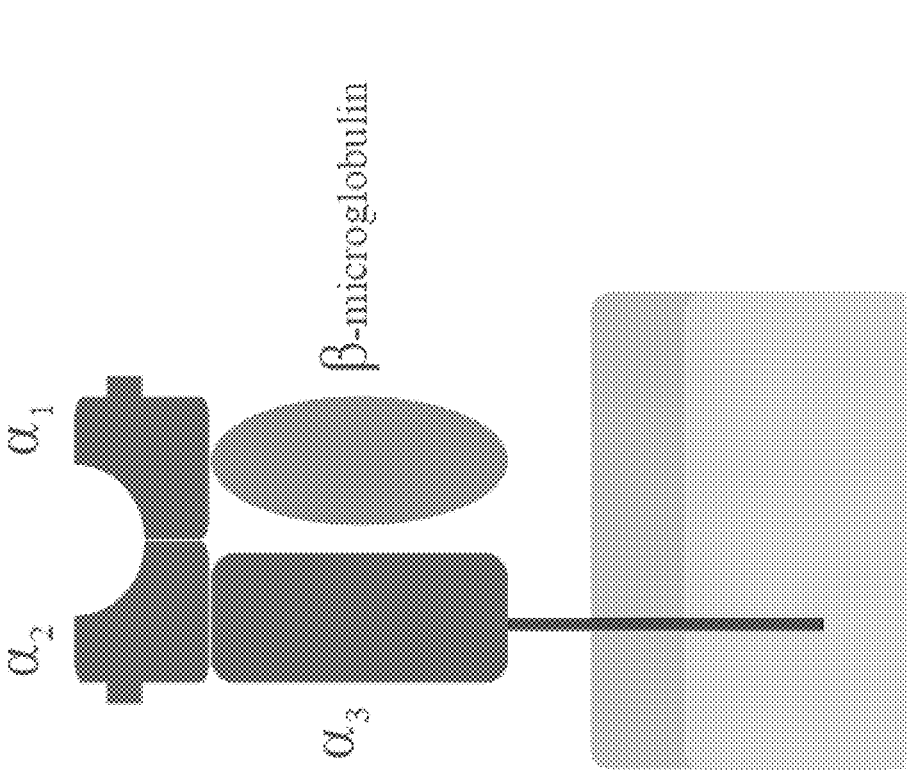
FIG. 1 shows the general structure of a Human Leukocyte Antigen (HLA) Class I molecule. By User atropos235 on en.wikipedia-Own work, CC BY 2.5, which can be found at the website located at: commons.wikimedia.org/w/index-.php?curid=1805424.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise. For example, an antigen binding protein (ABP) "comprising a variable heavy chain sequence"

includes an ABP "consisting of a variable heavy chain sequence" and an ABP "consisting essentially of a variable heavy chain sequence."

The term "about" or "approximately" indicates and encompasses an indicated value and a range above and below that value. In certain embodiments, the term "about" indicates the designated value±20%, ±10%, ±5%, or ±1%. In certain embodiments, where applicable, the term "about" indicates the designated value(s)±one standard deviation of that value(s). In some embodiments, the term "about" refers to values that are within an acceptable error range for the particular value as determined by one of ordinary skill in the art, which will depend in part on how the value is measured or determined, e.g., the limitations of the measurement system. Alternatively, particularly with respect to biological systems or processes, the term can indicate within an order of magnitude, within 5-fold, or within 2-fold, of a value. Where particular values are described in the application and claims, unless otherwise stated, the term "about" referring to within an acceptable error range for the particular value can be assumed. Also, where ranges and/or subranges of values are provided, the ranges and/or subranges can include the endpoints of the ranges and/or subranges.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antigen binding protein" or "ABP" is used herein in its broadest sense and includes certain types of molecules comprising one or more antigen-binding domains, each of which can specifically bind to an antigen or epitope.

In some embodiments, the ABP comprises an antibody. In some embodiments, the ABP consists of an antibody. In some embodiments, the ABP consists essentially of an antibody. An ABP specifically includes intact antibodies (e.g., intact immunoglobulins), antibody fragments, ABP fragments, and multispecific antibodies. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment. In some embodiments, a chimeric antigen receptor (CAR) comprises an ABP as disclosed herein. An "HLA-PEPTIDE ABP," "anti-HLA-PEPTIDE ABP," or "HLA-PEPTIDE-specific ABP" is an ABP, as provided herein, which specifically binds to the antigen HLA-PEPTIDE. An ABP includes proteins comprising one or more antigen-binding domains that specifically bind to an antigen or epitope via a variable region, such as a variable region derived from a B cell (e.g., antibody) or T cell (e.g., TCR).

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain (VH) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., trispecific, bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

As used herein, "variable region" refers to a variable nucleotide sequence that arises from a recombination event, for example, it can include a V, J, and/or D region of an immunoglobulin or T cell receptor (TCR) sequence from a B cell or T cell, such as an activated T cell or an activated B cell.

The term "antigen-binding site" refers to the portion of an ABP that is capable of specifically binding to an antigen or epitope. One example of an antigen-binding site is an antigen-binding site formed by an antibody $V_H$-$V_L$ dimer of an ABP. Another example of an antigen-binding site is an antigen-binding site formed by diversification of certain loops from the tenth fibronectin type III domain of an Adnectin. An antigen-binding site can include antibody CDRs 1, 2, and 3 from a heavy chain in that order; and antibody CDRs 1, 2, and 3 from a light chain in that order.

The antibody VH and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three antibody CDRs and four FRs, arranged in the following order (from N-terminus to C-terminus): FR1-CDR1-FR2-CDR2-FR3-CDR3-FR4. The antibody CDRs are involved in antigen binding, and influence antigen specificity and binding affinity of the ABP. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of an antibody CDR can be determined by one of skill in the art using any of a number of known numbering schemes, including those described by Kabat et al., supra ("Kabat" numbering scheme): Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-

77 ("IMGT" numbering scheme); and Honegge and Pluckthun, *J. Mol. Biol.*, 2001, 309:657-70 ("AHo" numbering scheme); each of which is incorporated by reference in its entirety.

Table 20 provides the positions of antibody CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

Antibody CDRs may be assigned, for example, using ABP numbering software, such as Abnum, available at www.bioinf.org.uk/abs/abnum/, and described in Abhinandan and Martin, *Immunology*, 2008, 45:3832-3839, incorporated by reference in its entirety.

TABLE 20

| Residues in CDRs according to Kabat and Chothia numbering schemes | | |
|---|---|---|
| CDR | Kabat | Chothia |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an ABP heavy chain constant region (e.g., as reported in Kabat et al., supra). Unless stated otherwise, the EU numbering scheme is used to refer to residues in ABP heavy chain constant regions described herein.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

An "ABP fragment" comprises a portion of an intact ABP, such as the antigen-binding or variable region of an intact ABP. ABP fragments include, for example, Fv fragments, Fab fragments, F(ab')₂ fragments, Fab' fragments, scFv (sFv) fragments, and scFv-Fc fragments. ABP fragments include antibody fragments. Antibody fragments can include Fv fragments, Fab fragments, F(ab')₂ fragments, Fab' fragments, scFv (sFv) fragments, scFv-Fc fragments, and TCR fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (CH1) of the heavy chain. Fab fragments may be generated, for example, by recombinant methods or by papain digestion of a full-length ABP.

"F(ab')₂" fragments contain two Fab' fragments joined, near the hinge region, by disulfide bonds. F(ab')₂ fragments may be generated, for example, by recombinant methods or by pepsin digestion of an intact ABP. The F(ab') fragments can be dissociated, for example, by treatment with ß-mercaptoethanol.

"Single-chain Fv" or "sFv" or "scFv" fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a $(GGGGS)_n$ (SEQ ID NO: 43). In some embodiments, n=1, 2, 3, 4, 5, or 6. See ABPs from *Escherichia coli*. In Rosenberg M. & Moore G. P. (Eds.), *The Pharmacology of Monoclonal ABPs* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" refers to a molecule in which one variable domain of an ABP specifically binds to an antigen without the presence of the other variable domain. Single domain ABPs, and fragments thereof, are described in Arabi Ghahroudi et al., *FEBS Letters,* 1998, 414:521-526 and Muyldermans et al., *Trends in Biochem. Sci.,* 2001, 26:230-245, each of which is incorporated by reference in its entirety. Single domain ABPs are also known as sdAbs or nanobodies.

The term "Fc region" or "Fc" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.,* 2010, 125:S41-52, incorporated by reference in its entirety. The Fc region may be a naturally occurring Fc region, or an Fc region modified as described in the art or elsewhere in this disclosure.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an ABP. Exemplary alternative scaffolds include those derived from fibronectin (e.g., Adnectins™), the β-sandwich (e.g., iMab), lipocalin (e.g., Anticalins®), EETI-II/AGRP, BPTI/LACI-DI/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD₃ (e.g., Tetranectins), Fynomers, and (LDLR-A module) (e.g., Avimers). Additional information on alternative scaffolds is provided in Binz et al., *Nat. Biotechnol.,* 2005 23:1257-1268; Skerra, *Current Opin. in Biotech.,* 2007 18:295-304; and Silacci et al., *J. Biol. Chem.,* 2014, 289:14392-14398; each of which is incorporated by reference in its entirety. An alternative scaffold is one type of ABP.

A "multispecific ABP" is an ABP that comprises two or more different antigen-binding domains that collectively specifically bind two or more different epitopes. The two or more different epitopes may be epitopes on the same antigen (e.g., a single HLA-PEPTIDE molecule expressed by a cell) or on different antigens (e.g., different HLA-PEPTIDE molecules expressed by the same cell, or a HLA-PEPTIDE molecule and a non-HLA-PEPTIDE molecule). In some aspects, a multispecific ABP binds two different epitopes (i.e., a "bispecific ABP"). In some aspects, a multispecific ABP binds three different epitopes (i.e., a "trispecific ABP").

A "monospecific ABP" is an ABP that comprises one or more binding sites that specifically bind to a single epitope. An example of a monospecific ABP is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., Nature, 1986, 321:522-525; Riechmann et al., Nature, 1988, 332:323-329; and Presta, Curr. Op. Struct. Biol., 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

"Reference ABP" refers to an ABP having all the heavy chain and light chain CDRs of the Parent A clone. In certain embodiments, a reference ABP is an ABP comprising an antigen-binding site comprising a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3, wherein the CDR-H1 comprises the sequence set forth in SEQ ID NO:16, the CDR-H2 comprises the sequence set forth in SEQ ID NO:26, the CDR-H3 comprises the sequence set forth in SEQ ID NO:27, the CDR-L1 comprises the sequence set forth in SEQ ID NO:28, the CDR-L2 comprises the sequence set forth in SEQ ID NO:30, and the CDR-L3 comprises the sequence set forth in SEQ ID NO:32. "Reference ABP" can also refer to an ABP having the VH and VL sequences of the Parent A clone. In certain embodiments, a reference ABP is an ABP comprising a VH sequence and a VL sequence, wherein the VH sequence comprises the sequence set forth in SEQ ID NO:15 and the VL sequence comprises the sequence set forth in SEQ ID NO:2. In certain embodiments, "Reference ABP" is used to describe an antibody identical to an ABP as described or claimed herein, except that it has a set of heavy and light chain CDRs or VH and VL sequences differing from the affinity matured clones described herein.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule. In some aspects, the affinity of a HLA-PEPTIDE ABP for a non-target molecule is less than about 50% of the affinity for HLA-PEPTIDE. In some aspects, the affinity of a HLA-PEPTIDE ABP for a non-target molecule is less than about 40% of the affinity for HLA-PEPTIDE. In some aspects, the affinity of a HLA-PEPTIDE ABP for a non-target molecule is less than about 30% of the affinity for HLA-PEPTIDE. In some aspects, the affinity of a HLA-PEPTIDE ABP for a non-target molecule is less than about 20% of the affinity for HLA-PEPTIDE. In some aspects, the affinity of a HLA-PEPTIDE ABP for a non-target molecule is less than about 10% of the affinity for HLA-PEPTIDE. In some aspects, the affinity of a HLA-PEPTIDE ABP for a non-target molecule is less than about 1% of the affinity for HLA-PEPTIDE. In some aspects, the affinity of a HLA-PEPTIDE ABP for a non-target molecule is less than about 0.1% of the affinity for HLA-PEPTIDE.

The term "$k_d$" ($sec^{-1}$), as used herein, refers to the dissociation rate constant of a particular ABP-antigen interaction. This value is also referred to as the $k_{off}$ value.

The term "$k_a$" ($M^{-1} \times sec^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D=k_d/k_a$. In some embodiments, the affinity of an ABP is described in terms of the $K_D$ for an interaction between such ABP and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular ABP-antigen interaction. $K_A=k_a/k_d$.

An "immunoconjugate" is an ABP conjugated to one or more heterologous molecule(s), such as a therapeutic (cytokine, for example) or diagnostic agent.

"Fc effector functions" refer to those biological activities mediated by the Fc region of an ABP having an Fc region, which activities may vary depending on isotype. Examples of ABP effector functions include C1q binding to activate complement dependent cytotoxicity (CDC), Fc receptor binding to activate ABP-dependent cellular cytotoxicity (ADCC), and ABP dependent cellular phagocytosis (ADCP).

When used herein in the context of two or more ABPs, the term "competes with" or "cross-competes with" indicates that the two or more ABPs compete for binding to an antigen (e.g., HLA-PEPTIDE). In one exemplary assay, HLA-PEPTIDE is coated on a surface and contacted with a first HLA-PEPTIDE ABP, after which a second HLA-PEPTIDE ABP is added. In another exemplary assay, a first HLA-PEPTIDE ABP is coated on a surface and contacted with HLA-PEPTIDE, and then a second HLA-PEPTIDE ABP is added. If the presence of the first HLA-PEPTIDE ABP reduces binding of the second HLA-PEPTIDE ABP, in either assay, then the ABPs compete with each other. The term "competes with" also includes combinations of ABPs where one ABP reduces binding of another ABP, but where no competition is observed when the ABPs are added in the reverse order. However, in some embodiments, the first and second ABPs inhibit binding of each other, regardless of the order in which they are added. In some embodiments, one ABP reduces binding of another ABP to its antigen by at least 25%, at least 50%, at least 60%, at least 70%, at least 80%, at least 85%, at least 90%, or at least 95%. A skilled artisan can select the concentrations of the ABPs used in the competition assays based on the affinities of the ABPs for HLA-PEPTIDE and the valency of the ABPs. The assays described in this definition are illustrative, and a skilled artisan can utilize any suitable assay to determine if ABPs compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen that specifically binds to an ABP. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an ABP binds can be determined using known techniques for epitope determination such as, for example, testing for ABP binding to HLA-PEPTIDE variants with different point-mutations, or to chimeric HLA-PEPTIDE variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 21-23 are, in some embodiments, considered conservative substitutions for one another.

TABLE 21

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 22

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 23

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular*

*Properties* 2nd ed. (1993) W. H. Freeman & Co., New York, NY. An ABP generated by making one or more conservative substitutions of amino acid residues in a parent ABP is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an ABP or pharmaceutical composition provided herein that, when administered to a subject, is effective to treat a disease or disorder.

As used herein, the term "subject" refers to a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an ABP provided herein. In some aspects, the disease or condition is a cancer. In some aspects, the disease or condition is a viral infection or chronic viral infection.

The terms "instructions for use" and "package insert," as used herein, are used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

The terms "nucleic acids" and "polynucleotides" may be used interchangeably herein to refer to polymeric forms of nucleotides of any length, either deoxyribonucleotides or ribonucleotides, or analogs thereof. Polynucleotides can include, but are not limited to coding or non-coding regions of a gene or gene fragment, loci (locus) defined from linkage analysis, exons, introns, messenger RNA (mRNA), cDNA, recombinant polynucleotides, branched polynucleotides, plasmids, vectors, isolated DNA, isolated RNA, nucleic acid probes, and primers. A polynucleotide may comprise modified nucleotides, such as methylated nucleotides and nucleotide analogs. Exemplary modified nucleotides include, e.g., 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthioN6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

Isolated HLA-Peptide Targets

The major histocompatibility complex (MHC) is a complex of antigens encoded by a group of linked loci, which are collectively termed H-2 in the mouse and HLA in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against class I glycoproteins, while helper T-cells respond mainly against class II glycoproteins.

Human major histocompatibility complex (MHC) class I molecules, referred to interchangeably herein as HLA Class I molecules, are expressed on the surface of nearly all cells. These molecules function in presenting peptides which are mainly derived from endogenously synthesized proteins to, e.g., CD8+ T cells via an interaction with the alpha-beta T-cell receptor. The class I MHC molecule comprises a heterodimer composed of a 46-kDa a chain which is non-covalently associated with the 12-kDa light chain beta-2 microglobulin. The a chain generally comprises α1 and α2 domains which form a groove for presenting an HLA-restricted peptide, and an α3 plasma membrane-spanning domain which interacts with the CD8 co-receptor of T-cells. FIG. 1 (prior art) depicts the general structure of a Class I HLA molecule. Some TCRs can bind MHC class I independently of CD8 coreceptor (see, e.g., Kerry S E, Buslepp J, Cramer L A, et al. Interplay between TCR Affinity and Necessity of Coreceptor Ligation: High-Affinity Peptide-MHC/TCR Interaction Overcomes Lack of CD8 Engagement. Journal of immunology (Baltimore, Md: 1950). 2003; 171(9):4493-4503.)

Class I MHC-restricted peptides (also referred to interchangeably herein as HLA-restricted antigens, HLA-restricted peptides, MHC-restricted antigens, restricted peptides, or peptides) generally bind to the heavy chain alpha1-alpha2 groove via about two or three anchor residues that interact with corresponding binding pockets in the MHC molecule. The beta-2 microglobulin chain plays an important role in MHC class I intracellular transport, peptide binding, and conformational stability. For most class I molecules, the formation of a heterotrimeric complex of the MHC class I heavy chain, peptide (self, non-self, and/or antigenic) and beta-2 microglobulin leads to protein maturation and export to the cell-surface.

Binding of a given HLA subtype to an HLA-restricted peptide forms a complex with a unique and novel surface that can be specifically recognized by an ABP such as, e.g., a TCR on a T cell or an antibody or antigen-binding fragment thereof. HLA complexed with an HLA-restricted peptide is referred to herein as an HLA-PEPTIDE or HLA-PEPTIDE target. In some cases the restricted peptide is located in the α1/α2 groove of the HLA molecule. In some cases the restricted peptide is bound to the α1/α2 groove of the HLA molecule via about two or three anchor residues that interact with corresponding binding pockets in the HLA molecule.

In some embodiments, the HLA-PEPTIDE targets may comprise a specific HLA-restricted peptide having a defined amino acid sequence complexed with a specific HLA subtype.

HLA-PEPTIDE targets are useful for cancer immunotherapy. In some embodiments, HLA-PEPTIDE targets are presented on the surface of a tumor cell. The HLA-PEPTIDE targets identified herein may be expressed by tumor cells in a human subject. The HLA-PEPTIDE targets identified herein may be expressed by tumor cells in a population of human subjects. For example, the HLA-PEPTIDE targets may be shared antigens that are commonly expressed in a population of human subjects with cancer.

The HLA-PEPTIDE targets identified herein may have a prevalence with an individual tumor type. The prevalence with an individual tumor type may be about 0.1%, 0.2%, 0.3%, 0.4%, 0.5%, 0.6%, 0.7%, 0.8%, 0.9%, 1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The prevalence with an individual tumor type may be about 0.1%-100%, 0.2-50%, 0.5-25%, or 1-10%.

Preferably, HLA-PEPTIDE targets are not generally expressed in most normal tissues. For example, the HLA-PEPTIDE targets may in some cases not be expressed in tissues in the Genotype-Tissue Expression (GTEx) Project, or may in some cases be expressed only in immune privileged or non-essential tissues. Exemplary immune privileged or non-essential tissues include testis, minor salivary glands, the endocervix, and the thyroid. In some cases, an HLA-PEPTIDE target may be deemed to not be expressed on essential tissues or non-immune privileged tissues if the median expression of a gene from which the restricted peptide is derived is less than 0.5 RPKM (Reads Per Kilobase of transcript per Million napped reads) across GTEx samples, if the gene is not expressed with greater than 10 RPKM across GTEx samples, if the gene was expressed at >=5 RPKM in no more than two samples across all essential tissue samples, or any combination thereof.

Exemplary HLA Class I Subtypes of the HLA-PEPTIDE Targets

In humans, there are many MHC haplotypes (referred to interchangeably herein as MHC subtypes, HLA subtypes, MHC types, and HLA types). Exemplary HLA subtypes include, by way of example only, HLA-A*01:01, HLA-A*02:01, HLA-A*02:03, HLA-A*02:04, HLA-A*02:07, HLA-A*03:01, HLA-A*03:02, HLA-A*11:01, HLA-A*23:01, HLA-A*24:02, HLA-A*25:01, HLA-A*26:01, HLA-A*29:02, HLA-A*30:01, HLA-A*30:02, HLA-A*31:01, HLA-A*32:01, HLA-A*33:01, HLA-A*33:03, HLA-A*68:01, HLA-A*68:02, HLA-B*07:02, HLA-B*08:01, HLA-B*13:02, HLA-B*15:01, HLA-B*15:03, HLA-B*18:01, HLA-B*27:02, HLA-B*27:05, HLA-B*35:01, HLA-B*35:03, HLA-B*37:01, HLA-B*38:01, HLA-B*39:01, HLA-B*40:01, HLA-B*40:02, HLA-B*44:02, HLA-B*44:03, HLA-B*46:01, HLA-B*49:01, HLA-B*51:01, HLA-B*54:01, HLA-B*55:01, HLA-B*56:01, HLA-B*57:01, HLA-B*58:01, HLA-C*01:02, HLA-C*02:02, HLA-C*03:03, HLA-C*03:04, HLA-C*04:01, HLA-C*05:01, HLA-C*06:02, HLA-C*07:01, HLA-C*07:02, HLA-C*07:04, HLA-C*07:06, HLA-C*12:03, HLA-C*14:02, HLA-C*16:01, HLA-C*16:02, HLA-C*16:04, and all subtypes thereof, including, e.g., 4 digit, 6 digit, and 8 digit subtypes. As is known to those skilled in the art there are allelic variants of the above HLA types. A full list of HLA Class Alleles can be found at the website located at: hla.alleles.org/alleles/on-http://hla.alleles.org/alleles/. For example, a full list of HLA Class I Alleles can be found at the website located at: hla.alleles.org/alleles/class1.html.

In certain embodiments, the HLA-PEPTIDE contemplated herein comprises an HLA Class I molecule and its HLA subtype is HLA subtype A*02:01.

HLA-Restricted Peptides

The HLA-restricted peptides (referred to interchangeably herein as "restricted peptides") can be peptide fragments of tumor-specific genes, e.g., cancer-specific genes. Preferably, the cancer-specific genes are expressed in cancer samples. Genes which are aberrantly expressed in cancer samples can be identified through a database. Exemplary databases include, by way of example only, The Cancer Genome Atlas (TCGA) Research Network, which can be found at the website located at: cancergenome.nih.gov/; the International Cancer Genome Consortium, which can be found at the website located at: dcc.icqc.org/. In some embodiments, the cancer-specific gene has an observed expression of at least 10 RPKM in at least 5 samples from the TCGA database. The cancer-specific gene may have an observable bimodal distribution.

The cancer-specific gene may have an observed expression of greater than 10, 20, 30, 40, 50, 60, 70, 80, 90, or 100 transcripts per million (TPM) in at least one TCGA tumor tissue. In preferred embodiments, the cancer-specific gene has an observed expression of greater than 100 TPM in at least one TCGA tumor tissue. In some cases, the cancer specific gene has an observed bimodal distribution of expression across TCGA samples. Without wishing to be bound by theory, such bimodal expression pattern is consistent with a biological model in which there is minimal expression at baseline in all tumor samples and higher expression in a subset of tumors experiencing epigenetic dysregulation.

Preferably, the cancer-specific gene is not generally expressed in most normal tissues. For example, the cancer-specific gene may in some cases not be expressed in tissues in the Genotype-Tissue Expression (GTEx) Project, or may in some cases be expressed in immune privileged or non-essential tissues. Exemplary immune privileged or non-essential tissues include testis, minor salivary glands, the endocervix, and thyroid. In some cases, a cancer-specific gene may be deemed to not be expressed in an essential tissue or non-immune privileged tissue if the median expression of the cancer-specific gene is less than 0.5 RPKM (Reads Per Kilobase of transcript per Million napped reads) across GTEx samples, if the gene is not expressed with greater than 10 RPKM across GTEx samples, if the gene is expressed at >=5 RPKM in no more than two samples across all essential tissue samples, or any combination thereof.

In some embodiments, the cancer-specific gene meets the following criteria by assessment of the GTEx: (1) median GTEx expression in brain, heart, or lung is less than 0.1 transcripts per million (TPM), with no one sample exceeding 5 TPM, (2) median GTEx expression in other essential organs (excluding testis, thyroid, minor salivary gland) is less than 2 TPM with no one sample exceeding 10 TPM.

In some embodiments, the cancer-specific gene is not likely expressed in immune cells generally, e.g., is not an interferon family gene, is not an eye-related gene, not an olfactory or taste receptor gene, and is not a gene related to the circadian cycle (e.g., not a CLOCK, PERIOD, CRY gene)

The restricted peptide preferably may be presented on the surface of a tumor.

The restricted peptides may have a size of about 5, about 6, about 7, about 8, about 9, about 10, about 11, about 12, about 13, about 14, or about 15 amino molecule residues, and any range derivable therein. In particular embodiments, the restricted peptide has a size of about 8, about 9, about 10, about 11, or about 12 amino molecule residues. The restricted peptide may be about 5-15 amino acids in length, preferably may be about 7-12 amino acids in length, or more preferably may be about 8-11 amino acids in length.

In certain embodiments, the HLA-PEPTIDE comprises an HLA-restricted peptide that comprises the sequence AIFP-GAVPAA (SEQ ID NO: 42).

Exemplary HLA-PEPTIDE Targets

Exemplary HLA-PEPTIDE targets are shown in Table A (see U.S. Application No. 62/611,403 and International Application No. PCT/US2018/067931, each of which is hereby incorporated in its entirety). In each row of Table A, the HLA allele and corresponding HLA-restricted peptide sequence of each complex is shown.

In certain embodiments, the HLA-PEPTIDE target comprises an HLA Class I molecule and an HLA-restricted peptide, wherein the HLA Class I molecule is HLA subtype A*02:01 and the HLA-restricted peptide comprises the sequence AIFPGAVPAA (SEQ ID NO: 42). In certain embodiments, in the HLA-PEPTIDE target, the peptide is an HLA-restricted peptide complexed with the HLA subtype A*02:01; wherein the HLA-restricted peptide is located in the peptide binding groove of an $\alpha 1/\alpha 2$ heterodimer portion of HLA subtype A*02:01. As shown in Table A, the HLA-restricted peptide comprising the sequence AIFPGAVPAA (SEQ ID NO: 42) can be from the FOXE1 gene (gene ID: ENSG00000178919).

HLA Class I molecules which do not associate with a restricted peptide ligand are generally unstable. Accordingly, the association of the restricted peptide with the $\alpha 1/\alpha 2$ groove of the HLA molecule may stabilize the non-covalent association of the $\beta 2$-microglobulin subunit of the HLA subtype with the $\alpha$-subunit of the HLA subtype.

Stability of the non-covalent association of the $\beta 2$-microglobulin subunit of the HLA subtype with the $\alpha$-subunit of the HLA subtype can be determined using any suitable means. For example, such stability may be assessed by dissolving insoluble aggregates of HLA molecules in high concentrations of urea (e.g., about 8M urea), and determining the ability of the HLA molecule to refold in the presence of the restricted peptide during urea removal, e.g., urea removal by dialysis. Such refolding approaches are described in, e.g., Proc. Natl. Acad. Sci. USA Vol. 89, pp. 3429-3433 April 1992, hereby incorporated by reference.

For other example, such stability may be assessed using conditional HLA Class I ligands. Conditional HLA Class I ligands are generally designed as short restricted peptides which stabilize the association of the $\beta 2$ and $\alpha$ subunits of the HLA Class I molecule by binding to the $\alpha 1/\alpha 2$ groove of the HLA molecule, and which contain one or more amino acid modifications allowing cleavage of the restricted peptide upon exposure to a conditional stimulus. Upon cleavage of the conditional ligand, the $\beta 2$ and $\alpha$-subunits of the HLA molecule dissociate, unless such conditional ligand is exchanged for a restricted peptide which binds to the $\alpha 1/\alpha 2$ groove and stabilizes the HLA molecule. Conditional ligands can be designed by introducing amino acid modifications in either known HLA peptide ligands or in predicted high-affinity HLA peptide ligands. For HLA alleles for which structural information is available, water-accessibility of side chains may also be used to select positions for introduction of the amino acid modifications. Use of conditional HLA ligands may be advantageous by allowing the batch preparation of stable HLA-peptide complexes which may be used to interrogate test restricted peptides in a high throughput manner. Conditional HLA Class I ligands, and methods of production, are described in, e.g., *Proc Natl Acad Sci USA*. 2008 Mar. 11; 105(10): 3831-3836; *Proc Natl Acad Sci USA*. 2008 Mar. 11; 105(10): 3825-3830; *J Exp Med*. 2018 May 7; 215(5): 1493-1504; Choo, J. A. L. et al. Bioorthogonal cleavage and exchange of major histocompatibility complex ligands by employing azobenzene-containing peptides. *Angew Chem Int Ed Engl* 53, 13390-13394 (2014); Amore, A. et al. Development of a Hypersensitive Periodate-Cleavable Amino Acid that is Methionine- and Disulfide-Compatible and its Application in MHC Exchange Reagents for T Cell Characterisation. *ChemBioChem* 14, 123-131 (2012); Rodenko, B. et al. Class I Major Histocompatibility Complexes Loaded by a Periodate Trigger. J Am Chem Soc 131, 12305-12313 (2009); and Chang, C. X. L. et al. Conditional ligands for Asian HLA variants facilitate the definition of CD8+ T-cell responses in acute and chronic viral diseases. Eur J Immunol 43, 1109-1120 (2013). These references are incorporated by reference in their entirety.

The ability of an HLA-restricted peptide, as described herein, to stabilize the association of the β2- and α-subunits of the HLA molecule, is assessed by performing a conditional ligand mediated-exchange reaction and assay for HLA stability. HLA stability can be assayed using any suitable method, including, e.g., mass spectrometry analysis, immunoassays (e.g., ELISA), size exclusion chromatography, and HLA multimer staining followed by flow cytometry assessment of T cells.

Other exemplary methods for assessing stability of the non-covalent association of the β2-microglobulin subunit of the HLA subtype with the α-subunit of the HLA subtype include peptide exchange using dipeptides. Peptide exchange using dipeptides has been described in, e.g., Proc Natl Acad Sci USA. 2013 Sep. 17, 110(38):15383-8; Proc Natl Acad Sci USA. 2015 Jan. 6, 112(1):202-7, which is hereby incorporated by reference.

HLA-Peptide ABPs

Provided herein are ABPs that specifically bind to an HLA-PEPTIDE target as disclosed herein. The ABPs of the present disclosure were affinity matured from the ABP G8-1B03 (also referred to as Parent A), which specifically binds to an HLA-PEPTIDE target comprising HLA subtype A*02:01 complexed with an HLA-restricted peptide comprising the sequence AIFPGAVPAA (SEQ ID NO: 42). The ABP can specifically bind to the HLA-PEPTIDE target, wherein the HLA-PEPTIDE target comprises an HLA-restricted peptide comprising the sequence AIFPGAVPAA (SEQ ID NO: 42) complexed with an HLA Class I molecule of HLA subtype A*02:01, wherein the HLA-restricted peptide is located in the peptide binding groove of an α1/α2 heterodimer portion of the HLA Class I molecule. These ABPs are also referred to as ABPs specific for "A*02:01_AIFPGAVPAA (SEQ ID NO: 42)".

The HLA-PEPTIDE target can be expressed on the surface of any suitable target cell including a tumor cell.

In some aspects, the ABP does not bind HLA class I in the absence of HLA-restricted peptide. In some aspects, the ABP does not bind HLA-restricted peptide in the absence of human MHC class I. In some aspects, the ABP binds tumor cells presenting human MHC class I being complexed with HLA-restricted peptide, optionally wherein the HLA restricted peptide is a tumor antigen characterizing the cancer.

The ABP described herein is capable of specifically binding a complex comprising HLA and an HLA-restricted peptide (HLA-PEPTIDE), e.g., derived from a tumor. In some aspects, the ABP does not bind HLA in the absence of the HLA-restricted peptide derived from the tumor. In some aspects, the ABP does not bind the HLA-restricted peptide derived from the tumor in an absence of the HLA Class I molecule. In some aspects, the ABP binds a complex comprising the HLA Class I molecule and the HLA-restricted peptide when naturally presented on a cell such as a tumor cell.

In some embodiments, an ABP provided herein modulates binding of HLA-PEPTIDE to one or more ligands of HLA-PEPTIDE.

In more particular embodiments, the ABP specifically binds to an HLA-PEPTIDE target comprising HLA subtype A*02:01 complexed with an HLA-restricted peptide comprising the sequence AIFPGAVPAA (SEQ ID NO: 42). In more particular embodiments, the ABP specifically binds to an HLA-PEPTIDE target comprising HLA subtype A*02:01 complexed with an HLA-restricted peptide consisting essentially of the sequence AIFPGAVPAA (SEQ ID NO: 42). In yet more particular embodiments, the ABP specifically binds to an HLA-PEPTIDE target comprising HLA subtype A*02:01 complexed with an HLA-restricted peptide consisting of the sequence AIFPGAVPAA (SEQ ID NO: 42).

In some embodiments, an ABP is an ABP that competes with an illustrative ABP provided herein. In some aspects, the ABP that competes with the illustrative ABP provided herein binds the same epitope as an illustrative ABP provided herein.

The ABPs provided herein can be referred to herein as "variants" of a G8-1B03 (Parent A) clone. In some embodiments, the variants are derived from the Parent A antibody clones by affinity maturation. In some embodiments, the ABPs provided herein can be derived from Parent A antibody clone using site directed mutagenesis, random mutagenesis, or any other method known in the art or described herein. In some embodiments, such variants are not derived from a sequence provided herein and may, for example, be isolated de novo according to the methods provided herein for obtaining ABPs. In some embodiments, a variant is derived from any of the sequences provided herein, wherein one or more conservative amino acid substitutions are made. In some embodiments, a variant is derived from any of the sequences provided herein, wherein one or more nonconservative amino acid substitutions are made. Conservative amino acid substitutions are described herein. Exemplary nonconservative amino acid substitutions include those described in J Immunol. 2008 May 1; 180(9):6116-31, which is hereby incorporated by reference in its entirety. In preferred embodiments, the non-conservative amino acid substitution does not interfere with or inhibit the biological activity of the functional variant. In yet more preferred embodiments, the non-conservative amino acid substitution enhances the biological activity of the functional variant, such that the biological activity of the functional variant is increased as compared to the parent A clone.

In certain embodiments, the variant ABPs provided herein exhibit the same biological activity or enhanced biological activity relative to a reference ABP. In some embodiments, a "reference ABP" is an ABP having the same sequence as the variant ABP, except that it has the three light chain CDR sequences and the three heavy chain CDR sequences of the Parent A antibody (Tables 31 and 32).

ABPs Comprising an Antibody or Antigen-Binding Fragment Thereof

An ABP may comprise an antibody or antigen-binding fragment thereof.

In some embodiments, the ABPs provided herein comprise a light chain. In some aspects, the light chain is a kappa light chain. In some aspects, the light chain is a lambda light chain.

In some embodiments, the ABPs provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the ABPs provided herein comprise an antibody fragment. In some embodiments, the ABPs provided herein consist of an antibody fragment. In some embodiments, the ABPs provided herein consist essentially of an antibody fragment. In some aspects, the ABP fragment is an Fv fragment. In some aspects, the ABP fragment is a Fab fragment. In some aspects, the ABP fragment is a F(ab')$_2$ fragment. In some aspects, the ABP fragment is a Fab' fragment. In some aspects, the ABP fragment is an scFv (sFv) fragment. In some aspects, the ABP fragment is an scFv-Fc fragment. In some aspects, the ABP fragment is a fragment of a single domain ABP.

In some embodiments, an ABP fragment provided herein is derived from an illustrative ABP provided herein. In some embodiments, an ABP fragments provided herein is not derived from an illustrative ABP provided herein and may, for example, be isolated de novo according to the methods provided herein for obtaining ABP fragments.

In some embodiments, an ABP fragment provided herein retains the ability to bind the HLA-PEPTIDE target, as measured by one or more assays or biological effects described herein. In some embodiments, an ABP fragment provided herein retains the ability to prevent HLA-PEPTIDE from interacting with one or more of its ligands, as described herein.

In some embodiments, the ABPs provided herein are monoclonal ABPs. In some embodiments, the ABPs provided herein are polyclonal ABPs.

In some embodiments, the ABPs provided herein comprise a chimeric ABP. In some embodiments, the ABPs provided herein consist of a chimeric ABP. In some embodiments, the ABPs provided herein consist essentially of a chimeric ABP. In some embodiments, the ABPs provided herein comprise a humanized ABP. In some embodiments, the ABPs provided herein consist of a humanized ABP. In some embodiments, the ABPs provided herein consist essentially of a humanized ABP. In some embodiments, the ABPs provided herein comprise a human ABP. In some embodiments, the ABPs provided herein consist of a human ABP. In some embodiments, the ABPs provided herein consist essentially of a human ABP.

In some embodiments, the ABPs provided herein comprise an alternative scaffold. In some embodiments, the ABPs provided herein consist of an alternative scaffold. In some embodiments, the ABPs provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

Also disclosed herein is an isolated humanized, human, or chimeric ABP that competes for binding to an HLA-PEPTIDE with an ABP disclosed herein.

Also disclosed herein is an isolated humanized, human, or chimeric ABP that binds an HLA-PEPTIDE epitope bound by an ABP disclosed herein.

In certain aspects, an ABP comprises a human Fc region comprising at least one modification that reduces binding to a human Fc receptor.

It is known that when an ABP is expressed in cells, the ABP is modified after translation. Examples of the post-translational modification include cleavage of lysine at the C terminus of the heavy chain by a carboxypeptidase; modification of glutamine or glutamic acid at the N terminus of the heavy chain and the light chain to pyroglutamic acid by pyroglutamylation; glycosylation; oxidation; deamidation; and glycation, and it is known that such posttranslational modifications occur in various ABPs (See Journal of Pharmaceutical Sciences, 2008, Vol. 97, p. 2426-2447, incorporated by reference in its entirety). In some embodiments, an ABP is an ABP or antigen-binding fragment thereof which has undergone posttranslational modification. Examples of an ABP or antigen-binding fragment thereof which have undergone posttranslational modification include an ABP or antigen-binding fragments thereof which have undergone pyroglutamylation at the N terminus of the heavy chain variable region and/or deletion of lysine at the C terminus of the heavy chain. It is known in the art that such posttranslational modification due to pyroglutamylation at the N terminus and deletion of lysine at the C terminus does not have any influence on the activity of the ABP or fragment thereof (Analytical Biochemistry, 2006, Vol. 348, p. 24-39, incorporated by reference in its entirety).

Monospecific and Multispecific HLA-PEPTIDE ABPs

In some embodiments, the ABPs provided herein are monospecific ABPs.

In some embodiments, the ABPs provided herein are multispecific ABPs (e.g. bispecific ABPs, trispecific ABPs, etc.).

A multispecific ABP, as described herein, binds more than one antigen. In some embodiments, a multispecific ABP binds 2 antigens. In some embodiments, a multispecific ABP binds 3 antigens. In some embodiments, a multispecific ABP binds 4 antigens. In some embodiments, a multispecific ABP binds 5 antigens.

In some embodiments, a multispecific ABP provided herein binds more than one epitope on a HLA-PEPTIDE antigen. In some embodiments, a multispecific ABP binds 2 epitopes on a HLA-PEPTIDE antigen. In some embodiments, a multispecific ABP binds 3 epitopes on a HLA-PEPTIDE antigen.

Many multispecific ABP constructs are known in the art, and the ABPs provided herein may be provided in the form of any suitable multispecific suitable construct.

In some embodiments, the multispecific ABP comprises an immunoglobulin comprising at least two different heavy chain variable regions each paired with a common light chain variable region (i.e., a "common light chain ABP"). The common light chain variable region forms a distinct antigen-binding domain with each of the two different heavy chain variable regions. See Merchant et al., *Nature Biotechnol.*, 1998, 16:677-681, incorporated by reference in its entirety.

In some embodiments, the multispecific ABP comprises an immunoglobulin comprising an ABP or fragment thereof attached to one or more of the N- or C-termini of the heavy or light chains of such immunoglobulin. See Coloma and Morrison, Nature *Biotechnol.,* 1997, 15:159-163, incorporated by reference in its entirety. In some aspects, such ABP comprises a tetravalent bispecific ABP.

In some embodiments, the multispecific ABP comprises a hybrid immunoglobulin comprising at least two different heavy chain variable regions and at least two different light chain variable regions. See Milstein and Cuello, *Nature*, 1983, 305:537-540; and Staerz and Bevan, *Proc. Natl. Acad. Sci. USA*, 1986, 83:1453-1457; each of which is incorporated by reference in its entirety.

In some embodiments, the multispecific ABP comprises immunoglobulin chains with alterations to reduce the formation of side products that do not have multispecificity. In some aspects, the ABPs comprise one or more "knobs-into-holes" modifications as described in U.S. Pat. No. 5,731,168, incorporated by reference in its entirety.

In some embodiments, the multispecific ABP comprises immunoglobulin chains with one or more electrostatic modifications to promote the assembly of Fc hetero-multimers. See WO 2009/089004, incorporated by reference in its entirety. In some embodiments, the multispecific ABP comprises one or more of mutations that render homodimerization electrostatically unfavorable but heterodimerization favorable.

In some embodiments, the multispecific ABP comprises a bispecific single chain molecule. See Traunecker et al., *EMBO J.*, 1991, 10:3655-3659; and Gruber et al., *J. Immunol.*, 1994, 152:5368-5374; each of which is incorporated by reference in its entirety.

Linkers

In some embodiments, the multispecific ABP comprises a heavy chain variable domain and a light chain variable domain connected by a polypeptide linker, where the length of the linker is selected to promote assembly of multispecific ABP with the desired multispecificity. For example, monospecific scFvs generally form when a heavy chain variable domain and light chain variable domain are connected by a polypeptide linker of more than 12 amino acid residues. See U.S. Pat. Nos. 4,946,778 and 5,132,405, each of which is incorporated by reference in its entirety. In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting ABP therefore has multispecificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) are favored. However, the exact type of oligomerization appears to depend on the amino acid residue composition and the order of the variable domain in each polypeptide chain (e.g., $V_H$-linker-$V_L$ VS. $V_L$-linker-$V_H$), in addition to the linker length. A skilled person can select the appropriate linker length based on the desired multispecificity.

Various linkers are contemplated for use in the ABPs described herein, particularly between the variable domains (variable heavy and variable light domains), between the variable regions and N-terminus of the VH domain of the Fab, and/or between the variable regions and hinge of the first polypeptide. In some embodiments, the linker is a polypeptide linker. In some embodiments, the amino acids in the polypeptide linker are selected with properties that confer flexibility and resist cleavage from proteases (e.g., glycine and serine). In some embodiments, the polypeptide linker comprises one or more glycine and/or serine residues.

In some embodiments, the linker comprises 10 amino acids. In some embodiments, the linker comprises 20 amino acids. In some embodiments, the linker includes one or more glycines. In some embodiments, the linker includes one or more serines. In some embodiments, the linker comprises or consists of glycines and serines. In some embodiments, the linker comprises or consists of a $(GS)_n$ (SEQ ID NO: 44), $(GGS)_n$ (SEQ ID NO: 45), $(GGGS)_n$ (SEQ ID NO: 46), $(GGSG)_n$ (SEQ ID NO: 47), $(GGSGG)_n$ (SEQ ID NO: 48) and (GGGGS), (SEQ ID NO: 49) sequence, wherein n is 1, 2, 3, 4, 5, 6, 7, 8, 9, 10, 11, 12, 13, 14, 15, 16, 17, 18, 19, or 20. In some embodiments, the linker comprises or consists of a (GGGGS)n (SEQ ID NO: 49) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2, or 3. Any combination of glycines and serines in the linker is contemplated. In some embodiments, the linker comprises or consists of a $(GSGGG)_n$ (SEQ ID NO: 50), $(GGSGG)_n$ (SEQ ID NO: 48) or $(GGGSG)_n$ (SEQ ID NO: 51) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2 or 3. In some embodiments, the linker comprises or consists of a $(GGGGG)_n$ (SEQ ID NO: 52) sequence, wherein n is 1, 2, 3, 4, 5, 6, 7, 8, 9, 10, 11, 12, 13, 14, 15, 16, 17, 18, 19, or 20. In some embodiments, the n values are 1, 2, 3 or 4. In some embodiments, the n values are 1, 2, or 3.

Antibody Formats

In certain embodiments, the ABPs provided herein are multispecific ABPs (e.g. bispecific ABPs).

In certain embodiments, the isolated ABPs provided herein are Format 4 antibodies (see FIG. 5) and comprise a first scFv and a second scFv that each specifically bind a first target antigen, a Fab that specifically binds an additional target antigen that is distinct from the first target antigen, and an Fc domain, wherein the ABP comprises a first polypeptide, a second polypeptide, and a third polypeptide, wherein the first polypeptide comprises, in an N→C direction, the first scFv-CH2-CH3, wherein the second polypeptide comprises, in an N→C direction, a VH domain of the Fab-a CH1 domain of the Fab-CH2-CH3, wherein the third polypeptide comprises, in an N→C direction, a VL domain of the Fab-a CL domain of the Fab, and wherein the second scFv is attached, directly or indirectly, to the N-terminus of the second polypeptide or the third polypeptide; wherein the first target antigen is a human leukocyte antigen (HLA)-PEPTIDE target and wherein the first and second scFvs comprise a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3, wherein the heavy chain CDR sequences and light chain CDR sequences are each selected from Table 7 and are from the same clone in Table 7. In some embodiments, the VH sequence and VL sequence are selected from Table 6 and are from the same clone in Table 6. In some embodiments, a Format 4 antibody has an interchain linker of 20 amino acids between the Fab scFv VH or VL and the VL or VH of the second scFv.

Figure 5:
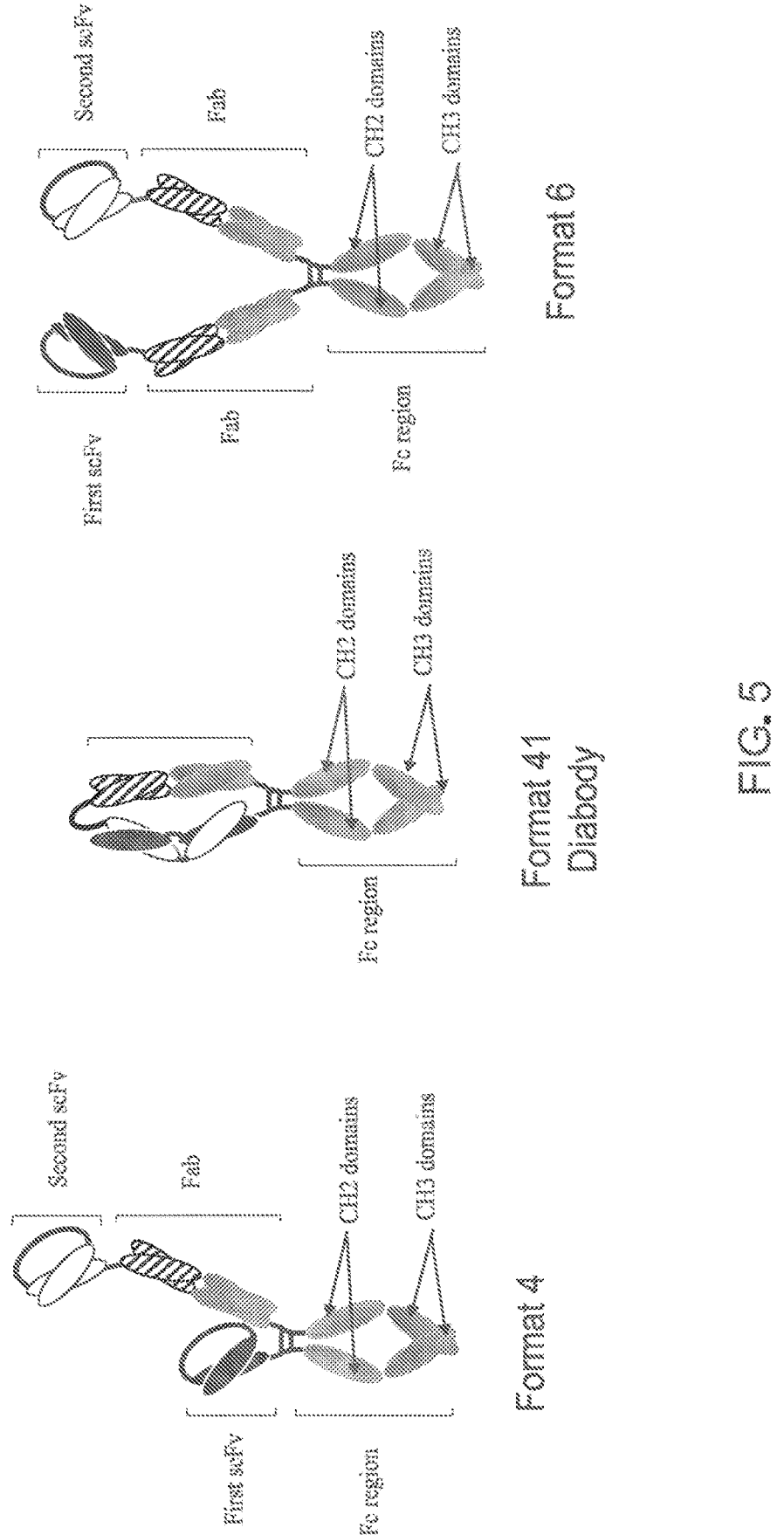
FIG. 5 depicts a Format 4 (e.g., bispecific) antibody format (left), a Format 41 diabody (e.g., bispecific) antibody format (middle), and a Format 6 (e.g., bispecific) antibody format (right).

In certain embodiments, the isolated ABPs provided herein are Format 41 diabody antibodies (see FIG. 5). Format 41 diabodies have the same general structure as the Format 4 antibodies described above and shown in FIG. 5, with an interchain linker of 10 amino acids between the Fab scFv VH or VL and the VL or VH of the second scFv. However, in the diabody of FIG. 5, a VH or VL from the first scFv (in the first polypeptide) can interact with a VL or VH from the second scFv (in the second polypeptide), while a VL or VH from the first scFv (in the first polypeptide) can interact with a VH or VL from the second scFv (in the second polypeptide). These noncovalent interactions that facilitate the pairing can consist of hydrophobic, electrostatic, and van der Waals interactions.

In certain embodiments, the isolated ABPs provided herein are Format 6 antibodies (see FIG. 5) and comprise a first scFv and a second scFv that each specifically bind a first target antigen and a first Fab and a second Fab that each specifically bind an additional target antigen that is distinct from the first target antigen, wherein the ABP comprises a first polypeptide, a second polypeptide, a third polypeptide, and a fourth polypeptide, wherein the first polypeptide comprises, in an N→C direction, a VH domain of the first Fab-CH1-CH2-CH3, wherein the second polypeptide comprises, in an N→C direction, a VH domain of the second Fab-CH1-CH2-CH3, wherein the third polypeptide comprises, in an N→C direction, a VL domain of the first Fab-a CL domain of the first Fab, and wherein the fourth polypeptide comprises, in an N→C direction, a VL domain of the second Fab-a CL domain of the second Fab, and wherein the first scFv is attached, directly or indirectly, to the N-terminus of the first or third polypeptide, and wherein the second scFv is attached, directly or indirectly, to the N-terminus of the second or fourth polypeptide; wherein the first target antigen is a human leukocyte antigen (HLA)-PEPTIDE target and wherein the first and second scFvs comprise a variable heavy chain (VH) sequence comprising three heavy chain CDR sequences: CDR-H1, CDR-H2, and CDR-H3, and a variable light chain (VL) sequence comprising three light chain CDR sequences: CDR-L1, CDR-L2, and CDR-L3 wherein the heavy chain CDR sequences and light chain CDR sequences are each selected from Table 7 and are from the same clone in Table 7. In some embodiments, the VH sequence and VL sequence are selected from Table 6 and are from the same clone in Table 6. In some embodiments, a Format 6 antibody has an interchain linker of 20 amino acids between the Fab scFv VH or VL and the VL or VH of the second scFv.

Alternative formats for the ABPs disclosed herein are also contemplated herein and described in, for example, International Application No. PCT/US2020/015736, which published as WO2020160189A1 on Aug. 6, 2020, which is hereby incorporated by reference in its entirety.

Fc Region and Variants

In certain embodiments, an ABP provided herein comprises an Fc region. An Fc region can be wild-type or a variant thereof. In certain embodiments, an ABP provided herein comprises an Fc region with one or more amino acid substitutions, insertions, or deletions in comparison to a naturally occurring Fc region. In some aspects, such substitutions, insertions, or deletions yield an ABP with altered stability, glycosylation, or other characteristics. In some aspects, such substitutions, insertions, or deletions yield a glycosylated ABP.

A "variant Fc region" or "engineered Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

The term "Fc-region-comprising ABP" refers to an ABP that comprises an Fc region. The C-terminal lysine (residue 447 according to the EU numbering system) of the Fc region may be removed, for example, during purification of the ABP or by recombinant engineering the nucleic acid encoding the ABP. Accordingly, an ABP having an Fc region can comprise an ABP with or without K447.

In some aspects, the Fc region of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, the variant Fc region of an ABP comprises a modification that alters an affinity of the ABP for an Fc receptor as compared to an ABP with a non-variant Fc region.

In some embodiments, the variant Fc region comprises a set of mutations that renders homodimerization electrostatically unfavorable but heterodimerization favorable.

Antibodies Specific for A*02:01 AIFPGAVPAA (SEQ ID NO: 42) (HLA-PEPTIDE Target "G8")

In some aspects, provided herein are ABPs comprising antibodies or antigen-binding fragments thereof that specifically bind an HLA-PEPTIDE target, wherein the HLA Class I molecule of the HLA-PEPTIDE target is HLA subtype A*02:01 and the HLA-restricted peptide of the HLA-PEPTIDE target comprises, consists of, or essentially consists of the sequence AIFPGAVPAA (SEQ ID NO: 42) ("G8").

CDRs

The ABP specific for A*02:01_AIFPGAVPAA (SEQ ID NO: 42) may comprise one or more antibody complementarity determining region (CDR) sequences, e.g., may comprise three heavy chain CDRs (CDR-H1, CDR-H2, CDR-H3) and three light chain CDRs (CDR-L1, CDR-L2, CDR-L3).

The ABP specific for A*02:01_AIFPGAVPAA (SEQ ID NO: 42) may comprise a CDR-H3 sequence. The CDR-H3 sequence may be selected from Table 7.

The ABP specific for A*02:01_AIFPGAVPAA (SEQ ID NO: 42) may comprise a CDR-L3 sequence. The CDR-L3 sequence may be selected from Table 7.

The ABP specific for A*02:01_AIFPGAVPAA (SEQ ID NO: 42) may comprise a particular heavy chain CDR3 (CDR-H3) sequence and a particular light chain CDR3 (CDR-L3) sequence. In some embodiments, the ABP comprises the CDR-H3 and the CDR-L3 from the scFv (clones) designated 05D07, 09G01, 05G06, 09D01, 05G09, 09D06, 05A08, 05A03, 05C04, 05D10, 09D04, or 06D07 (see Table 7). CDR sequences of identified scFvs that specifically bind A*02:01_AIFPGAVPAA (SEQ ID NO: 42) are shown in Table 7. For clarity, each identified scFv hit is designated a clone name, and each row contains the CDR sequences for that particular clone name. For example, the scFv identified by clone name 05D07 comprises the heavy chain CDR3 sequence VEQGYDIYYYYYMDV (SEQ ID NO: 27) and the light chain CDR3 sequence QQSYSAPYT (SEQ ID NO:32).

The ABP specific for A*02:01_AIFPGAVPAA (SEQ ID NO: 42) may comprise all six CDRs from the scFv designated 05D07, 09G01, 05G06, 09D01, 05G09, 09D06, 05A08, 05A03, 05C04, 05D10, 09D04, 06D07, 5D10YF, 9D04YF, 5G06NT, NGS-18 or NGS-22.

In certain embodiments, the ABP comprises the CDR-H3 and the CDR-L3 from the scFv designated 05A03, 05D07, 05D10, 05G06, 06D07, 09D01, 09D04, or 09G01 (see Table 7). The ABP specific for A*02:01_AIFPGAVPAA (SEQ ID NO: 42) may comprise all six CDRs from the scFv designated 05A03, 05D07, 05D10, 05G06, 06D07, 09D01, 09D04, 09G01, 5D10YF, 9D04YF, 5G06NT, NGS-18 or NGS-22 (see Table 7).

In some embodiments, an ABP provided herein comprises one to three CDRs of a VH domain as set forth in SEQ ID NOs: 1, 2, 3, 4, 5, 6, 7, 8, 9, 11, 12, 13, 14, 15, 37, 38, 39, 40, or 41. In some embodiments, an ABP provided herein comprises two to three CDRs of a VH domain as set forth in SEQ ID NOs: 1, 2, 3, 4, 5, 6, 7, 8, 9, 11, 12, 13, 14, 15, 37, 38, 39, 40, or 41. In some embodiments, an ABP provided herein comprises three CDRs of a VH domain as set forth in SEQ ID NOs: 1, 2, 3, 4, 5, 6, 7, 8, 9, 11, 12, 13, 14, 15, 37, 38, 39, 40, or 41. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an ABP provided herein comprises one to three CDRs of a VL domain as set forth in SEQ ID NOs: 2 or 10. In some embodiments, an ABP provided herein comprises two to three CDRs of a VL domain as set forth in SEQ ID NOs: 2 or 10. In some embodiments, an ABP provided herein comprises three CDRs of a VL domain as set forth in SEQ ID NOs: 2 or 10. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

VH

The ABP specific for A*02:01_AIFPGAVPAA (SEQ ID NO: 42) may comprise a VH sequence. The VH sequence may be selected from Table 6. In some embodiments, the ABP comprises the VH sequence from the scFv designated 05D07, 09G01, 05G06, 09D01, 05G09, 09D06, 05A08, 05A03, 05C04, 05D10, 09D04, 06D07, 5D10YF, 9D04YF, 5G06NT, NGS-18 or NGS-22 (see Table 6).

In certain embodiments, the ABP comprises VH sequence from the scFv designated 05A03, 05D07, 05D10, 05G06, 06D07, 09D01, 09D04, 09G01, 5D10YF, 9D04YF, 5G06NT, NGS-18 or NGS-22 (see Table 6).

In some embodiments, an ABP provided herein comprises a VH sequence having at least about 50%, 60%, 70%, 80%, 90%, 95%, 99%, or 100% identity to an VH sequence set forth in SEQ ID NOs: 1, 2, 3, 4, 5, 6, 7, 8, 9, 11, 12, 13, 14, 15, 37, 38, 39, 40, or 41. In some embodiments, an ABP provided herein comprises a VH sequence provided in SEQ ID NOs: 1, 2, 3, 4, 5, 6, 7, 8, 9, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

VL

The ABP specific for A*02:01_AIFPGAVPAA (SEQ ID NO: 42) may comprise a VL sequence. The VL sequence may be selected from Table 6. In some embodiments, the ABP comprises the VL sequence from the scFv designated 05D07, 09G01, 05G06, 09D01, 05G09, 09D06, 05A08, 05A03, 05C04, 05D10, 09D04, 06D07, 5D10YF, 9D04YF, 5G06NT, NGS-18 or NGS-22 (see Table 6).

In certain embodiments, the ABP comprises VL sequence from the scFv designated 05A03, 05D07, 05D10, 05G06, 06D07, 09D01, 09D04, 09G01, 5D10YF, 9D04YF, 5G06NT, NGS-18 or NGS-22 (see Table 6).

In some embodiments, an ABP provided herein comprises a VL sequence having at least about 50%, 60%, 70%, 80%, 90%, 95%, 99%, or 100% identity to an VL sequence set forth in SEQ ID NOs: 2 or 10. In some embodiments, an ABP provided herein comprises a VL sequence provided in SEQ ID NOs: 2 or 10, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

VH-VL Combinations

The ABP specific for A*02:01_AIFPGAVPAA (SEQ ID NO: 42) may comprise a particular VH sequence and a particular VL sequence. In some embodiments, the ABP specific for A*02:01_AIFPGAVPAA (SEQ ID NO: 42) comprises a VH sequence and VL sequence selected from Table 6, wherein the VH and VL sequences are selected from the same clone in Table 6. In some embodiments, the ABP comprises a VH sequence and VL sequence from the scFv designated 05D07, 09G01, 05G06, 09D01, 05G09, 09D06, 05A08, 05A03, 05C04, 05D10, 09D04, 06D07, 5D10YF, 9D04YF, 5G06NT, NGS-18 or NGS-22 (see Table 6). In certain embodiments, the ABP comprises a VH sequence and VL sequence from the scFv designated 05A03, 05D07, 05D10, 05G06, 06D07, 09D01, 09D04, 09G01, 5D10YF, 9D04YF, 5G06NT, NGS-18 or NGS-22 (see Table 6). The VH and VL sequences of identified scFvs that specifically bind A*02:01_AIFPGAVPAA (SEQ ID NO: 42) are shown in Table 6. For clarity, each identified scFv hit is designated a clone name, and each row contains the VH and VL sequences for that particular clone name. For example, the scFv identified by clone name 05A03 comprises the VH sequence EVQLLESGGGLVQPGGSLRLSCAASGYT-FSDYYMSWVRQAPGKGLEWVSGINWPG GSTG-YADSVKGRFTISRDNSKNTLYLQMNSLRAEDTAVYY-CARVEQGYDIYYYYY MDVWGKGTTVTVSS (SEQ ID NO: 1) and the VL sequence DIQMTQSPSSL-SASVGDRVTITCRASQSISSYLNWYQQKPGK-APKLLIYKASSLESGV PSRFSGSGSGTDFTLTISSLQ-PEDFATYYCQQSYSAPYTFGPGTKVDIK (SEQ ID NO: 2).

In some embodiments, an ABP provided herein comprises a VH sequence having at least about 50%, 60%, 70%, 80%, 90%, 95%, 99%, or 100% identity to an VH sequence set forth in SEQ ID NOs: 1, 2, 3, 4, 5, 6, 7, 8, 9, 11, 12, 13, 14, 15, 37, 38, 39, 40, or 41 and a VL sequence having at least about 50%, 60%, 70%, 80%, 90%, 95%, 99%, or 100% identity to an VL sequence set forth in SEQ ID NOs: 2 or 10. In some embodiments, an ABP provided herein comprises a VH sequence provided in SEQ ID NOs: 1, 2, 3, 4, 5, 6, 7, 8, 9, 11, 12, 13, 14, 15, 37, 38, 39, 40, or 41, and a VL sequence provided in SEQ ID NOs: 2 or 10 with up to 1, 2, 3, 4, 5, 6, 7, 8, 9, 10, 11, 12, 13, 14, 15, 16, 17, 18, 19, 20, 21, 22, 23, 24, or 25 amino acid substitutions in each of the VH and VL sequences. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

Receptors

Among the provided ABPs, e.g., HLA-PEPTIDE ABPs, are receptors. The receptors can include antigen receptors and other chimeric receptors that specifically bind an HLA-PEPTIDE target disclosed herein. The receptor may be a chimeric antigen receptor (CAR).

Exemplary antigen receptors, including CARs, and methods for engineering and introducing such receptors into cells, include those described, for example, in international patent application publication numbers WO2000/14257, WO2013/126726, WO2012/129514, WO2014/031687, WO2013/166321, WO2013/071154, WO2013/123061; U.S. patent application publication numbers US2002131960, US2013287748, US20130149337; U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLOS ONE 8 (4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Exemplary of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody, e.g., as provided herein.

Among the chimeric receptors are chimeric antigen receptors (CARs). The chimeric receptors, such as CARs, generally include an extracellular antigen binding domain that includes, is, or is comprised within, one of the provided anti-HLA-PEPTIDE ABPs such as anti-HLA-PEPTIDE antibodies. Thus, the chimeric receptors, e.g., CARs, typically include in their extracellular portions one or more HLA-PEPTIDE-ABPs, such as one or more antigen-binding fragment, domain, or portion, or one or more antibody variable domains, and/or antibody molecules, such as those described herein. In some embodiments, the CAR includes a HLA-PEPTIDE-binding portion or portions of the ABP (e.g., antibody) molecule, such as a variable heavy (VH)

chain region and/or variable light (VL) chain region of the antibody, e.g., an scFv antibody fragment.

In some embodiments, the CAR is a recombinant CAR. The recombinant CAR may include any of the TCRs identified herein but include one or more modifications. Exemplary modifications, e.g., amino acid substitutions, are described herein. Amino acid substitutions described herein may be made with reference to IMGT nomenclature and amino acid numbering as found at www.imgt.org.

The recombinant CAR may be a human CAR, comprising fully human sequences, e.g., natural human sequences. The recombinant CAR may retain its natural human variable domain sequences but contain modifications to the a constant region, β constant region, or both α and β constant regions. Such modifications to the CAR constant regions may improve CAR assembly and expression for CAR gene therapy by, e.g., driving preferential pairings of the exogenous CAR chains. In some embodiments, the α and β constant regions are modified by substituting the entire human constant region sequences for mouse constant region sequences.

In some embodiments, the α and β chains are modified by linking the extracellular domains of the α and β chains to a complete human CD3ζ (CD3-zeta) molecule. Such modifications are described in J Immunol Jun. 1, 2008, 180 (11)7736-7746; Gene Ther. 2000 August; 7(16):1369-77; and The Open Gene Therapy Journal, 2011, 4:11-22, which are hereby incorporated by reference in their entirety.

In some embodiments, the α chain is modified by introducing hydrophobic amino acid substitutions in the transmembrane region of the α chain, as described in J Immunol Jun. 1, 2012, 188 (11)5538-5546; hereby incorporated by reference in their entirety.

The alpha or beta chain may be modified by altering any one of the N-glycosylation sites in the amino acid sequence, as described in J Exp Med. 2009 Feb. 16; 206(2): 463-475; hereby incorporated by reference in its entirety.

The alpha and beta chain may each comprise a dimerization domain, e.g., a heterologous dimerization domain. Such a heterologous domain may be a leucine zipper, a 5H3 domain or hydrophobic proline rich counter domains, or other similar modalities, as known in the art. In one example, the alpha and beta chains may be modified by introducing 30 mer segments to the carboxyl termini of the alpha and beta extracellular domains, wherein the segments selectively associate to form a stable leucine zipper. Such modifications are described in PNAS Nov. 22, 1994. 91 (24)11408-11412; which can be found at the website located at: doi.org/10.1073/pnas.91.24.11408; hereby incorporated by reference in its entirety.

In some embodiments, the recombinant receptor such as a CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the constant region or portion is of IgD.

The antigen recognition domain of a receptor such as a CAR can be linked to one or more intracellular signaling components, such as signaling components that mimic activation through an antigen receptor complex and/or signal via another cell surface receptor. Thus, in some embodiments, the HLA-PEPTIDE-specific binding component (e.g., ABP) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD134, CD137, and/or CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the receptor.

The receptor, e.g., the CAR, can include at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the HLA-PEPTIDE-binding ABP (e.g., antibody) is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor-gamma, CD8, CD4, CD25, or CD16. For example, in some aspects, the CAR includes a chimeric molecule between CD3-zeta or Fc receptor-gamma and CD8, CD4, CD25 or CD16.

In some embodiments, upon ligation of the CAR, the cytoplasmic domain or intracellular signaling domain of the receptor activates at least one of the normal effector functions or responses of the immune cell, e.g., T cell engineered to express the receptor. For example, in some contexts, the receptor induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the receptor. In other embodiments, the receptor does not include a component for generating a costimulatory signal. In some aspects, an additional receptor is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the receptor includes one or both of such signaling components.

In some aspects, the receptor includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the receptor includes a signaling domain and/or transmembrane portion of a costimulatory receptor, such as CD28, 4-1BB, OX40, DAP10, and ICOS. In some aspects, the same receptor includes both the activating and costimulatory components.

In some embodiments, the activating domain is included within one receptor, whereas the costimulatory component is provided by another receptor recognizing another antigen. In some embodiments, the receptors include activating or stimulatory receptors, and costimulatory receptors, both expressed on the same cell (see WO2014/055668). In some aspects, the HLA-PEPTIDE-targeting receptor is the stimulatory or activating receptor; in other aspects, it is the costimulatory receptor. In some embodiments, the cells further include inhibitory receptors (e.g., iCARs, see Fedorov et al., Sci. Transl. Medicine, 5(215) (December 2013), such as a receptor recognizing an antigen other than HLA-PEPTIDE, whereby an activating signal delivered through the HLA-PEPTIDE-targeting receptor is diminished or inhibited by binding of the inhibitory receptor to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the receptor encompasses one or more, e.g., two or more, costimulatory domains and an activation domain, e.g., primary activation domain, in the cytoplasmic portion. Exemplary receptors include intracellular components of CD3-zeta, CD28, and 4-1BB.

In some embodiments, the receptor (e.g., CAR) further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a nerve growth factor receptor (NGFR), or epidermal growth factor receptor (e.g., tEGFR). In some embodiments, the nucleic acid encoding the marker is operably linked to a polynucleotide encoding for a linker sequence, such as a cleavable linker sequence or a ribosomal skip sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A ribosomal skip sequence.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

The receptor, e.g., CAR, may comprise one or modified synthetic amino acids in place of one or more naturally-occurring amino acids. Exemplary modified amino acids include, but are not limited to, aminocyclohexane carboxylic acid, norleucine, α-amino n-decanoic acid, homoserine, S-acetylaminomethylcysteine, trans-3- and trans-4-hydroxyproline, 4-aminophenylalanine, 4-nitrophenylalanine, 4-chlorophenylalanine, 4-carboxyphenylalanine, (3-phenylserine (3-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,γ-diaminopropionic acid, homophenylalanine, and α-tertbutylglycine.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the CAR includes an extracellular portion containing an antibody or fragment described herein. In some aspects, the chimeric antigen receptor includes an extracellular portion containing an antibody or fragment described herein and an intracellular signaling domain. In some embodiments, an antibody or fragment includes an scFv or a single-domain VH antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR, is a transmembrane domain of human CD28 or variant thereof, e.g., a 27-amino acid transmembrane domain of a human CD28 (Accession No.: P10747.1).

In some embodiments, the CAR contains an intracellular domain of a T cell costimulatory molecule. In some aspects, the T cell costimulatory molecule is CD28 or 41BB.

In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof.

In some embodiments, the intracellular signaling domain comprises a human CD3 zeta stimulatory signaling domain or functional variant thereof, such as a 112 AA cytoplasmic domain of isoform 3 of human CD3.zeta. (Accession No.: P20963.2) or a CD3 zeta signaling domain as described in U.S. Pat. No. 7,446,190 or U.S. Pat. No. 8,911,993.

In some aspects, the spacer contains only a hinge region of an IgG, such as only a hinge of IgG4 or IgG1. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes an antibody or fragment thereof, such as any of the HLA-PEPTIDE antibodies, including single chain antibodies (sd-Abs, e.g. containing only the VH region) and scFvs, described herein, a spacer such as any of the Ig-hinge containing spacers, a CD28 transmembrane domain, a CD28 intracellular signaling domain, and a CD3 zeta signaling domain. In some embodiments, the CAR includes an antibody or fragment, such as any of the HLA-PEPTIDE antibodies, including sdAbs and scFvs described herein, a spacer such as any of the Ig-hinge containing spacers, a CD28 transmembrane domain, a CD28 intracellular signaling domain, and a CD3 zeta signaling domain.

Engineered Cells

Also provided herein are cells such as cells that contain an antigen receptor, e.g., that contains an extracellular domain including an anti-HLA-PEPTIDE ABP (e.g., a CAR), described herein. Also provided are populations of such cells, and compositions containing such cells. In some embodiments, compositions or populations are enriched for such cells, such as in which cells expressing the HLA-PEPTIDE ABP make up at least 1, 5, 10, 20, 30, 40, 50, 60, 70, 80, 90, 91, 92, 93, 94, 95, 96, 97, 98, 99, or more than 99 percent of the total cells in the composition or cells of a certain type such as T cells or CD8+ or CD4+ cells. In some embodiments, a composition comprises at least one cell containing an antigen receptor disclosed herein. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing an ABP comprising a receptor, e.g., a CAR. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MALT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

The cells may be genetically modified to reduce expression or knock out endogenous TCRs. Such modifications are described in *Mol Ther Nucleic Acids.* 2012 December; 1(12): e63; Blood. 2011 Aug. 11; 118(6):1495-503; Blood. 2012 Jun. 14; 119(24): 5697-5705; Torikai, Hiroki et al "HLA and TCR Knockout by Zinc Finger Nucleases: Toward "off-the-Shelf" Allogeneic T-Cell Therapy for CD19+Malignancies." *Blood* 116.21 (2010): 3766*; Blood.* 2018 Jan. 18; 131(3):311-322. doi: 10.1182/blood-2017-05-787598; and WO2016069283, which are incorporated by reference in their entirety.

The cells may be genetically modified to promote cytokine secretion. Such modifications are described in Hsu C, Hughes M S, Zheng Z, Bray R B, Rosenberg S A, Morgan RA. Primary human T lymphocytes engineered with a codon-optimized IL-15 gene resist cytokine withdrawal-induced apoptosis and persist long-term in the absence of exogenous cytokine. *J Immunol.* 2005; 175:7226-34; Quintarelli C, Vera J F, Savoldo B, Giordano Attianese G M, Pule M, Foster A E, Co-expression of cytokine and suicide genes to enhance the activity and safety of tumor-specific cytotoxic T lymphocytes. *Blood.* 2007; 110:2793-802; and Hsu C, Jones S A, Cohen C J, Zheng Z, Kerstann K, Zhou J, Cytokine-independent growth and clonal expansion of a primary human CD8+ T-cell clone following retroviral transduction with the IL-15 gene. *Blood.* 2007; 109:5168-77.

Mismatching of chemokine receptors on T cells and tumor-secreted chemokines has been shown to account for the suboptimal trafficking of T cells into the tumor microenvironment. To improve efficacy of therapy, the cells may be genetically modified to increase recognition of chemokines in tumor micro environment. Examples of such modifications are described in Moon et al., Expression of a functional CCR2 receptor enhances tumor localization and tumor eradication by retargeted human T cells expressing a mesothelin-specific chimeric antibody receptor. *Clin Cancer Res.* 2011; 17:4719-4730; and Craddock et al., Enhanced tumor trafficking of GD2 chimeric antigen receptor T cells by expression of the chemokine receptor CCR2b. *J Immunother.* 2010; 33:780-788.

The cells may be genetically modified to enhance expression of costimulatory/enhancing receptors, such as CD28 and 41BB.

Adverse effects of T cell therapy can include cytokine release syndrome and prolonged B-cell depletion. Introduction of a suicide/safety switch in the recipient cells may improve the safety profile of a cell-based therapy. Accordingly, the cells may be genetically modified to include a suicide/safety switch. The suicide/safety switch may be a gene that confers sensitivity to an agent, e.g., a drug, upon the cell in which the gene is expressed, and which causes the cell to die when the cell is contacted with or exposed to the agent. Exemplary suicide/safety switches are described in Protein Cell. 2017 August; 8(8): 573-589. The suicide/safety switch may be HSV-TK. The suicide/safety switch may be cytosine deaminase, purine nucleoside phosphorylase, or nitroreductase. The suicide/safety switch may be RapaCIDe™, described in U.S. Patent Application Pub. No. US20170166877A1. The suicide/safety switch system may be CD20/Rituximab, described in Haematologica. 2009 September; 94(9): 1316-1320. These references are incorporated by reference in their entirety.

The CAR may be introduced into the recipient cell as a split receptor which assembles only in the presence of a heterodimerizing small molecule. Such systems are described in Science. 2015 Oct. 16; 350(6258): aab4077, and in U.S. Pat. No. 9,587,020, which are hereby incorporated by reference.

In some embodiments, the cells include one or more nucleic acids, e.g., a polynucleotide encoding a CAR disclosed herein, wherein the polynucleotide is introduced via genetic engineering, and thereby express recombinant or genetically engineered CARs as disclosed herein. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The nucleic acids may include a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

A construct or vector may be used to introduce the CAR into the recipient cell. Exemplary constructs are described herein. Polynucleotides encoding the alpha and beta chains of the CAR may in a single construct or in separate constructs. The polynucleotides encoding the alpha and beta chains may be operably linked to a promoter, e.g., a heterologous promoter. The heterologous promoter may be a strong promoter, e.g., EF1alpha, CMV, PGK1, Ubc, beta actin, CAG promoter, and the like. The heterologous promoter may be a weak promoter. The heterologous promoter may be an inducible promoter. Exemplary inducible promoters include, but are not limited to TRE, NFAT, GAL4, LAC, and the like. Other exemplary inducible expression systems are described in U.S. Pat. Nos. 5,514,578; 6,245,531; 7,091,038 and European Patent No. 0517805, which are incorporated by reference in their entirety.

The construct for introducing the CAR into the recipient cell may also comprise a polynucleotide encoding a signal peptide (signal peptide element). The signal peptide may promote surface trafficking of the introduced CAR. Exemplary signal peptides include, but are not limited to CD8 signal peptide, immunoglobulin signal peptides, where specific examples include GM-CSF and IgG kappa. Such signal peptides are described in Trends Biochem Sci. 2006 October; 31(10): 563-71. Epub 2006 Aug. 21; and An, et al. "Construction of a New Anti-CD19 Chimeric Antigen Receptor and the Anti-Leukemia Function Study of the Transduced T Cells." *Oncotarget* 7.9 (2016): 10638-10649. PMC. Web. 16 Aug. 2018; which are hereby incorporated by reference.

In some cases, e.g., cases where the alpha and beta chains are expressed from a single construct or open reading frame, or cases wherein a marker gene is included in the construct, the construct may comprise a ribosomal skip sequence. The ribosomal skip sequence may be a 2A peptide, e.g., a P2A or T2A peptide. Exemplary P2A and T2A peptides are described in Scientific Reports volume 7, Article number: 2193 (2017), hereby incorporated by reference in its entirety. In some cases, a FURIN/PACE cleavage site is introduced upstream of the 2A element. FURIN/PACE cleavage sites are described in, e.g., the website located at: www.nuolan-.net/substrates.html. The cleavage peptide may also be a factor Xa cleavage site. In cases where the alpha and beta chains are expressed from a single construct or open reading frame, the construct may comprise an internal ribosome entry site (IRES).

The construct may further comprise one or more marker genes. Exemplary marker genes include but are not limited to GFP, luciferase, HA, lacZ. The marker may be a selectable marker, such as an antibiotic resistance marker, a heavy metal resistance marker, or a biocide resistant marker, as is known to those of skill in the art. The marker may be a complementation marker for use in an auxotrophic host. Exemplary complementation markers and auxotrophic hosts are described in Gene. 2001 Jan. 24; 263(1-2):159-69. Such markers may be expressed via an IRES, a frameshift sequence, a 2A peptide linker, a fusion with the TCR or CAR, or expressed separately from a separate promoter.

Exemplary vectors or systems for introducing CARs into recipient cells include, but are not limited to Adeno-associated virus, Adenovirus, Adenovirus+Modified vaccinia, Ankara virus (MVA), Adenovirus+Retrovirus, Adenovirus+ Sendai virus, Adenovirus+Vaccinia virus, Alphavirus (VEE) Replicon Vaccine, Antisense oligonucleotide, *Bifidobacterium longum*, CRISPR-Cas9, *E. coli*, Flavivirus, Gene gun, Herpesviruses, Herpes simplex virus, *Lactococcus lactis*, Electroporation, Lentivirus, Lipofection, *Listeria monocytogenes*, Measles virus, Modified Vaccinia Ankara virus (MVA), mRNA Electroporation, Naked/Plasmid DNA, Naked/Plasmid DNA+Adenovirus, Naked/Plasmid DNA+ Modified Vaccinia Ankara virus (MVA), Naked/Plasmid DNA+RNA transfer, Naked/Plasmid DNA+Vaccinia virus, Naked/Plasmid DNA+Vesicular stomatitis virus, Newcastle disease virus, Non-viral, PiggyBac™ (PB) Transposon, nanoparticle-based systems, Poliovirus, Poxvirus, Poxvirus+ Vaccinia virus, Retrovirus, RNA transfer, RNA transfer+ Naked/Plasmid DNA, RNA virus, *Saccharomyces cerevisiae*, *Salmonella typhimurium*, Semliki forest virus, Sendai virus, *Shigella dysenteriae*, Simian virus, siRNA, Sleeping Beauty transposon, *Streptococcus mutans*, Vaccinia virus, Venezuelan equine encephalitis virus replicon, Vesicular stomatitis virus, and *Vibrio cholera.*

In preferred embodiments, the CAR is introduced into the recipient cell via adeno associated virus (AAV), adenovirus, CRISPR-CAS9, herpesvirus, lentivirus, lipofection, mRNA electroporation, PiggyBac™ (PB) Transposon, retrovirus, RNA transfer, or Sleeping Beauty transposon.

In some embodiments, a vector for introducing a CAR into a recipient cell is a viral vector. Exemplary viral vectors include adenoviral vectors, adeno-associated viral (AAV) vectors, lentiviral vectors, herpes viral vectors, retroviral vectors, and the like. Such vectors are described herein.

Nucleotides, Vectors, Host Cells, and Related Methods

Also provided herein are isolated nucleic acids encoding HLA-PEPTIDE ABPs, vectors comprising the nucleic acids, and host cells comprising the vectors and nucleic acids, as well as recombinant techniques for the production of the ABPs.

The nucleic acids may be recombinant. The recombinant nucleic acids may be constructed outside living cells by joining natural or synthetic nucleic acid segments to nucleic acid molecules that can replicate in a living cell, or replication products thereof. For purposes herein, the replication can be in vitro replication or in vivo replication.

For recombinant production of an ABP, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Exemplary vectors or constructs suitable for expressing an ABP, e.g., a TCR, CAR, antibody, or antigen binding fragment thereof, include, e.g., the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as AGTIO, AGTI 1, AZapII (Stratagene), AEMBL4, and ANMI 149, are also suitable for expressing an ABP disclosed herein.

Illustrative examples of suitable host cells are provided below. These host cells are not meant to be limiting, and any suitable host cell may be used to produce the ABPs provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for HLA-PEPTIDE ABP-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma* reesia, *Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), K-562, A375 and the like.

The host cells used to produce the HLA-PEPTIDE ABP may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the ABP can be produced intracellularly, in the periplasmic space, or directly secreted into the medium. If the ABP is produced intracellularly, as a first step, the particulate debris, either host cells or lysed fragments, is removed, for example, by centrifugation or ultrafiltration. For example, Carter et al. (*Bio/Technology,* 1992, 10:163-167, incorporated by reference in its entirety) describes a procedure for isolating ABPs which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the ABP is produced in a cell-free system. In some aspects, the cell-free system is an in vitro transcription and translation system as described in Yin et al., *mAbs,* 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the ABP may be useful, for example, where the ABP accumulates in a cell as an insoluble aggregate, or where yields from periplasmic expression are low.

Where the ABP is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The ABP composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the ABP. Protein A can be used to purify ABPs that comprise human γ1, γ2, or γ4 heavy chains (Lindmark et al., *J. Immunol. Meth.,* 1983, 62:1-13, incorporated by reference in its entirety). Protein G is useful for all mouse isotypes and for human γ3 (Guss et al., *EMBO J.,* 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the ABP comprises a CH3 domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the ABP of interest and contaminants may be subjected to low pH hydrophobic interaction chromatography using an elution buffer at a pH between about 2.5 to about 4.5, generally performed at low salt concentrations (e.g., from about 0 to about 0.25 M salt).

Methods for Engineering Cells with ABPs

Also provided are methods, nucleic acids, compositions, and kits, for expressing the ABPs, including receptors comprising antibodies and CARs, and for producing genetically engineered cells expressing such ABPs. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) *Exp Hematol* 28(10): 1137-46; Alonso-Camino et al. (2013) *Mol Ther Nucl* Acids 2, e93; Park et al., *Trends Biotechnol.* 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993), *Cur. Opin. Genet. Develop.* 3:102-109.

Methods of lentiviral transduction are known. Exemplary methods are described in, e.g., Wang et al. (2012) *J. Immunother.* 35(9): 689-701; Cooper et al. (2003) *Blood.* 101:

1637-1644; Verhoeven et al. (2009) *Methods Mol Biol.* 506:97-114; and Cavalieri et al. (2003) *Blood.* 102(2): 497-505.

In some embodiments, recombinant nucleic acids are transferred into T cells via electroporation (see, e.g., Chicaybam et al., (2013) *PLOS ONE* 8(3): e60298; Van Tedeloo et al. (2000) *Gene Therapy* 7(16): 1431-1437; and Roth et al. (2018) *Nature* 559:405-409). In some embodiments, recombinant nucleic acids are transferred into T cells via transposition (see, e.g., Manuri et al. (2010) *Hum Gene Ther* 21(4): 427-437; Sharma et al. (2013) *Molec Ther Nucl Acids* 2, e74; and Huang et al. (2009) *Methods Mol Biol* 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, *Nature,* 346:776-777 (1990)); and strontium phosphate DNA co-precipitation (Brash et al., *Mol. Cell Biol.,* 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells: genes to provide a genetic marker for selection and/or evaluation of the cells, such as to assess in vivo survival or localization: genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992): see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Preparation of Engineered Cells

In some embodiments, preparation of the engineered cells includes one or more culture and/or preparation steps. The cells for introduction of the HLA-PEPTIDE-ABP, e.g., CAR, can be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

Assays

A variety of assays known in the art may be used to identify and characterize an HLA-PEPTIDE ABP provided herein.

Binding, Competition, and Epitope Mapping Assays

Specific antigen-binding activity of an ABP provided herein may be evaluated by any suitable method, including using SPR, BLI, RIA and MSD, as described elsewhere in this disclosure. Additionally, antigen-binding activity may be evaluated by ELISA assays, using flow cytometry, and/or Western blot assays.

Assays for measuring competition between two ABPs, or an ABP and another molecule (e.g., one or more ligands of HLA-PEPTIDE such as a TCR) are described elsewhere in this disclosure and, for example, in Harlow and Lane, ABPs: *A Laboratory Manual* ch. 14, 1988, Cold Spring Harbor Laboratory, Cold Spring Harbor, N.Y, incorporated by reference in its entirety.

Assays for mapping the epitopes to which an ABP provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by mutagenesis. In some embodiments, the epitope is determined by crystallography.

Assays for Effector Functions

Effector function following treatment with an ABP and/or cell provided herein may be evaluated using a variety of in vitro and in vivo assays known in the art, including those described in Ravetch and Kinet, *Annu. Rev. Immunol.,* 1991, 9:457-492; U.S. Pat. Nos. 5,500,362, 5,821,337; Hellstrom et al., *Proc. Nat'l Acad. Sci. USA,* 1986, 83:7059-7063; Hellstrom et al., *Proc. Nat'l Acad. Sci. USA,* 1985, 82:1499-1502; Bruggemann et al., *J. Exp. Med.,* 1987, 166:1351-1361; Clynes et al., *Proc. Nat'l Acad. Sci. USA,* 1998, 95:652-656; WO 2006/029879; WO 2005/100402; Gazzano-Santoro et al., *J. Immunol. Methods,* 1996, 202:163-171; Cragg et al., *Blood,* 2003, 101:1045-1052; Cragg et al. *Blood,* 2004, 103:2738-2743; and Petkova et al., *Int'l. Immunol.,* 2006, 18:1759-1769; each of which is incorporated by reference in its entirety.

Cytotoxicity Assays

Assays for evaluating cytotoxicity of the ABPs provided herein are described elsewhere in this disclosure.

Pharmaceutical Compositions

An ABP, cell, or HLA-PEPTIDE target provided herein can be formulated in any appropriate pharmaceutical composition and administered by any suitable route of administration. Suitable routes of administration include, but are not limited to, the intra-arterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients.

As discussed in more detail elsewhere in this disclosure, an ABP and/or cell provided herein may optionally be administered with one or more additional agents useful to prevent or treat a disease or disorder. The effective amount of such additional agents may depend on the amount of ABP present in the formulation, the type of disorder or treatment, and the other factors known in the art or described herein.

Therapeutic Applications

For therapeutic applications, ABPs and/or cells are administered to a subject, generally a human, in a pharmaceutically acceptable dosage form such as those known in the art and those discussed above. For example, ABPs and/or cells may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The ABPs also are suitably administered by peritumoral, intralesional, or perilesional routes, to exert local as well as systemic therapeutic effects. The intraperitoneal route may be particularly useful, for example, in the treatment of ovarian tumors.

The ABPs and/or cells provided herein can be useful for the treatment of any disease or condition involving HLA-PEPTIDE. In some embodiments, the disease or condition is a disease or condition that can benefit from treatment with an anti-HLA-PEPTIDE ABP and/or cell. In some embodiments, the disease or condition is a tumor. In some embodiments, the disease or condition is a cell proliferative disorder. In some embodiments, the disease or condition is a cancer.

In some embodiments, the ABPs and/or cells provided herein are provided for use as a medicament. In some embodiments, the ABPs and/or cells provided herein are provided for use in the manufacture or preparation of a medicament. In some embodiments, the medicament is for the treatment of a disease or condition that can benefit from an anti-HLA-PEPTIDE ABP and/or cell. In some embodiments, the disease or condition is a tumor. In some embodiments, the disease or condition is a cell proliferative disorder. In some embodiments, the disease or condition is a cancer.

In some embodiments, provided herein is a method of treating a disease or condition in a subject in need thereof by administering an effective amount of an ABP and/or cell provided herein to the subject. In some aspects, the disease or condition is a cancer.

In some embodiments, provided herein is a method of treating a disease or condition in a subject in need thereof by administering an effective amount of an ABP and/or cell provided herein to the subject, wherein the disease or condition is a cancer, and the cancer is selected from a solid tumor and a hematological tumor.

In some embodiments, provided herein is a method of modulating an immune response in a subject in need thereof, comprising administering to the subject an effective amount of an ABP and/or cell or a pharmaceutical composition disclosed herein.

Diagnostic Methods

Also provided are methods for predicting and/or detecting the presence of a given HLA-PEPTIDE on a cell from a subject. Such methods may be used, for example, to predict and evaluate responsiveness to treatment with an ABP and/or cell provided herein.

In some embodiments, a blood or tumor sample is obtained from a subject and the fraction of cells expressing HLA-PEPTIDE is determined. In some aspects, the relative amount of HLA-PEPTIDE expressed by such cells is determined. The fraction of cells expressing HLA-PEPTIDE and the relative amount of HLA-PEPTIDE expressed by such cells can be determined by any suitable method. In some embodiments, flow cytometry is used to make such measurements. In some embodiments, fluorescence assisted cell sorting (FACS) is used to make such measurement. See Li et al., *J. Autoimmunity,* 2003, 21:83-92 for methods of evaluating expression of HLA-PEPTIDE in peripheral blood.

In some embodiments, detecting the presence of a given HLA-PEPTIDE on a cell from a subject is performed using immunoprecipitation and mass spectrometry. This can be performed by obtaining a tumor sample (e.g., a frozen tumor sample) such as a primary tumor specimen and applying immunoprecipitation to isolate one or more peptides. The HLA alleles of the tumor sample can be determined experimentally or obtained from a third party source. The one or more peptides can be subjected to mass spectrometry (MS) to determine their sequence(s). The spectra from the MS can then be searched against a database. An example is provided in the Examples section below.

In some embodiments, predicting the presence of a given HLA-PEPTIDE on a cell from a subject is performed using a computer-based model applied to the peptide sequence and/or RNA measurements of one or more genes comprising that peptide sequence (e.g., RNA seq or RT-PCR, or nanostring) from a tumor sample. The model used can be as described in international patent application no. PCT/US2016/067159, herein incorporated by reference, in its entirety, for all purposes.

Kits

Also provided are kits comprising an ABP and/or cell provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an ABP provided herein. The label or package insert indicates that the composition is used for treating the selected condition.

In some embodiments, the kit comprises (a) a first container with a first composition contained therein, wherein the first composition comprises an ABP and/or cell provided herein; and (b) a second container with a second composition contained therein, wherein the second composition comprises a further therapeutic agent. The kit in this embodiment can further comprise a package insert indicating that the compositions can be used to treat a particular condition, e.g., cancer.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

60° C. for 10 sec, and 72° C. for 20 sec. The PCR products were purified using QIAEXII Gel Extraction Kit (Qiagen). The scFv genes were cut with restriction enzymes BglI, agarose gel-purified, and ligated into the plasmid pADL23c cut with BglI. The ligated DNA was electroporated into TG1 cells and plated on 2XYT-GA agar plates. A representative number of clones was sequenced in order to demonstrate that the designed diversity was represented in the final library. Bacteria containing pooled clones were infected with helper phage to produce the bacteriophage antibody library. After infection, amplified phage were precipitated by PEG and employed for rounds of selection.

Table 5 shows the resulting library sizes for G8-ParentA VH and G8-Parent A VL following the determination of phage antibody library quality.

TABLE 4

| | CDR1 | | | CDR2 | | | CDR3 | | | Overall |
|---|---|---|---|---|---|---|---|---|---|---|
| Bacteriophage libraries prepared using the Parent A lead | | | | | | | | | | |
| Library | Single | Double | Triples | Single | Double | Triples | Single | Double | Triples | Diversity |
| G8-Parent A_VH | 49 | 0 | 0 | 2176 | 0 | 0 | 85 | 3387 | 5000 | 9.03E+08 |
| G8-Parent A_VL | 56 | 0 | 0 | 35 | 522 | 4300 | 43 | 805 | 5000 | 1.59E+09 |

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Design and Construction of Phage Library for Affinity Maturation

Two bacteriophage libraries were prepared from the Parent A lead (also referred to herein as "G8_Parent A"): one for VL sequences and one for VH sequences (see Table 4). Sequences were analyzed and CDRs identified according to the Kabat numbering system. Synthetic fragment pools with variability built into the CDRs were ordered, with diversity included in all CDRs, but more diversity was included in CDR3 sequences. To manage the complexity of the libraries generated, the diversity introduced in the CDR3s was capped at 5000 (as shown in Table 4). Diversity repertoires were selected to represent biophysical properties of all amino acids, while avoiding residues and motifs that are likely to lead to developability liabilities. The scFv genes containing the described repertoire were cloned into the phagemid vector pADL23c (Antibody Design Labs) at the BglI restriction site. The diversified scFv was amplified in a 50 μl reaction solution containing 10 ng synthesis scFv as template, 25 pmol 5' and 3' primers, and 1 μl of Phusion high fidelity polymerase (NEB) for 30 cycles at 95° C. for 10 sec,

TABLE 5

| The quality control for the G8 phage display library | | | | | |
|---|---|---|---|---|---|
| G8 | Chain | % of functional clones | # of functional clones | Actual library size | Theoretical library size |
| Parent A | HC | 83 | 20/24 | 1.2E+09 | 9.0E+08 |
| | LC | 88 | 21/24 | 8.4E+08 | 1.6E+09 |

Example 2: Phage Display Panning

Before the first round of panning (P1), the phage library was depleted with Dynabead M-280 streptavidin beads (Life Technologies).

For the first round of panning (PI), 100 nM of peptide-HLA complex bound to streptavidin beads was incubated with phage for 1 hour at room temperature with rotation. Three five-minute washes with 0.5% BSA in 1×PBST (PBS+0.05% Tween-20) followed by three five-minute washes with 0.5% BSA in 1×PBS were utilized to remove any unbound phage to the peptide-HLA complex bound beads. To elute the bound phage from the washed beads, 1 mL 0.1M TEA was added and incubated for 10 minutes at room temperature with rotation. The eluted phage was collected from the beads and neutralized with 0.5 mL 1M Tris-HCl pH 7.5. The neutralized phage was then used to infect log growth TG-1 cells (OD600=0.5) and after an hour of infection at 37° C., cells were plated onto 2YT media with 100 μg/mL carbenicillin and 2% glucose (2YTCG) agar plates for output titer and bacterial growth for subsequent panning rounds.

For the second round, 1 nM of peptide-HLA complex bound to streptavidin beads was incubated with phage for 1 hour at room temperature with rotation. Three five-minute washes with 1×PBST (PBS+0.1% Tween-20) followed by three five-minute washes with 1×PBS were utilized to remove any unbound phage. To elute the bound phage from the washed beads, 0.5 mL 0.1M TEA was added and incubated for 10 minutes at room temperature with rotation. The eluted phage was collected from the beads and neutralized with 0.5 μL 1M Tris-HCl pH 7.5. The neutralized phage was then used to infect log growth TG-1 cells (OD600=0.5) and after an hour of infection at 37° C., cells were plated onto 2YT media with 100 μg/mL carbenicillin and 2% glucose (2YTCG) agar plates for output titer and bacterial growth for subsequent panning rounds.

For the third round of panning, 2 parallel depletion strategies were employed. Arm one (P3-1) involved deselecting the library against 100 nM of pooled negative peptide-HLA complexes where the peptides were similar peptides derived from the transcriptome. After washing 5 times with PBST, the phage was eluted with 0.5 mL of 0.1M TEA and neutralized with 1M HCl (pH 7.5).

In the second arm (P3-2), the round of library selection consisted of two selection steps with A375 cells as negative target cells and a positive selection on target pMHC engineering A475 cells. Non-specific phage on the cells were removed by washing the beads five times with PBS. To elute the bound phage from the cells, 0.5 mL of 0.2 M glycine HCl (pH 2.5) was added and incubated for 10 minutes at room temperature. The eluted phage was separated from the cells by centrifugation at 2000 g for 10 min. The phage-containing supernatants were neutralized with 0.1 mL 1M Tris-HCl pH 7.5. The neutralized phage were then used to infect log growth TG-1 cells ($OD_{600}$=0.5) for output titer.

Output Phage Determined by Tittering

Each round of output phage was serially diluted ($1:10^2$-$1:10^6$) in 2YT media and the diluted phage was infected with log phase SS320 cells. 100 μl of phage infected with SS320 was plated on 2YTCG and grown overnight at 30° C. to determine the titer of phage. The following formula was used to calculate total output phages in 2 ml:

$$\text{Output phage} = \text{Number of colonies on plate} \times$$
$$\text{dilution factor} \times 10 \times \text{volume of phage output (ml)}.$$

Preparation of Bacterial Supernatant and Periplasmic Extracts (PPE)

Individual colonies of SS320 were picked in 350 μL of Overnight Express Instant TB medium (Millipore sigma) plates, shaken (700 rpm) and grown overnight at 30° C. by shaking (700 rpm). Cells were pelleted by centrifugation for 10 min at 3000×g.

The periplasmic extracts were prepared by resuspending pellets from the overnight cultures in 60 ul BugBuster master mix (Millipore Sigma). The cell suspension was incubated on a shaking platform for 20 min at room temperature. Insoluble cell debris was removed by centrifugation at 3000×G for 20 min at 4° C. and supernatant was collected to be used in a binding assay by Meso Scale Discovery (MSD) platform.

Example 3: MSD Binding and Analysis of Affinity Matured Clones

G8 scFv screening was conducted using the Meso Scale Discovery U-PLEX Development Pack, 9-assay (cat. No. K15234N). The pack contains a 10-spot U-PLEX plate with 9 activated spots and 9 unique linkers as well as stop solution and read buffer. Biotinylated pHLA and biotinylated Protein L were each diluted to 33 nM using PBS+0.5% BSA. For each plate, 200 μL of the diluted pHLA or protein L was mixed with 300 μL of the corresponding Linker (see Table 9) and incubated at room temperature for 30 minutes.

TABLE 9

| A*02: 01 pHLA conjugation to unique linker for G8 antibody screening | |
|---|---|
| Linker | pHLA or Protein L |
| 1 | AIFPGAVPAA (SEQ ID NO: 42) |
| 2 | ALFPSGVPAA (SEQ ID NO: 53) |
| 3 | TVFPGAVPVL (SEQ ID NO: 54) |
| 4 | FIFPGLLPEA (SEQ ID NO: 55) |
| 5 | GIGPGGVAAA (SEQ ID NO: 56) |
| 7 | SAFAGAVRAA (SEQ ID NO: 57) |
| 10 | Protein L |

Following the 30-minute incubation, 200 μL stop solution was added to each linker-pHLA solution. They were again incubated for 30 minutes at room temperature. These volumes were scaled based on the number of plates. The linker-pHLA solutions were then a 10× solution. They were then pooled together and further diluted with stop solution to the final 1× concentration. For example, for one plate with one linker, 600 μL pHLA would be diluted with 5.4 mL stop solution for the 1× concentration with a total volume of 6 mL. For one plate using 8 linkers, 600 μL of each linker was pooled to give 4.8 mL volume and 1.2 mL additional stop solution added for the final 6 mL volume. All volumes were scaled for additional plates. The pooled linker-pHLA solution was then coated onto the 10-spot plate as 50 L/well, the plate sealed and stored at 4° C. overnight.

Samples, periplasmic extracts (PPE) were diluted 40-fold with PBS+1% BSA. The plate was washed 3 times with PBS+0.05% Tween and samples added as 50 μL/well. Plates were incubated at room temperature shaking for 2 hours. The plates were washed as before and 50 μL of 1 μg/mL SulfoTag anti-Myc tag (Abcam, ab206486) was added to each well. The anti-Myc tag antibody was sulfo-tag labeled using the MSD Gold Sulfo-tag NHS-Ester Conjugation kit (Meso Scale Discovery, R31AA-2) at a challenge ratio of 10. The plates were incubated for 1 hour shaking at room temperature. The plate wash was repeated and 150 μL 2× Read Buffer T (Meso Scale Discovery, R92TC-2) was added to all wells and the plate read immediately on the Quickplex SQ 120.

Purified antibody samples were tested in the same manner, except were serially diluted, and the detection antibody was 1 μg/mL SulfoTag labeled donkey anti-human Fc (Jackson ImmunoResearch, 709-005-098). Sulfotag labeling was performed as previously described.

Figure 2:
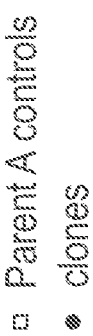
FIG. 2 includes a plot showing the relative affinity (as determined by Meso Scale Discovery (MSD)) of affinity matured clones versus the parent clone (Parent A control).
Figures 3A, 3B:
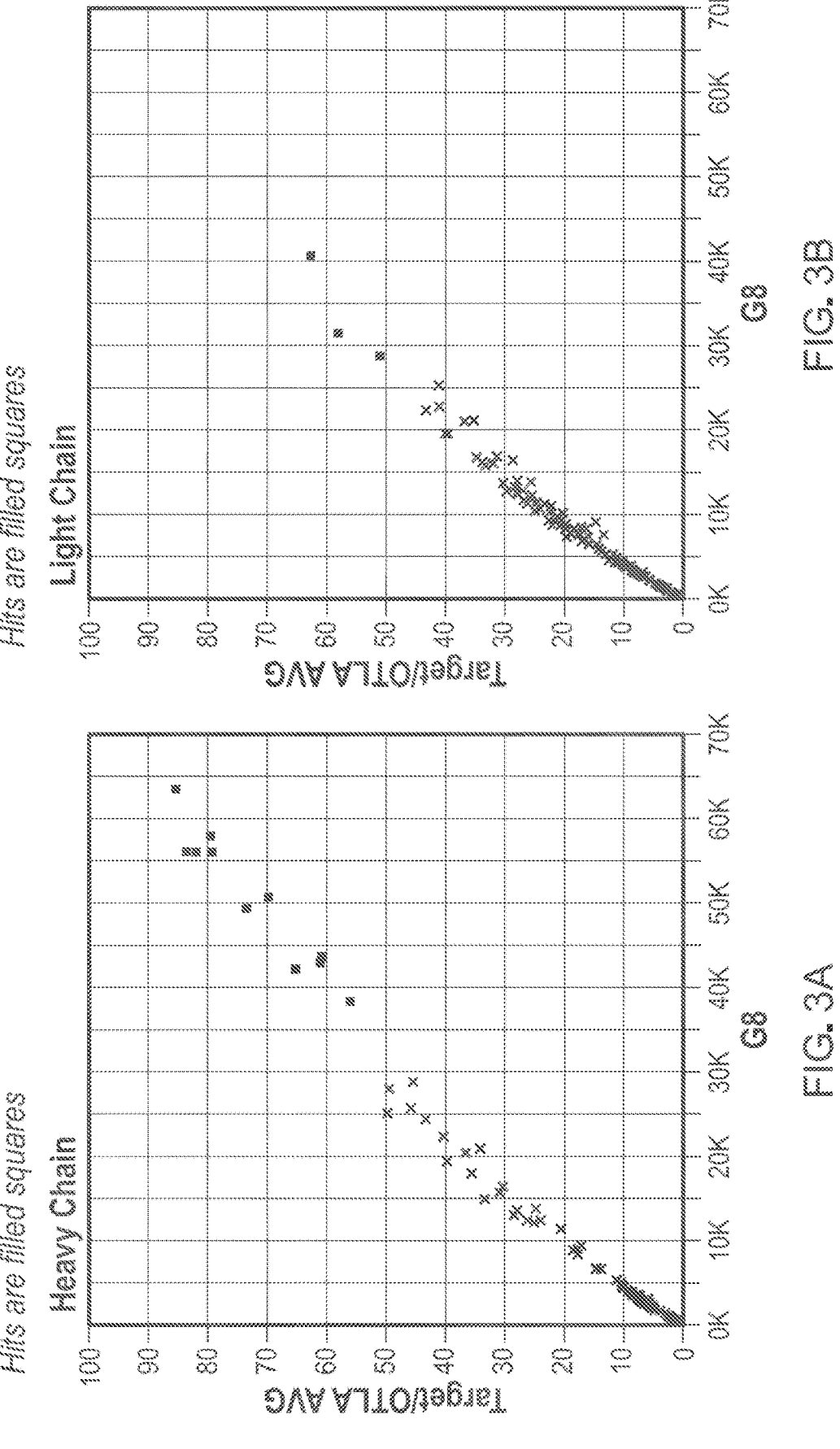
FIG. 3A includes a plot showing the relative affinity for pHLA targets (as determined by MSD) of affinity matured heavy chain clones. The filled squares highlight the clones designated "hit sequences" for high affinity.
FIG. 3B includes a plot showing the relative affinity for pHLA targets (as determined by MSD) of affinity matured light chain clones. The filled squares highlight the clones designated "hit sequences" for high affinity.

The results of the MSD binding analysis, as shown in FIGS. 2, 3A, and 3B, revealed that some of the affinity-matured Parent A-heavy and -light chain clones exhibited stronger relative affinity for the pHLA target than the Parent A controls.

Figures 4A, 4B:
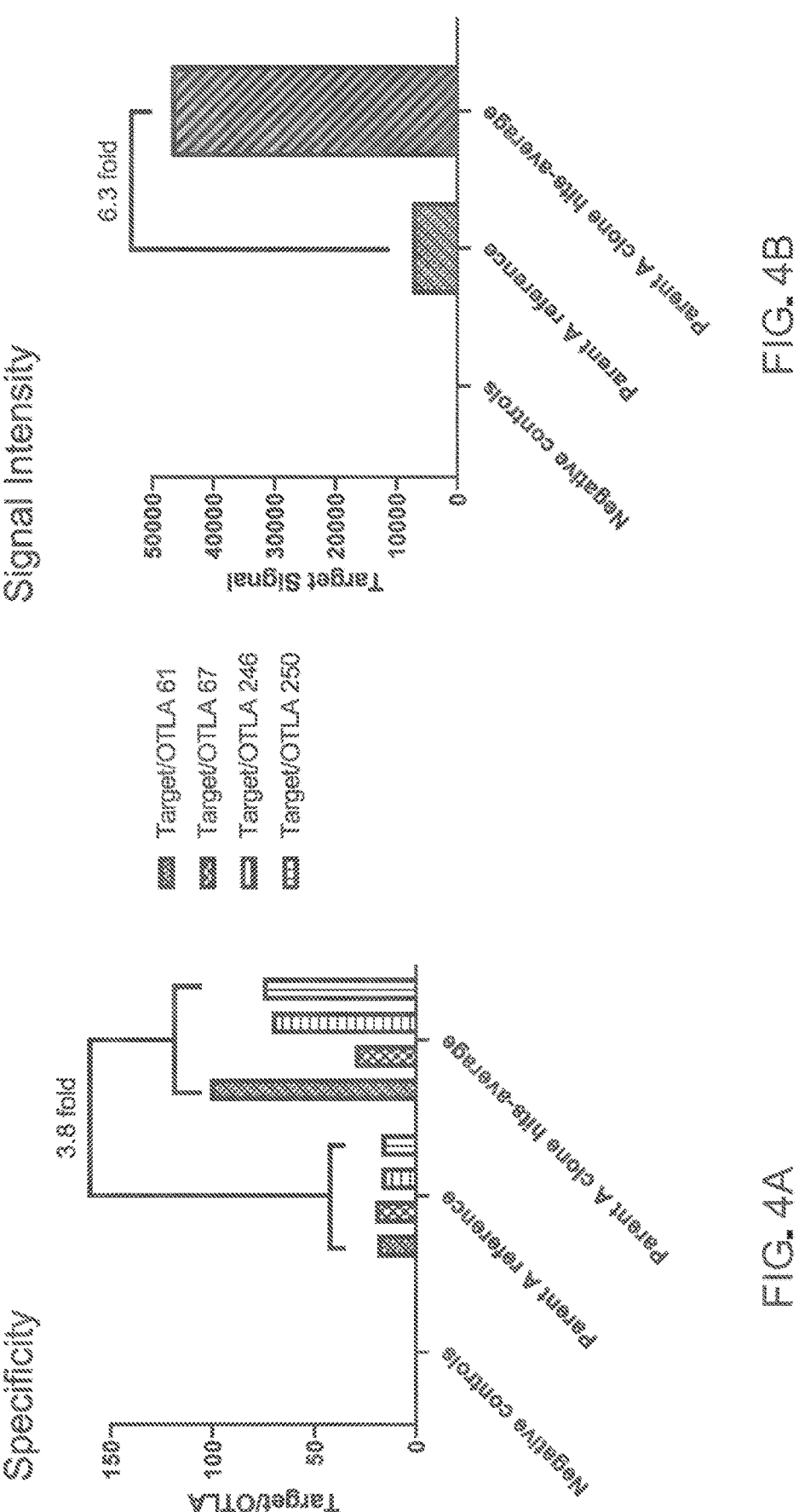
FIG. 4A includes a chart showing the average specificity for pHLA target (as determined by MSD) for the affinity matured hit sequences versus the Parent A controls and negative controls.
FIG. 4B includes a chart showing the signal intensity for pHLA target (as determined by MSD) for the affinity matured hit sequences versus the Parent A controls and negative controls.

The specificity and signal intensity for clones identified as hits (see FIGS. 4A and 4B) were compared to the Parent A controls. Expression levels for clones were within approximately 15% of expression levels for controls based on Protein L binding in the MSD assay. On average, the clones identified as hits exhibited about 3.8-fold greater specificity for the pHLA target than the Parent A controls (See FIG. 4A). The average specificity for hit clones and the Parent A clones is also shown in Table 13. On average, the clones identified as hits exhibited about 6.3-fold greater signal intensity for target than the Parent A controls (see FIG. 4B).

TABLE 13

| Average Specificity for affinity matured hits. | | | | | |
|---|---|---|---|---|---|
| | Target/ OTLA 61 | Target/ OTLA 67 | Target/ OTLA 246 | Target/ OTLA 250 | Average Target/ OTLA |
| Negative control | 1 | 2 | 1 | 1 | 1 |
| Parent A reference | 19 | 20 | 17 | 17 | 18 |
| Parent A hits average | 103 | 24 | 72 | 78 | 69 |

Example 4: Reformatting of scFv for Functional Testing (Format 6; 2+2 Bivalent Bispecific Antibody) and Production of Supes in HTS Reformatting to Format 6 Antibodies:

G8 scFvs were PCR amplified from phagemid using primers containing a 3'gene-specific portion and a common 5' tail sequence to add a flanking recombination site to the fragments, forward 5'-CTTTCTCTCCACAGGTGTA-CACTCCGAGGTTCAGCTCCTGGAG-3' (SEQ ID NO: 58) and reverse 5'-AGAGCCCCCTCCGCCG-GATCCCCCTCCGCCCTTGATGTCCACCTTAG-3' (SEQ ID NO: 59). The scFv was amplified with Phusion® High-Fidelity PCR Master Mix with GC Buffer (New England Biolabs) using 10 μg of purified phagemid by PCR, and then treated with DpnI (New England Biolabs). The PCR product was size verified by electrophoresis and the scFv PCR product was purified using a spin-column. pcDNA3.1(−) containing an scFv appended to the N-terminus of an anti-CD3 HC was used as a receiving vector to generate a format 6 antibody (see, for example, FIG. 5 and the methods provided in Example 10). The receiving vector was linearized with BsrG1 and BamHI (New England Biolabs), and gel purification was performed a using QIAEXII Gel Extraction Kit (Qiagen). Cloning was performed using the In-Fusion® HD Cloning Kit (Takara Bio) with the scFv insert and the linearized plasmid in a 2:1 molar ratio. In-fusion reactions were transformed into Stellar Competent cells (Takara Bio) and plated on LB agar plates containing 100 ug/mL of carbenicillin. Positive clones were identified by rolling circle amplification sequencing, then isolated by miniprep and used for transfection into Expi293 cells.

HTS Transfection Materials and Methods

Materials:

Expi293 Expression system kit 96-round well microtiter block plates (2 ml capacity per well, U-shaped bottoms)

PureLink Air porous tape

37° C. CO₂ incubator

Methods:

Preparing Cells—

Expi 293 cells were maintained as directed in the system manual. On day 0, the cells were seeded at 2.0×10⁶ viable cells/ml.

On the day of transfection, cells were diluted to 2.8×10⁶ viable cells/ml using Expi293 expression medium and 700 μl of cells were added to each well in the 96 well plate.

Preparing Transfection Complex—

For each well to be transfected, lipid-DNA complex was prepared as follows: 0.8 ug of G8 plasmid DNA was added to 35 μl of OptiMEM-I and was mixed gently.

In a separate plate per well, 1.9 μl of Expifetamine 293 reagent was added to 35 μl of OptiMEM-I and was gently mixed and incubated for 5 mins. Then the diluted plasmid DNA was added to the diluted Expifectamine293 reagent and was mixed gently.

This mixture was incubated at room temperature for 20 mins to allow the DNA-Expifectamine 293 reagent complex to form.

Transfection of Cells—

70 μl of the above complex was added to each well by gentle mixing.

The plate was sealed with microporous film and the plate was clipped in the plate shaker. The speed was set to 1000 rpm at 37° C. tissue culture incubator with 8% CO₂.

Addition of Enhancers—

At 18-24 hours post transfection, the plates were removed.

3.5 μl of Enhancer1 was mixed with 35 μl of Enhancer2 per well.

38.5 μl of the Enhancer cocktail was added to the cells.

Plate was resealed and the cells were incubated for 3 more days.

Harvesting of Cells—

Cells were harvested on Day 4 by spinning it in the centrifuge at 500×g for 5 minutes.

Example 5: Cytotoxicity Screening of Supes and Further Selection of Sequences

The engineered bispecifics bound cells that present the target peptide-HLA and CD3+ Jurkat cells. After reformatting the T-Cell Receptor mimic (TRCm) antibody into various bispecific formats, their ability to bind the specific pHLA target as well as CD3+ Jurkats was tested. Therefore, titration experiments were conducted on K-562 cells that were transduced HLA-A*02:01 and exogenously pulsed with target or negative control peptide. Target specific binding was also tested on A375 cells transduced with high or medium levels of target as well as A375 transduced with control construct. Bispecific binding was detected by flow cytometry. All formats tested bound in a dose-dependent manner that was selective for the relevant target peptide on all cells. In addition, all formats bound to CD3+, but not CD3-, Jurkat cell lines. This interaction is presumably through the anti-CD3 portion of the bispecific molecules.

K-562 Cell Line Generation:

The Phoenix-AMPHO cells (ATCC®, CRL-3213™) were cultured in DMEM (Corning™, 17-205-CV) supplemented with 10% FBS (Seradigm, 97068-091) and Gluta-max (Gibco™, 35050079). K-562 cells (ATCC®, CRL-243™) were cultured in IMDM (Gibco™, 31980097) supplemented with 10% FBS. Lipofectamine LTX PLUS (Fisher Scientific, 15338100) contains a Lipofectamine reagent and a PLUS reagent. Opti-MEM (Gibco™, 31985062) was purchased from Fisher Scientific.

Phoenix cells were plated at 5*10e5 cells/well in a 6 well plate and incubated overnight at 37° C. For the transfection, 10 ug plasmid, 10 μL Plus reagent and 100 μL Opti-MEM were incubated at room temperature for 15 minutes. Simultaneously, 8 μL Lipofectamine was incubated with 92 μL Opti-MEM at room temperature for 15 minutes. These two reactions were combined and incubated again for 15 minutes at room temperature after which 800 μL Opti-MEM was added. The culture media was aspirated from the Phoenix cells and they were washed with 5 mL pre-warmed Opti-MEM. The Opti-MEM was aspirated from the cells and the lipofectamine mixture was added. The cells were incubated for 3 hours at 37° C. and 3 mL complete culture medium was added. The plate was then incubated overnight at 37° C. The media was replaced with Phoenix culture medium and the plate incubated an additional 2 days at 37° C.

The media was collected and filtered through a 0.45 μm filter into a clean 6 well dish. 20 μL Plus reagent was added to each virus suspension and incubated at room temperature for 15 minutes followed by the addition of 8 μL/well of Lipofectamine and another 15 min room temperature incubation. K-562 cells were counted and resuspended to 5E6 cells/mL and 100 μL added to each virus suspension. The 6 well plate was centrifuged at 700 g for 30 minutes and then incubated at 37° C. for 5-6 hours. The cells and virus suspension were then transferred to a T25 flask and 7 mL K-562 culture medium was added. The cells were then incubated for three days. The transduced K-562 cells were then cultured in medium supplemented with 0.6 μg/mL Puromycin (Invivogen, ant-pr-1) and selection monitored by flow cytometry.

Flow Cytometry Methods:

HLA-transduced K-562 cells were pulsed the night before with 50 μM of peptide (Genscript) in IMEM containing 1% FBS in 6 well plates and incubated overnight under standard tissue culture conditions. Cells were harvested, washed in PBS, and stained with eBioscience Fixable Viability Dye eFluor 450 for 15 minutes at room temperature. Following another wash in PBS+2% FBS, cells were resuspended with bispecifics at varying concentrations. Cells were incubated with bispecifics for 1 hour at 4° C. After another wash, PE-conjugated goat anti-human IgG secondary antibody (Jackson ImmunoResearch) was added at 1:100. After incubating at 4 C for 45 minutes and washing in PBS+2% FBS, cells were resuspended in PBS+2% FBS and analyzed by flow cytometry. Flow cytometric analysis was performed on the Attune NxT Flow Cytometer (ThermoFisher) using the Attune NxT Software. Data was analyzed using FlowJo. Jurkat E6-1 (ATCC TIB-152) and Jurkat T3.5 (ATCC TIB-153) cells were grown under standard tissue culture conditions. The target engineered A375 cell lines as well as the Jurkats were stained and analyzed with bispecific binding using the same method as the K-562 cells.

Cytotoxicity Assays:

Cytotoxicity Screening of Unpurified Supernatants Containing Bispecific Variants Target were plated at 10,000 cells per well of 96 well plate. Target cell lines were A375 transduced with a 10×10 mer cassette expressing the target peptide and luciferase and the A375 cell line expressing the FOXE1 gene and luciferase. After allowing the cells to adhere for 4 hours, human CD3 T cells (Stem Cell Technologies) were added at a ratio of 5:1 effector to target cells. Crude supernatants from Exip293 cells expressing the bispecific antibodies were added to the wells at indicated final concentration and indicated dilutions. Cultures were incubated for three days. Luciferase signal was assessed using Promega's Bio-Glo assay system (Cat. #G7941) according to manufacturer's instructions and read on the SpectraMax M5. Signal was normalized to control wells which had crude supe from untransfected cell culture to determine the percent of cyto-toxicity. Loss of luciferase signal was interpreted as loss of cell viability.

Testing Cytotoxicity of Purified Bispecifics

Target and control cells were plated at 10,000 cells per well of 96 well plate. Target cell lines were A375 transduced with a 10×10 mer cassette expressing the target peptide and luciferase and the A375 cell line expressing the FOXE1 gene and luciferase. The A375 cell lines transduced with luciferase only serves as a negative control. After allowing the cells to adhere for 4 hours, human CD3 T cells (Stem Cell Technologies) were added at a ratio of 5:1 effector to target cells. Bispecific antibody was added to the well at indicated final concentration. Cultures were incubated for three days. Luciferase signal was assessed using Promega's Bio-Glo assay system (Cat. #G7941) according to manufacturer's instructions and read on the SpectraMax M5. Signal was normalized to control wells to determine the percent of cytotoxicity. Loss of luciferase signal was interpreted as loss of cell viability.

Large Scale Transfection of Antibodies

Antibodies were expressed transiently using the Expi293 expression system (Life Technologies), and harvested on day 5. Harvested cell culture fluid was clarified by centrifugation (4000×g, 20 min) followed by 0.45 um and 0.2 um filtration.

Several of the bispecific antibodies exhibited high cytotoxicity at low concentrations. Twelve hit clones were selected based on high cytotoxicity against the tested A375 cells lines (see Table 14). The threshold for selection of those 12 hit clones was greater than 50 target/OTLA specificity.

TABLE 14

| Unique Clone | HC_CDR1 | HC_CDR2 | HC_CDR3 | LC_CDR1 | LC_CDR2 | LC_CDR3 |
|---|---|---|---|---|---|---|
| | Clones selected during the cytotoxicity screen of supes | | | | | |
| 05D07 | DYYMSGINWYSGST (SEQ ID NO: 16) | GYADSVKG (SEQ ID NO: 17) | VEQGYDIY YYYYMDV (SEQ ID NO: 27) | RASQSIS SYLN (SEQ ID NO: 28) | KASS LES (SEQ ID NO: 30) | QQSYSAP YT (SEQ ID NO: 32) |
| 09G01 | DYYMSVINWPGSST (SEQ ID NO: 16) | GYADSVKG (SEQ ID NO: 18) | VEQGYDIY YYYYMDV (SEQ ID NO: 27) | RASQSIS SYLN (SEQ ID NO: 28) | KASS LES (SEQ ID NO: 30) | QQSYSAP YT (SEQ ID NO: 32) |
| 05G06 | DYYMSGINWPGGST (SEQ ID NO: 16) | GYADSVKG (SEQ ID NO: 19) | VEQGYDIY YFYYMDV (SEQ ID NO: 34) | RASQSIS SYLN (SEQ ID NO: 28) | KASS LES (SEQ ID NO: 30) | QQSYSAP YT (SEQ ID NO: 32) |
| 09D01 | DYYMSGINWHHGST (SEQ ID NO: 16) | GYADSVKG (SEQ ID NO: 20) | VEQGYDIY YYYYMDV (SEQ ID NO: 27) | RASQSIS SYLN (SEQ ID NO: 28) | KASS LES (SEQ ID NO: 30) | QQSYSAP YT (SEQ ID NO: 32) |
| 05G09 | DYYMSGINWPGGST (SEQ ID NO: 16) | DYADSVKG (SEQ ID NO: 21) | VEQGYDIY YYYYMDV (SEQ ID NO: 27) | RASQSIS SYLN (SEQ ID NO: 28) | KASS LES (SEQ ID NO: 30) | QQSYSAP YT (SEQ ID NO: 32) |

TABLE 14-continued

Clones selected during the cytotoxicity
screen of supes

| Unique Clone | HC_CDR1 | HC_CDR2 | HC_CDR3 | LC_CDR1 | LC_CDR2 | LC_CDR3 |
|---|---|---|---|---|---|---|
| 09D06 | DYYMSGINWPGSST (SEQ ID NO: 16) | VRQGYDYY GYADSVKG (SEQ ID NO: 22) | RASQSIS SYLN (SEQ ID NO: 28) | KASS LES (SEQ ID NO: 30) | QQSYSAP YT (SEQ ID NO: 32) |
| 05A08 | DYYMSNINWNGGST (SEQ ID NO: 16) | VEQGYDNY LYADSVKG (SEQ ID NO: 23) | RASQSIS SYLN (SEQ ID NO: 28) | KASS LES (SEQ ID NO: 30) | QQSYSAP YT (SEQ ID NO: 32) |
| 05A03 | DYYMSGINWPGGST (SEQ ID NO: 16) | VEQGYDIY GYADSVKG (SEQ ID NO: 19) | RASQSIS SYLN (SEQ ID NO: 28) | KASS LES (SEQ ID NO: 30) | QQSYSAP YT (SEQ ID NO: 32) |
| 05C04 | DYYMSGINWPGGYT (SEQ ID NO: 16) | VEQGYDIY GYADSVKG (SEQ ID NO: 24) | RASQSIS SYLN (SEQ ID NO: 28) | KASS LES (SEQ ID NO: 30) | QQSYSAP YT (SEQ ID NO: 32) |
| 05D10 | DYYMSGINWPGSST (SEQ ID NO: 16) | VEQGYDIY GYADSVKG (SEQ ID NO: 22) | RASQSIS SYLN (SEQ ID NO: 28) | KASS LES (SEQ ID NO: 30) | QQSYSAP YT (SEQ ID NO: 32) |
| 09D04 | DYYMSGINWPGYST (SEQ ID NO: 16) | VEQGYDNY GYADSVKG (SEQ ID NO: 25) | RASQSIS SYLN (SEQ ID NO: 28) | KASS LES (SEQ ID NO: 30) | QQSYSAP YT (SEQ ID NO: 32) |
| 06D07 | DYYMSGINWNGGST (SEQ ID NO: 16) | VEQGYDIY GYADSVKG (SEQ ID NO: 26) | RASQSIH SYLN (SEQ ID NO: 29) | KAST PYS (SEQ ID NO: 31) | QQSYSYP HN (SEQ ID NO: 33) |

Figure 6:
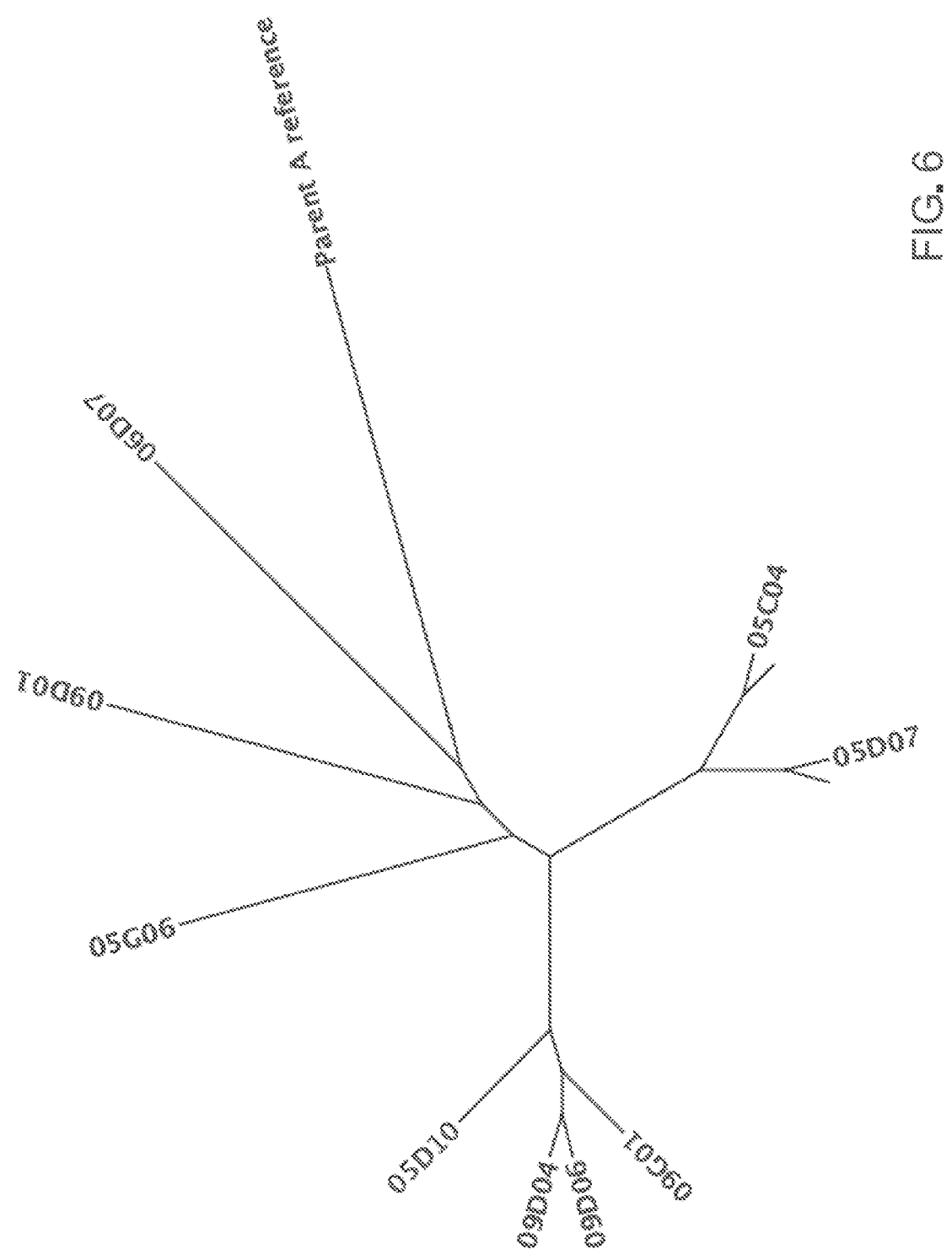
FIG. 6 includes a cladogram of the hit sequences and the Parent A clone showing the degree of sequence diversity between the indicated clones.

Thereafter, 8 unique clones were moved forward based on cytotoxicity and degree of sequence diversity. The results of the cytotoxicity experiments are shown in Tables 15 and 16. Tables 15-17 show the 8 clones (highlighted) that were selected based on these criteria. FIG. 6 depicts the degree of sequence diversity between the 8 unique clones.

TABLE 15

Hits based on cytotoxicity against A375-G8-10mer cell line

| Name | Unique Clone | µg/ml BiSp | Percent cyto-toxicity (listed concen-tration) | percent cyto-toxicity (10X diluted) | percent cyto-toxicity (100x diluted) |
|---|---|---|---|---|---|
| 1 | 05A03 | 0.010625 | 97.37 | 79.59 | 35.31 |
| 2 | 05A08 | 0.00355 | 39.98 | 8.84 | −0.42 |
| 3 | 05C04 | undetectable | 0.16 | 4.39 | −3.88 |
| 4 | 05D07 | 0.003175 | 54.71 | 8.35 | −2.23 |
| 5 | 05D10 | 0 | 46.23 | 6.46 | −5.66 |
| 6 | 05G06 | undetectable | 5.32 | 4.32 | −3.37 |
| 7 | 06D07 | 0.0085 | 21.23 | 3.24 | −5.90 |
| 8 | 09D01 | 0.0094 | 54.17 | 3.73 | −10.37 |
| 9 | 09D04 | 0.00255 | 96.54 | 42.36 | 3.62 |
| 11 | 09G01 | 0.01215 | 97.53 | 95.95 | 54.91 |

TABLE 16

Hits based on cytotoxicity against A375-FOXE1 cell line

| Name | Unique Clone | µg/ml BiSp | Percent cyto-toxicity (listed concen-tration) | percent cyto-toxicity (10X diluted) | percent cyto-toxicity (100x diluted) |
|---|---|---|---|---|---|
| 1 | 05A03 | 0.010625 | 97.91 | 32.40 | 35.31 |
| 2 | 05A08 | 0.00355 | 9.31 | 9.37 | −0.42 |
| 3 | 05C04 | undetectable | −4.28 | 7.73 | −3.88 |
| 4 | 05D07 | 0.003175 | 3.69 | 9.32 | −2.23 |
| 5 | 05D10 | 0 | 5.33 | 9.98 | −5.66 |
| 6 | 05G06 | undetectable | 2.23 | 12.70 | −3.37 |
| 7 | 06D07 | 0.0085 | 15.76 | 9.17 | −5.90 |
| 8 | 09D01 | 0.0094 | 9.12 | 1.88 | −10.37 |
| 9 | 09D04 | 0.00255 | 92.63 | 20.09 | 3.62 |
| 11 | 09G01 | 0.01215 | 98.16 | 92.61 | 54.91 |

TABLE 17

Eight unique hits selected based on cytotoxicity and sequence diversity

| Name | Unique Clone | EC50 (fM) A375_10mer | EC50 (fM) A375_FOXE1 | Heavy CDR1 | Heavy CDR2 | Heavy CDR3 | Light CDR1 | Light CDR2 | Light CDR3 |
|---|---|---|---|---|---|---|---|---|---|
| 60 | Parent A | | | DYYMS (SEQ ID NO: 16) | GINWNGGSTGYADSV KG (SEQ ID NO: 26) | VEQGYDIYYYYYMD V (SEQ ID NO: 27) | RASQSISSYL N (SEQ ID NO: 28) | KASSLES (SEQ ID NO: 30) | QQSYSAPYT (SEQ ID NO: 32) |
| 1 | 05A03 | 64 | 129 | DYYMS (SEQ ID NO: 16) | GINWPGGSTGYADSV KG (SEQ ID NO: 19) | VEQGYDIYYYYYMD V (SEQ ID NO: 27) | RASQSISSYL N (SEQ ID NO: 28) | KASSLES (SEQ ID NO: 30) | QQSYSAPYT (SEQ ID NO: 32; |

TABLE 17-continued

| | | | | | | | | | |
|---|---|---|---|---|---|---|---|---|---|
| Name | Unique Clone | EC50 (fM) A375_ 10mer | EC50 (fM) A375_ FOXE1 | Heavy CDR1 | Heavy CDR2 | Heavy CDR3 | Light CDR1 | Light CDR2 | Light CDR3 |
| 4 | 05D07 | 56 | 410 | DYYMS (SEQ ID NO: 16) | GINWYSGSTGYADSV KG (SEQ ID NO: 17) | VEQGYDIYYYYYMD V (SEQ ID NO: 27) | RASQSISSYL N (SEQ ID NO: 28) | KASSLES (SEQ ID NO: 30) | QQSYSAPYT (SEQ ID NO: 32) |
| 5 | 05D10 | 69 | 168 | DYYMS (SEQ ID NO: 16) | GINWPGSSTGYADSV KG (SEQ ID NO: 22) | VEQGYDIYYYYYMD V (SEQ ID NO: 27) | RASQSISSYL N (SEQ ID NO: 28) | KASSLES (SEQ ID NO: 30) | QQSYSAPYT (SEQ ID NO: 32) |
| 6 | 05G06 | 112 | 1475 | DYYMS (SEQ ID NO: 16) | GINWPGGSTGYADSV KG (SEQ ID NO: 19) | VEQGYDIYYFYYMD V (SEQ ID NO: 34) | RASQSISSYL N (SEQ ID NO: 28) | KASSLES (SEQ ID NO: 30) | QQSYSAPYT (SEQ ID NO: 32) |
| 7 | 06D07 | 1842 | 4777 | DYYMS (SEQ ID NO: 16) | GINWNGGSTGYADSV KG (SEQ ID NO: 26) | VEQGYDIYYYYYMD V (SEQ ID NO: 27) | RASQSIHSYL N (SEQ ID NO: 29) | KASTPYS (SEQ ID NO: 31) | QQSYSYPH N (SEQ ID NO: 33) |
| 8 | 09D01 | 162 | 6556 | DYYMS (SEQ ID NO: 16) | GINWHHGSTGYADSV KG (SEQ ID NO: 20) | VEQGYDIYYYYYMD V (SEQ ID NO: 27) | RASQSISSYL N (SEQ ID NO: 28) | KASSLES (SEQ ID NO: 30) | SEQ ID NO: 32 |
| 9 | 09D04 | 35 | 43 | DYYMS (SEQ ID NO: 16) | GINWPGSSTGYADSV KG (SEQ ID NO: 22) | VRQGYDYYYYYYMD V (SEQ ID NO: 35) | RASQSISSYL N (SEQ ID NO: 28) | KASSLES (SEQ ID NO: 30) | QQSYSAPYT (SEQ ID NO: 32) |
| 11 | 09G01 | 12 | 38 | DYYMS (SEQ ID NO: 16) | VINWPGSSTGYADSV KG (SEQ ID NO: 18) | VEQGYDIYYYYYMD V (SEQ ID NO: 27) | RASQSISSYL N (SEQ ID NO: 28) | KASSLES (SEQ ID NO: 30) | QQSYSAPYT (SEQ ID NO: 32) |

Example 6: Generation of Purified Antibodies

Antibody samples were purified using 5 mL MabSelect™ Sure Protein A HiTrap™ Column (Cytiva P/N11003493) at 5 ml/min flowrate on GE AKTA Avant. Column was initially equilibrated with 5 column volumes (CV) of Dulbecco's Phosphate Buffered Saline (DPBS) with calcium and magnesium (Corning P/N 21-030-CM), loaded with harvested supernatant, washed with 10 CVs of DPBS, and then eluted with 0.2 M Glycine, pH 3.0 (Alfa Aesar P/N J67349). The eluate was neutralized with 1/10 by volume of 1.0 M Tris, pH 8.0 (Alfa Aesar P/N J62726). The eluate was then loaded to the AKTA with the same condition as above to remove Knob-Knob homodimers using Kappa Select HiTrap™ Column (Cytiva 17545811). Both columns were washed with 5 CV of 100 mM NaOH after elution step. Lastly, the aggregates were removed using a mixed mode chromatography on AKTA with the same flowrate at 5 ml/min using Foresight™ CHT™ Type II 5 mL Column (Bio-Rad P/N 7324756) and running at 0 to 20% of 10×PBS gradient. Prior to the gradient, the Foresight™ CHT™ Type II column was equilibrated with 10 CV of 0.5×PBS, and finally washed with 5 CV of 100 mM NaOH after sample gradient elution.

Methods for purifying antibodies (e.g. bispecific antibodies) are also described in U.S. Provisional Application No. 63/058,461, the relevant disclosures of which are herein incorporated by reference.

Purified antibodies having the 8 unique hit sequences were evaluated for binding CD3 and pHLA on cells, binding to pHLA by Octet, and cytotoxicity.

Example 7: Cell Binding to pHLA

To examine the cell binding of the 8 unique hit sequences to their HLA-PEPTIDE targets in their natural context, e.g., on the surface of antigen-presenting cells; the format 6 antibodies generated from the 8 unique hit sequences were used in binding experiments with K-562 cells expressing the HLA-PEPTIDE target. Briefly, the cell binding experiment utilized K-562 cells that were transduced with HLA-A*02: 01 and exogenously pulsed with target or negative control peptide, using the methods described in Example 3. Bispecific binding was detected by flow cytometry.

Figure 7:
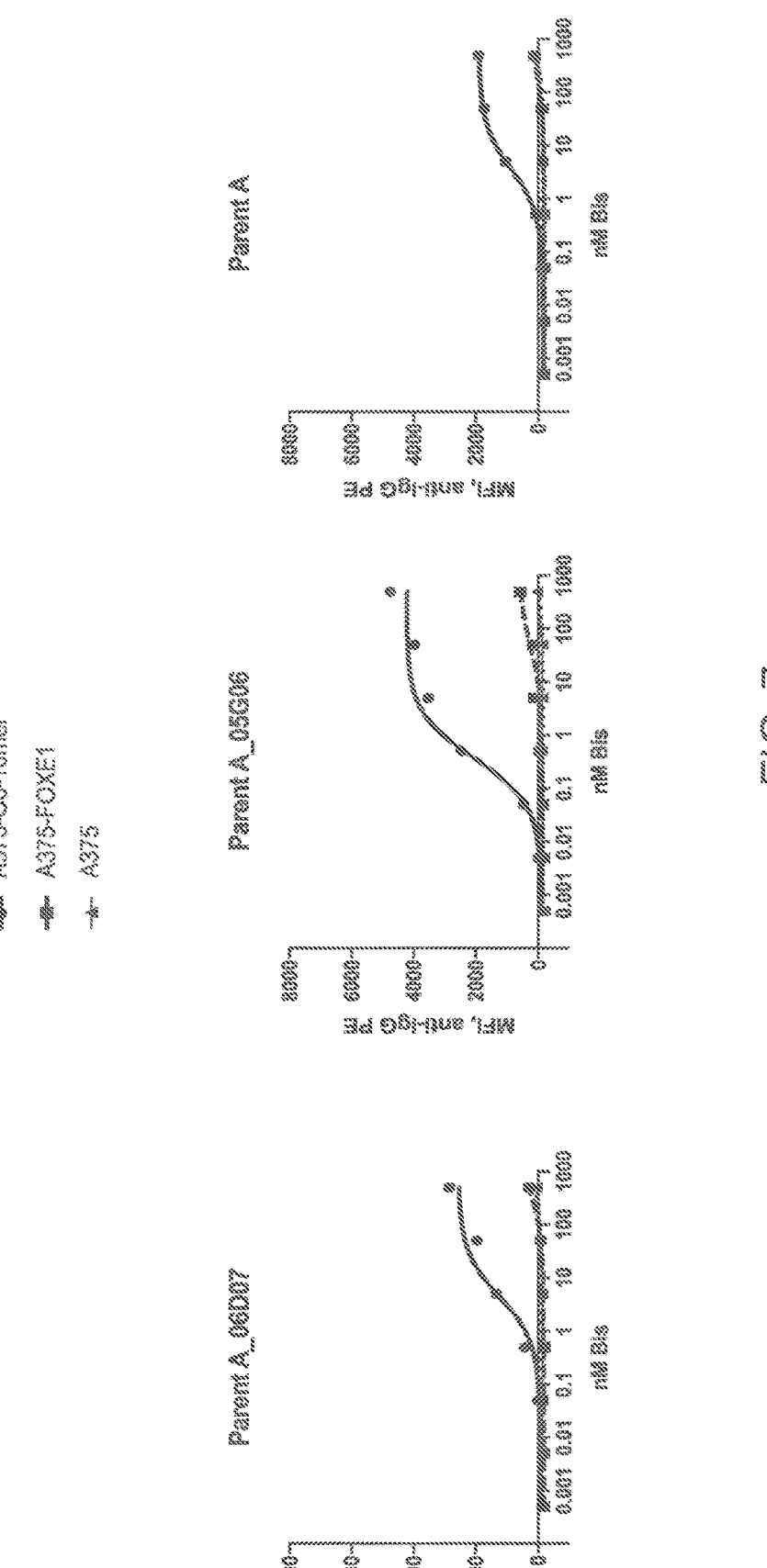
FIG. 7 includes plots showing the cell binding to target-expressing cells of affinity matured clones and the Parent A clone.

The results, as shown in FIG. 7, revealed that the selected affinity matured clones had stronger binding to pHLA expressing cells than non-pHLA expressing cells.

Example 8: Binding to pHLA by BLI/Octet

The affinity of the 8 unique hit antibodies to pHLA is measured using ForteBioOctet HTX in 96-channel mode with biolayer interferometry (BLI) detection. High Precision Streptavidin SAX biosensors (P/N 18-5117) are loaded into the instrument. Biotinylated G8-pHLA is captured on the SAX biosensor at 2 μg/mL and run for 120s in the assay buffer composed of 0.02% Tween-20 and 0.1% BSA. The biosensors are then dipped in assay buffer for a baseline. Subsequently, the biosensors are dipped into wells containing varying concentrations of the bispecific antibody samples (3.125, 6.25, 12.5, 25, 50, 100 and 200 nM) to measure the association rate for 50 seconds. The biosensors are finally dipped into wells containing assay buffer to measure the dissociation rate for another 50 seconds. Referencing is completed by having a biosensor with no immobilized ligand dipped into analyte. Kinetic data is processed with Octet™ software using a 1:1 kinetic model with errors within 10%, X2 below 3, and R2 above 0.9.

Example 9: Cytoxicity Measurements of Selected Affinity Matured Clones

To evaluate the cytotoxicity of the affinity matured clones, three clones (Parent A, 06D07, and 04A11) were examined using the cytotoxicity assay (see methods in Example 5). The CDR sequences for affinity matured clone 04A11 are provided in Table 18. 04A11 is synonymous with clone 05G06 and has the same VH and VL sequences as indicated by the CDRs in Table 18.

01_EVDPIGHVY (SEQ ID NO: 62), A*02:01_AIFP-GAVPAA (SEQ ID NO: 42), or A*01:01_ASSLPTTMNY (SEQ ID NO: 63).

Briefly, bispecific antibodies were generated using standard molecular cloning techniques, including restriction digestion and ligation, gene synthesis, and homology-based cloning methods such as In-fusion (Takara). Positive clones were confirmed by DNA sequencing and used to generate bispecific antibody molecules by transfecting Expi-CHO cells (Thermo) according to the manufacturer's protocol.

TABLE 18

The CDR sequences for affinity matured clone 04A11 (05G06).

| Name | Clone | EC50 (fM) A375_ 10mer | EC50 (fM) A375_ FOXE1 | Heavy CDR1 | Heavy CDR2 | Heavy CDR3 | Light CDR1 | Light CDR2 | Light CDR3 |
|---|---|---|---|---|---|---|---|---|---|
| 15 | 04A11 (05G06) | 112 | 1475 | DYYMS (SEQ NO: 16) | GINWPGGSTGYAD SVKG (SEQ ID NO: 19) | VEQGYDIYYF YYMDV (SEQ ID NO: 34) | RASQSISSYLN (SEQ ID NO: 28) | KASSLES (SEQ ID NO: 30) | QQSYSAPYT (SEQ ID NO: 32) |

Figure 8:
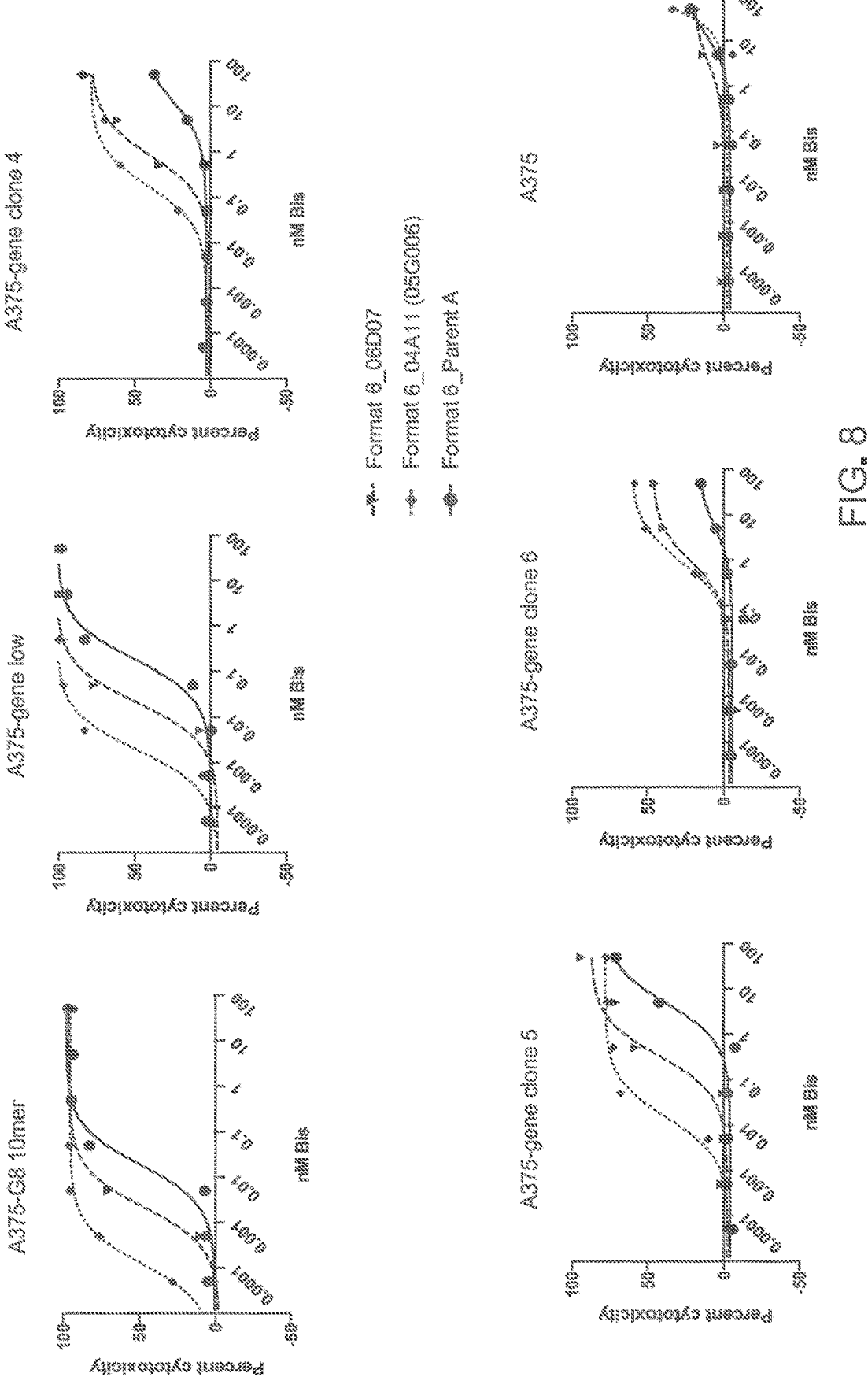
FIG. 8 includes plots showing the cytotoxicity against target-expressing cells of affinity matured clones and the Parent A clone.

The results, as shown in FIG. 8, revealed that the affinity matured clones 06D07 and 04A11 (05G06) exhibit higher cytotoxicity than the Parent A control clone, and the affinity matured clone 06D07 exhibited the highest cytotoxicity of the groups.

Example 10: Generation of Bispecific Antibodies that Specifically Bind an HLA-PEPTIDE Target and CD3

Antigen binding domains specific for various combinations of distinct targets were formatted into six bispecific construct designs (also referred to herein as formats). See International Application No. PCT/US2020/15736, which is hereby incorporated by reference in its entirety. For clarity, for designs (Formats) #2-#6, the antigen binding domains are attached, directly or indirectly, to an Fc region. Format #3, #4, and #5 optionally comprise knob-hole or other Fc heterodimerization modification(s). Format #2 and #6 optionally comprise WT IgG1 Fc sequences without knob-hole modification(s). In some embodiments, target 1 is the HLA-PEPTIDE target and target 2 is a cell surface molecule present on a T cell or NK cell. In some embodiments, target 2 is CD3. The antigen binding domain specific for CD3 can comprise CDRs or variable regions from any anti-CD3 antibody or antigen binding fragment thereof. In some embodiments, target 2 is CD16. In some embodiments, target 1 is an HLA-PEPTIDE target listed in Table A. In particular embodiments, target one is A*01:01_NTDNN-LAVY (SEQ ID NO: 60), A*02:01_LLASSILCA (SEQ ID NO: 61), B*35:01_EVDPIGHVY (SEQ ID NO: 62), A*02: 01_AIFPGAVPAA (SEQ ID NO: 42), or A*01:01_AS-SLPTTMNY (SEQ ID NO: 63). In more particular embodiments, the antigen binding domain for target 1 (the HLA-PEPTIDE target) comprises CDR sequences from any one of the scFvs specific for A*01:01_NTDNNLAVY (SEQ ID NO: 60), A*02:01_LLASSILCA (SEQ ID NO: 61), B*35: 01_EVDPIGHVY (SEQ ID NO: 62), A*02:01_AIFP-GAVPAA (SEQ ID NO: 42), or A*01:01_ASSLPTTMNY (SEQ ID NO: 63). In yet more particular embodiments, the antigen binding domain for target 1 (the HLA-PEPTIDE target) comprises the VH and VL sequences from any one of the scFvs specific for A*01:01_NTDNNLAVY (SEQ ID NO: 60), A*02:01_LLASSILCA (SEQ ID NO: 61), B*35:

Cultures were harvested and bispecific antibodies were purified from the supernatants using protein A, Kappa-select, or IMAC (GE healthcare) based chromatography methods. If necessary, bispecific antibodies or controls were polished by SEC or mixed-mode (CHT, BIO-RAD) chromatography. Molecules were formulated in PBS by dialysis or desalting chromatography. Molecules were evaluated to confirm high monomer purity (>95%) and low endotoxin (<1 EU/mg) prior to subsequent testing.

For clarity, the nomenclature of the generated and tested bispecific antibodies recites for Formats #2-#6: as shown in FIG. 76 of International Application No. PCT/US2020/15736, which is hereby incorporated by reference in its entirety; or for format #1 (BITE®): as shown in International Application No. PCT/US2020/15736, which is hereby incorporated by reference in its entirety. Exemplary nomenclatures are shown in FIGS. 77A-C of International Application No. PCT/US2020/15736, which is hereby incorporated by reference in its entirety. For instance, the bispecific designated "1-G2 (1H11)-OKT3" is format #1 (BITE®): N-term scFv=G2 clone 1H11, C-term scFv=CD3 binder OKT3. For instance, the bispecific designated "3-G2 (1H11)-OKT3" is format #3 (scFv/Fab): scFv=G2 (1H11), Fab=OKT3. For yet other instance, the bispecific designated "4-G2 (1H11)-OKT3" is format #4 (scFv/scFv-Fab): scFv=G2 (1H11), Fab=OKT3.

A list of exemplary bispecific antibodies created using the methods described above is listed in the following table.

TABLE 19

Exemplary bispecific antibodies

| Format # | scFv (N-term) | scFv (C-term) | scFv | Fab |
|---|---|---|---|---|
| 1. BiTE® | G2(1H11) | OKT3 | | |
| 1. BiTE® | G7(2E09) | OKT3 | | |
| 1. BiTE® | G5(7A05) | OKT3 | | |
| 1. BiTE® | G8(2C10) | OKT3 | | |
| 1. BiTE® | G2(1H11) | foralumab | | |
| 1. BiTE® | G5(7A05) | foralumab | | |
| 1. BiTE® | G7(2E09) | foralumab | | |
| 1. BiTE® | G8(2C10) | foralumab | | |
| 3. scFv/Fab | | | OKT3 | G2(1H11) |
| 3. scFv/Fab | | | G2(1H11) | OKT3 |

73

TABLE 19-continued

| | Exemplary bispecific antibodies | | | |
|---|---|---|---|---|
| Format # | scFv (N-term) | scFv (C-term) | scFv | Fab |
| 3. scFv/Fab | | | G5(7A05) | OKT3 |
| 3. scFv/Fab | | | G7(2E09) | OKT3 |
| 3. scFv/Fab | | | G8(2C10) | OKT3 |
| 3. scFv/Fab | | | G2(1H11) | foralumab |
| 3. scFv/Fab | | | G5(7A05) | foralumab |
| 3. scFv/Fab | | | G7(2E09) | foralumab |
| 3. scFv/Fab | | | G8(2C10) | foralumab |
| 4. scFv/scFv-Fab | | | G2(1H11) | OKT3 |
| 4. scFv/scFv-Fab | | | G5(7A05) | OKT3 |
| 4. scFv/scFv-Fab | | | G7(2E09) | OKT3 |
| 4. scFv/scFv-Fab | | | G8(2C10) | OKT3 |
| 4. scFv/scFv-Fab | | | G2(1H11) | foralumab |
| 4. scFv/scFv-Fab | | | G5(7A05) | foralumab |
| 4. scFv/scFv-Fab | | | G7(2E09) | foralumab |
| 4. scFv/scFv-Fab | | | G8(2C10) | foralumab |
| 5. Fc/scFv-Fab | | | G2(1H11) | OKT3 |
| 5. Fc/scFv-Fab | | | G5(7A05) | OKT3 |
| 6. scFv-Fab/scFv-Fab | | | G2(1H11) | OKT3 |
| 6. scFv-Fab/scFv-Fab | | | G5(7A05) | OKT3 |
| 2. Fab-scFv/Fab-scFv | | | G2(1H11) | OKT3 |
| 2. Fab-scFv/Fab-scFv | | | G5(7A05) | OKT3 |

Amino Acid and nucleotide sequences of exemplary bispecific molecules generated are provided in the Sequences section of International Application No. PCT/US2020/15736, which is hereby incorporated by reference in its entirety.

Example 11: Generation and Characterization of Additional Antibodies

Clones 5G06, 5D10, and 9D04 were modified either to remove a glycosylation site or germlined the framework. The newly modified antibodies were as follows:

5G06NT: altered glycosylation site at residue 69 N to T at HC FR3 as compared to 5G06 parent (N69T mutation).

5D10YF: changed residue 27 Y to F (germline aa) as compared to parent 5D10 (Y27F mutation).

9D04YF: changed residue 27 Y to F (germline aa) as compared to parent 9D04 (Y27F mutation).

In addition, the phage display panning results from Example 2 were sequenced with next generation sequencing (NGS). TG1 at an OD 600 of 0.4 were infected with the final eluted phage, grown on agar plates and incubated overnight at 30° C. Bacteria was harvested by scraping from agar plates with 10 ml LB medium and used for phagemid DNA extraction using the NucleoBond Xtra Midi kit. (MACHE-REY-NAGEL).

The phagemid DNA was used as a template for NGS sample preparation, running PCR amplification of the VH and VL of the selected pools with the following primers:

74

```
Heavy chain forward primer
                              (SEQ ID NO: 64)
    5'-CAGCTGTGCCGCCAGCGGC-3'

Heavy chain reverse primer
                              (SEQ ID NO: 65)
    5'-GTCACGGTGGTTCCCTTGC-3'

Light chain forward primer
                              (SEQ ID NO: 66)
    5'-TAGGGTGACCATAACCTGC-3'

Light chain reverse primer
                              (SEQ ID NO: 67)
    5'-CCTTAGTTCCAGGGCCGAA-3'
```

PCR products were gel purified, quantified, and sent to Genewiz for sequencing using the Amplicon-EZ service. For the bioinformatic analysis, all paired-end sequence reads derived from the MiSeq run were paired-end, merged with the reads, and annotated in the CDRs using the Generous Biologics program. The heavy and light chain CDR amino acid sequences were aligned, respectively. NGS clones were identified based on their frequency of occurrence in the selections.

Two additional antibodies, NGS-18 and NGS-22 were identified based on frequency of occurrence in the selections. NGS-18 has the same sequence as 5A03 with a single Y27F mutation. NGS-22 has the same sequence as 5D07 with a single with a single Y27F mutation. VH and VL sequences of the newly engineered or sequenced antibodies are provided in Table 6. VH and VL nucleotide sequences are provided in Table 8.

The newly engineered and identified antibodies were engineering into a bispecific Format 41, which forms a diabody (FIG. 5), with an anti-CD3 binding domain. The newly generated bispecific antibodies were characterized for cell binding to A375 cells expressing ~300,000 copies of the pHLA 10 mer, cell binding to CD3 on CD3+ or CD3-Jurkat cells, and cytotoxicity on A375 FoxE1 cells expressing ~1,000 copies of the pHLA 10 mer as previously described in Examples 5 and 9.

Figures 9A, 9B:
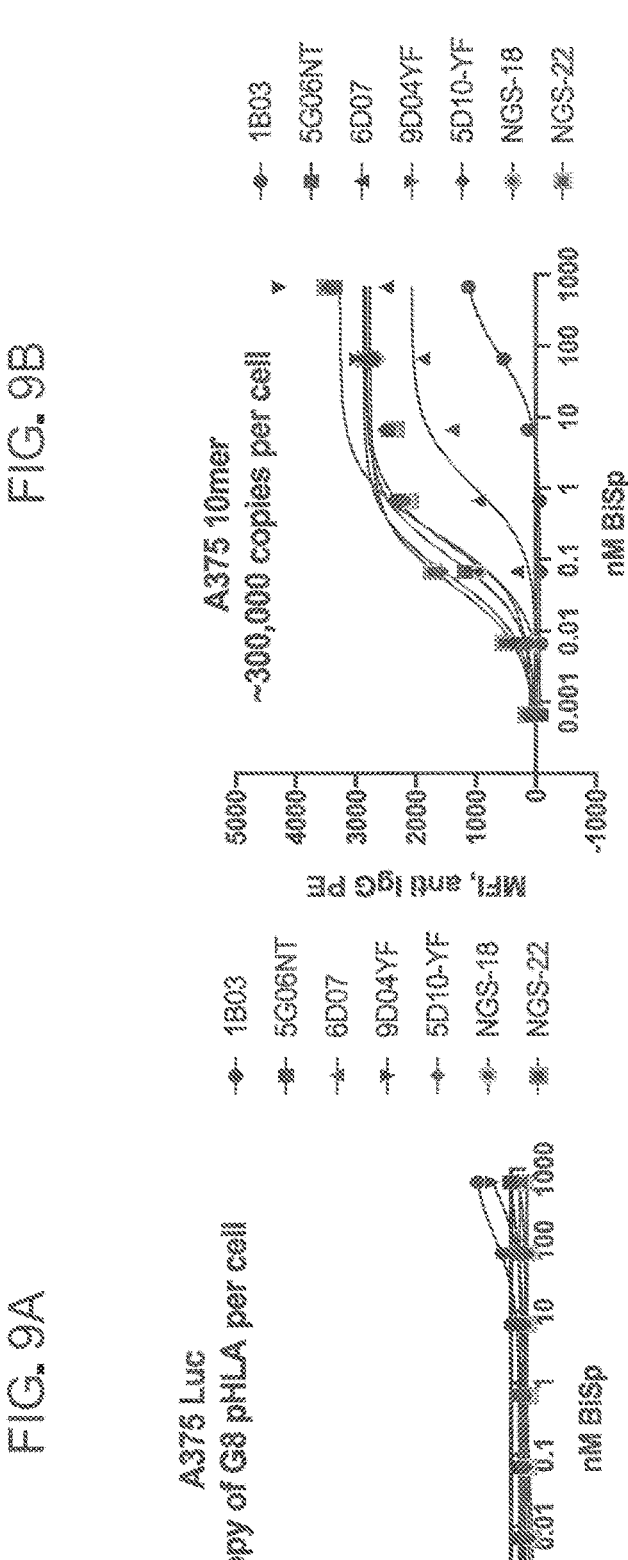
FIG. 9A shows Format 41 diabody antibody cell binding on A375 control cells.
FIG. 9B shows Format 41 diabody antibody cell binding on target-expressing cells.

All newly engineered or sequenced antibodies bound to A375 cells expressing ~300,000 copies of the target pHLA per cell. Minimal or no binding to control cells was observed. Cell binding results are shown in Table 20 and FIGS. 9A and 9B.

TABLE 20

| Ranking | NGS-22 | 5D10YF | 5G06NT | NGS-18 | 9D04YF | 6D07 | 1B03 |
|---|---|---|---|---|---|---|---|
| EC 50 (nM) | 0.04 | 0.06 | 0.11 | 0.15 | 0.24 | 1.1 | 72.8 |

Figures 10A, 10B:
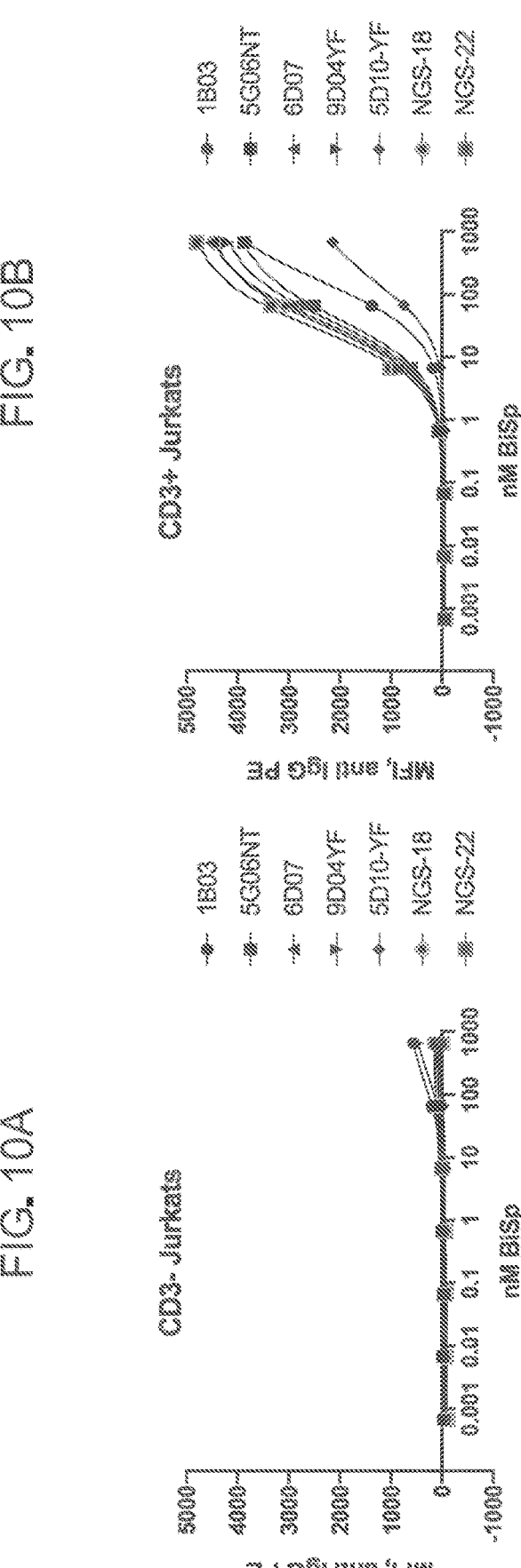
FIG. 10A shows Format 41 diabody antibody cell binding on CD3-Jurkat control cells.
FIG. 10B shows Format 41 diabody antibody cell binding on CD3+ Jurkat cells.

The newly engineered or sequenced antibodies also bound to CD3+ on CD3+ Jurkat cells. Minimal or no binding to CD3− control cells was observed. CD3 binding results are shown in Table 21 and FIGS. 10A and 10B.

TABLE 21

| Ranking | NGS-22 | NGS-18 | 6D07 | 9D04YF | 5G06NT | 5D10YF | 1B03 |
|---|---|---|---|---|---|---|---|
| EC 50 (nM) | 28.3 | 31.1 | 36.9 | 38.1 | 41.0 | 160.2 | 160.7 |

The newly engineered or sequenced antibodies induced cytotoxicity of A375 FoxE1 cells expressing ~1000 copies of the target pHLA per cell. Minimal or no non-specific killing of A375 luc control cells was observed. Cytotoxicity results are shown in Table 22 (for cytotoxicity of A375 FoxE1 cells) and FIGS. 11A and 11B. Clones 5D10YF and 9D04YF showed the highest cytotoxicity against A375 FoxE1 cells.

TABLE 22

| Ranking | 5D10YF | 9D04YF | NGS-18 | 5G06NT | NGS-22 | 6D07 | 1B03 |
|---|---|---|---|---|---|---|---|
| EC 50 (nM) | 0.008 | 0.01 | 0.07 | 0.08 | 0.2 | 5.7 | NA |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

SEQUENCES

TABLE 6

| | | VH and VL sequences of scFv hits that bind target G8, numbered according to the Kabat numbering scheme | |
|---|---|---|---|
| Target group | Clone name | $V_H$ | $V_L$ |
| G8 | 05A03 | EVQLLESGGGLVQPGGSLRLSCAA SGYTFSDYYMSWVRQAPGKGLEW VSGINWPGGSTGYADSVKGRFTISR DNSKNTLYLQMNSLRAEDTAVYY CARVEQGYDIYYYYYMDVWGKG TTVTVSS (SEQ ID NO: 1) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 05A08 | EVQLLESGGGLVQPGGSLRLSCAA SGYTFSDYYMSWVRQAPGKGLEW VGNINWNGGSTLYADSVKGRFTIS RDNSKNTLYLQMNSLRAEDTAVY YCARVEQGYDNYYYYYMDVWGK GTTVTVSS (SEQ ID NO: 3) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 05C04 | EVQLLESGGGLVQPGGSLRLSCAA SGYTFSDYYMSWVRQAPGKGLEW VSGINWPGGYTGYADSVKGRFTIS RDNSKNTLYLQMNSLRAEDTAVY YCARVEQGYDIYYYYYMDVWGK GTTVTVSS (SEQ ID NO: 4) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 05D07 | EVQLLESGGGLVQPGGSLRLSCAA SGYTFSDYYMSWVRQAPGKGLEW VSGINWYSGSTGYADSVKGRFTISR DNSKNTLYLQMNSLRAEDTAVYY CARVEQGYDIYYYYYMDVWGKG TTVTVSS (SEQ ID NO: 5) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 05D10 | EVQLLESGGGLVQPGGSLRLSCAA SGYTFSDYYMSWVRQAPGKGLEW VSGINWPGSSTGYADSVKGRFTISR DNSKNTLYLQMNSLRAEDTAVYY CARVEQGYDIYYYYYMDVWGKG TTVTVSS (SEQ ID NO: 6) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 05G06 | EVQLLESGGGLVQPGGSLRLSCAA SGFTFSDYYMSWVRQAPGKGLEW VSGINWPGGSTGYADSVKGRFNIS RDNSKNTLYLQMNSLRAEDTAVY YCARVEQGYDIYYFYYMDVWGK GTTVTVSS (SEQ ID NO: 7) | DIQMTQSPSSLSASVGDRVTITCRA SQSISSYLNWYQQKPGKAPKLLIYK ASSLESGVPSRFSGSGSGTDFTLTIS SLQPEDFATYYCQQSYSAPYTFGP GTKVDIK (SEQ ID NO: 2) |
| G8 | 0509 | EVQLLESGGGLVQPGGSLRLSCAA SGFTFSDYYMSWVRQAPGKGLEW VGGINWPGGSTDYADSVKGRFTIS RDNSKNTLYLQMNSLRAEDTAVY YCARVEQGYDIYYYYYMDVWGK GTTVTVSS (SEQ ID NO: 8) | DIQMTQSPSSLSASVGDRVTITCRA SQSISSYLNWYQQKPGKAPKLLIYK ASSLESGVPSRFSGSGSGTDFTLTIS SLQPEDFATYYCQQSYSAPYTFGP GTKVDIK (SEQ ID NO: 2) |
| G8 | 06D07 | EVQLLESGGGLVQPGGSLRLSCAA SGFTFSDYYMSWVRQAPGKGLEW VSGINWNGGSTGYADSVKGRFTIS RDNSKNTLYLQMNSLRDEDTAVY YCARVEQGYDIYYYYYMDVWGK GTTVTVSS (SEQ ID NO: 9) | DIQMTQSPSSLSASVGDRVTITCRA SQSIHSYLNWYQQKPGKAPKLLIY KASTPYSGVPSRFSGSGSGTDFTLTI SSLQPEDFATYYCQQSYSYPHNFGP GTKVDIK (SEQ ID NO: 10) |

TABLE 6-continued

| | | | |
|---|---|---|---|
| VH and VL sequences of scFv hits that bind target G8, numbered according to the Kabat numbering scheme | | | |

| Target group | Clone name | V$_H$ | V$_L$ |
|---|---|---|---|
| G8 | 09D01 | EVQLLESGGGLVQPGGSLRLSCAA SGFTFSDYYMSWVRQAPGKGLEW VSGINWHHGSTGYADSVKGRFTIS RDNSKNTLYLQMNSLRAEDTAVY YCARVEQGYDIYYYYYMDVWGK GTTVTVSS (SEQ ID NO: 11) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 09D04 | EVQLLESGGGLVQPGGSLRLSCAA SGYTFSDYYMSWVRQAPGKGLEW VSGINWPGYSTGYADSVKGRFTISR DNSKNTLYLQMNSLRAEDTAVYY CARVEQGYDNYYYYYMDVWGKG TTVTVSS (SEQ ID NO: 12) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 09D06 | EVQLLESGGGLVQPGGSLRLSCAA SGFTFSDYYMSWVRQAPGKGLEW VSGINWPGSSTGYADSVKGRFTISR DNSKNTLYLQMNSLRAEDTAVYY CARVRQGYDYYYYYYMDVWGKG TTVTVSS (SEQ ID NO: 13) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 09G01 | EVQLLESGGGLVQPGGSLRLSCAA SGFTFSDYYMSWVRQAPGKGLEW VSVINWPGSSTGYADSVKGRFTISR DNSKNTLYLQMNSLRAEDTAVYY CARVEQGYDIYYYYYMDVWGKG TTVTVSS (SEQ ID NO: 14) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | 5D10YF | EVQLLESGGGLVQPGGSLRLSC AASGFTFSDYYMSWVRQAPGK GLEWVSGINWPGSSTGYADSVK GRFTISRDNSKNTLYLQMNSLR AEDTAVYYCARVEQGYDIYYY YYMDVWGKGTTVTVSS (SEQ ID NO: 37) | DIQMTQSPSSLSASVGDRVTITC RASQSISSYLNWYQQKPGKAPK LLIYKASSLESGVPSRFSGSGSGT DFTLTISSLQPEDFATYYCQQSY SAPYTFGPGTKVDIK (SEQ ID NO: 2) |
| G8 | 5G06NT | EVQLLESGGGLVQPGGSLRLSCAA SGFTFSDYYMSWVRQAPGKGLEW VSGINWPGGSTGYADSVKGRFTISR DNSKNTLYLQMNSLRAEDTAVYY CARVEQGYDIYYFYYMDVWGKGT TVTVSS (SEQ ID NO: 38) | DIQMTQSPSSLSASVGDRVTITCRA SQSISSYLNWYQQKPGKAPKLLIYK ASSLESGVPSRFSGSGSGTDFTLTIS SLQPEDFATYYCQQSYSAPYTFGP GTKVDIK (SEQ ID NO: 2) |
| G8 | 9D04YF | EVQLLESGGGLVQPGGSLRLSCAA SGFTFSDYYMSWVRQAPGKGLEW VSGINWPGYSTGYADSVKGRFTISR DNSKNTLYLQMNSLRAEDTAVYY CARVEQGYDNYYYYYMDVWGKG TTVTVSS (SEQ ID NO: 39) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |
| G8 | NGS-18 | EVQLLESGGGLVQPGGSLRLSCAA SGFTFSDYYMSWVRQAPGKGLEW VSGINWPGGSTGYADSVKGRFTISR DNSKNTLYLQMNSLRAEDTAVYY CARVEQGYDIYYYYYMDVWGKG TTVTVSS (SEQ ID NO: 40) | DIQMTQSPSSLSASVGDRVTITC RASQSISSYLNWYQQKPGKAPK LLIYKASSLESGVPSRFSGSGSGT DFTLTISSLOPEDFATYYCQQSY SAPYTFGPGTKVDIK (SEQ ID NO: 2) |
| G8 | NGS-22 | EVQLLESGGGLVQPGGSLRLSCAA SGFTFSDYYMSWVRQAPGKGLEW VSGINWYSGSTGYADSVKGRFTISR DNSKNTLYLQMNSLRAEDTAVYY CARVEQGYDIYYYYYMDVWGKG TTVTVSS (SEQ ID NO: 41) | DIQMTQSPSSLSASVGDRVTITCRA SQSISSYLNWYQQKPGKAPKLLIYK ASSLESGVPSRFSGSGSGTDFTLTIS SLOPEDFATYYCQQSYSAPYTFGP GTKVDIK (SEQ ID NO: 2) |

TABLE 31

VH and VL sequences of scFv hits that bind target G8, numbered according to the Kabat numbering scheme

| Target group | Clone name | V_H | V_L |
|---|---|---|---|
| G8 | Parent A | EVQLLESGGGLVQPGGSLRLSCAASGFTFSDYYMSWVRQAPGKGLEWVSGINWNGGSTGYADSVKGRFTISRDNSKNTLYLQMNSLRAEDTAVYYCARVEQGYDIYYYYYMDVWGKGTTVTVSS (SEQ ID NO: 15) | DIQMTQSPSSLSASVGDRVTITCRASQSISSYLNWYQQKPGKAPKLLIYKASSLESGVPSRFSGSGSGTDFTLTISSLQPEDFATYYCQQSYSAPYTFGPGTKVDIK (SEQ ID NO: 2) |

TABLE 7

CDR sequences of identified scFvs to G8, numbered according to the Kabat numbering scheme

| Clone name | HCDR1 | HCDR2 | HCDR3 | LCDR1 | LCDR2 | LCDR3 |
|---|---|---|---|---|---|---|
| 05D07 | DYYMS (SEQ ID NO: 16) | GINWYSGSTYADSVKG (SEQ ID NO: 17) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 09G01 | DYYMS (SEQ ID NO: 16) | VINWPGSSTGYADSVKG (SEQ ID NO: 18) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 05G06 | DYYMS (SEQ ID NO: 16) | GINWPGGSTGYADSVKG (SEQ ID NO: 19) | VEQGYDIYYFYYMDV (SEQ ID NO: 34) | RASQSISSYLN (SEQ ID NO: 28) | KASSLES (SEQ ID NO: 30) | QQSYSAPYT (SEQ ID NO: 32) |
| 09D01 | DYYMS (SEQ ID NO: 16) | GINWHHGSTGYADSVKG (SEQ ID NO: 20) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 05G09 | DYYMS (SEQ ID NO: 16) | GINWPGGSTDYADSVKG (SEQ ID NO: 21) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 09D06 | DYYMS (SEQ ID NO: 16) | GINWPGSSTGYADSVKG (SEQ ID NO: 22) | VRQGYDYYYYYMDV (SEQ ID NO: 35) | RASQSISSYLN (SEQ ID NO: 28) | KASSLES (SEQ ID NO: 30) | QQSYSAPYT (SEQ ID NO: 32) |
| 05A08 | DYYMS (SEQ ID NO: 16) | NINWNGGSTLYADSVKG (SEQ ID NO: 23) | VEQGYDNYYYYMDV (SEQ ID NO: 36) | RASQSISSYLN (SEQ ID NO: 28) | KASSLES (SEQ ID NO: 30) | QQSYSAPYT (SEQ ID NO: 32) |
| 05A03 | DYYMS (SEQ ID NO: 16) | GINWPGGSTGYADSVKG (SEQ ID NO: 19) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 05C04 | DYYMS (SEQ ID NO: 16) | GINWPGGYTGYADSVKG (SEQ ID NO: 24) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 05D10 | DYYMS (SEQ ID NO: 16) | GINWPGSSTGYADSVKG (SEQ ID NO: 22) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 09D04 | DYYMS (SEQ ID NO: 16) | GINWPGYSTGYADSVKG (SEQ ID NO: 25) | VEQGYDNYYYYMDV (SEQ ID NO: 36) | RASQSISSYLN (SEQ ID NO: 28) | KASSLES (SEQ ID NO: 30) | QQSYSAPYT (SEQ ID NO: 32) |
| 06D07 | DYYMS (SEQ ID NO: 16) | GINWNGGSTGYADSVKG (SEQ ID NO: 26) | VEQGYDIYYYYMDV (SEQ ID NO: 27) | RASQSIHSYLN (SEQ ID NO: 29) | KASTPYS (SEQ ID NO: 31) | QQSYSYPHN (SEQ ID NO: 33) |
| 5D10YF | DYYMS (SEQ ID NO: 16) | GINWPGSSTGYADSVKG (SEQ ID NO: 22) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| 9D04YF | DYYMS (SEQ ID NO: 16) | GINWPGYSTGYADSVKG (SEQ ID NO: 25) | VEQGYDNYYYYMDV (SEQ ID NO: 36) | RASQSISSYLN (SEQ ID NO: 28) | KASSLES (SEQ ID NO: 30) | QQSYSAPYT (SEQ ID NO: 32) |
| 5G06YF | DYYMS (SEQ ID NO: 16) | GINWPGGSTGYADSVKG (SEQ ID NO: 19) | VEQGYDIYYFYYMDV (SEQ ID NO: 34) | RASQSISSYLN (SEQ ID NO: 28) | KASSLES (SEQ ID NO: 30) | QQSYSAPYT (SEQ ID NO: 32) |
| NGS-18 | DYYMS (SEQ ID NO: 16) | GINWPGGSTGYADSVKG (SEQ ID NO: 19) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |
| NGS-22 | DYYMS (SEQ ID NO: 16) | GINWYSGSTGYADSVKG (SEQ ID NO: 17) | VEQGYDIYYYYMDV (SEQ ID NO: 27) | RASQSISSYLN (SEQ ID NO: 28) | KASSLES (SEQ ID NO: 30) | QQSYSAPYT (SEQ ID NO: 32) |

TABLE 32

CDR sequences of identified scFvs
to G8, numbering scheme
numbered according to the Kabat

| Clone name | HCDR1 | HCDR2 | HCDR3 | LCDR1 | LCDR2 | LCDR3 |
|---|---|---|---|---|---|---|
| Parent A | DYYMS (SEQ ID | GINWNGG STGYADS VKG | VEQGYDIY YYYYMDV (SEQ ID | RASQSI SSYLN (SEQ | KASSLQQSYS ES APYT (SEQ (SEQ |  |

TABLE 32-continued

CDR sequences of identified scFvs
to G8, numbering scheme
numbered according to the Kabat

| Clone name | HCDR1 | HCDR2 | HCDR3 | LCDR1 | LCDR2 | LCDR3 |
|---|---|---|---|---|---|---|
|  | NO: 16) | (SEQ ID NO: 26) | NO: 27) | ID NO: 28) | ID NO: 30) | ID NO: 32) |

TABLE 8

Exemplary VH and VL nucleotide sequences for the affinity matured
clones (hits) and Parent A clone:

```
>05A03_VH (SEQ ID NO: 68)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGAGCGGCATCAACTGGCCGG
GCGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC

>05A03_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTaagGTGGACATCAAG >05A08_VH (SEQ ID NO: 70)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGGGTAATATCAACTGGAACG
GCGGGAGCACCTTGTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACAATTACTATTACTA
CTACATGGACGTGTGGGGCAAGGGAACCACCGTGACCGTGAGCAGC >05A08_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCaggTTCAGCGGCAGCGGAAGCGGCACCGACTTTACCC
TGACCATCAGCTCCTTGCAGCCCGAGGACTTCGCCACCTACTACTGCCAGCAAAG
CTACTCAGCCCCCTACACCTTCGGCCCTGGAACTaagGTGGACATCAAG >05C04_VH (SEQ ID NO: 71)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGAGCGGCATCAACTGGCCGG
GCGGGTATACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC >05C04_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAggTGGACATCAAG >05D07_VH (SEQ ID NO: 72)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGAGCGGCATCAACTGGTATT
CCGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC
```

TABLE 8-continued

Exemplary VH and VL nucleotide sequences for the affinity matured
clones (hits) and Parent A clone:

>05D07_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAgGTGGACATCAAG

>05D10_VH (SEQ ID NO: 73)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGAGCGGCATCAACTGGCCGG
GCTCTAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC

>05D10_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTaaggTGGACATCAAG >05G06_VH (SEQ ID NO: 74)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCTG
GCGGGAGCACCGGCTACGCCGACAGCGTGAAGGGCAGGTTCAACATCAGCAGG
GACAACAGCAAGAACACCCTGTACCTGCAGATGAACAGCCTGAGGGCCGAGGAC
ACCGCCGTGTACTACTGCGCCAGGGTGGAGCAGGGCTACGACATATACTATTTCT
ACTACATGGACGTGTGGGGCAAGGGAACCACCGTGACCGTGAGCAGC >05G06_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTaaggTGGACATCAAG >0509_VH (SEQ ID NO: 75)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGGGAGGCATCAACTGGCCG
GGCGGGAGCACCGACTACGCCGACAGCGTGAAGGGCAGGTTCACCATCAGCAGG
GACAACAGCAAGAACACCCTGTACCTGCAGATGAACAGCCTGAGGGCCGAGGAC
ACCGCCGTGTACTACTGCGCCAGGGTGGAGCAGGGCTACGACATATACTATTACT
ACTACATGGACGTGTGGGGCAAGGGAACCACCGTGACCGTGAGCAGC >0509_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTaaggtggacatcaag >06D07_VH (SEQ ID NO: 76)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGAAC
GGCGGGAGCACCGGCTACGCCGACAGCGTGAAGGGCAGGTTCACCATCAGCAGG
GACAACAGCAAGAACACCCTGTACCTGCAGATGAACAGCCTGAGGGACGAGGA
CACCGCCGTGTACTACTGCGCCAGGGTGGAGCAGGGCTACGACATATACTATTA
CTACTACATGGACGTGTGGGGCAAGGGAACCACCGTGACCGTGAGCAGC >06D07_VL (SEQ ID NO: 77)
GACATCCAGATGACCCAGAGCCCCAGCAGCCTGAGCGCCAGCGTGGGCGATAGG
GTGACCATAACCTGCCGAGCCAGCCAGAGCATCCACAGCTACCTGAACTGGTAT
CAACAGAAGCCCGGCAAGGCCCCCAAGCTCCTGATCTACAAGGCCAGCACTCCC
TACAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCATACCCCCATAATTTCGGCCCTGGAACTaaggtGGACATCAAG TABLE 8-continued Exemplary VH and VL nucleotide sequences for the affinity matured
clones (hits) and Parent A clone:

>09D01_VH (SEQ ID NO: 78)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCATC
ATGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC

>09D01_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTaaggTGGACATCAAG >09D04_VH (SEQ ID NO: 79)
GAGGTTCAGCTCCTGGAGAGCGGCGGAGGTCTGGTGCAGCCGGGTGGCTCACTG
AGGCTCAGCTGTGCCGCCAGCGGCTACACCTTCAGCGATTATTACATGAGCTGGG
TGCGACAGGCCCCAGGAAAAGGCCTGGAGTGGGTGAGCGGCATCAACTGGCCAG
GCTATAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACAATTACTATTACTA
CTACATGGACGTGTGGGGCAAGGGAACCACCGTGACCGTGAGCAGC >09D04_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >09D06_VH (SEQ ID NO: 80)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCGG
GCTCTAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGCGGCAGGGCTACGACTATTACTATTACTA
CTACATGGACGTGTGGGGCAAGGGAACCACCGTGACCGTGAGCAGC >09D06_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAgGTGGACATCAAG >09G01_VH (SEQ ID NO: 81)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGTGATCAACTGGCCGG
GCTCTAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC >09G01_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >Parent A (Reference)_VH (SEQ ID NO: 82)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGAAC
GGCGGGAGCACCGGCTACGCCGACAGCGTGAAGGGCAGGTTCACCATCAGCAGG
GACAACAGCAAGAACACCCTGTACCTGCAGATGAACAGCCTGAGGGCCGAGGAC
ACCGCCGTGTACTACTGCGCCAGGGTGGAGCAGGGCTACGACATATACTATTACT
ACTACATGGACGTGTGGGGCAAGGGAACCACCGTGACCGTGAGCAGC TABLE 8-continued Exemplary VH and VL nucleotide sequences for the affinity matured
clones (hits) and Parent A clone:

>Parent A (Reference)_VL (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >5D10YF_HC (SEQ ID NO: 83)
GAGGTTCAGCTCCTGGAGAGCGGCGGAGGTCTCGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCGG
GCTCTAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC >5D10YF_LC (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >5G06NT_HC (SEQ ID NO: 84)
GAGGTTCAGCTCCTGGAGAGCGGCGGAGGTCTCGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCTG
GCGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTTCTA
CTACATGGACGTGTGGGGCAAGGGAACCACCGTGACCGTGAGCAGC >5G06NT_LC (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >9D04YF_HC (SEQ ID NO: 85)
GAGGTTCAGCTCCTGGAGAGCGGCGGAGGTCTCGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCAG
GCTATAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACAATTACTATTACTA
CTACATGGACGTGTGGGGCAAGGGAACCACCGTGACCGTGAGCAGC >9D04YF_LC (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG >NGS-18_HC (SEQ ID NO: 86)
GAGGTTCAGCTCCTGGAGAGCGGCGGAGGTCTCGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGCCAG
GCGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC >NGS-18_LC (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG TABLE 8-continued Exemplary VH and VL nucleotide sequences for the affinity matured
clones (hits) and Parent A clone:

>NGS-22_HC (SEQ ID NO: 87)
GAGGTTCAGCTCCTGGAGAGCGGCGGAGGTCTGGTGCAGCCGGGTGGCTCACTG
AGGCTCAGCTGTGCCGCCAGCGGCTTCACCTTCAGCGATTATTACATGAGCTGGG
TGCGACAGGCCCCAGGAAAAGGCCTGGAGTGGGTGAGCGGCATCAACTGGTATT
CCGGGAGCACCGGCTACGCCGACAGCGTGAAGGGCAGGTTCACCATCAGCAGGG
ACAACAGCAAGAACACCCTGTACCTGCAGATGAACAGCCTGAGGGCCGAGGACA
CCGCCGTGTACTACTGCGCCAGGGTGGAGCAGGGCTACGACATATACTATTACTA
CTACATGGACGTGTGGGGCAAGGGAACCACCGTGACCGTGAGCAGC

>NGS-22_LC (SEQ ID NO: 69)
GACATCCAGATGACCCAGAGCCCCAGCAGCCTGAGCGCCAGCGTGGGCGATAGG
GTGACCATAACCTGCCGAGCCAGCCAGAGCATCAGCAGCTACCTGAACTGGTAT
CAACAGAAGCCCGGCAAGGCCCCCAAGCTCCTGATCTACAAGGCCAGCAGTCTG
GAGAGCGGCGTGCCCTCCAGGTTCAGCGGCAGCGGAAGCGGCACCGACTTTACC
CTGACCATCAGCTCCTTGCAGCCCGAGGACTTCGCCACCTACTACTGCCAGCAAA
GCTACTCAGCCCCCTACACCTTCGGCCCTGGAACTAAGGTGGACATCAAG

The invention claimed is:

1. An isolated antigen binding protein (ABP) comprising a first scFv and a second scFv which each specifically bind a target antigen, a Fab that specifically binds CD3, and an Fc domain, wherein the ABP comprises:
    (a) a first polypeptide comprising, in an N→C direction, the first scFv and a —CH2-CH3;
    (b) a second polypeptide comprising, in an N→C direction, the second scFv, a VH domain of the Fab, a CH1 domain of the Fab, and a —CH2-CH3; and
    (c) a third polypeptide comprising, in an N→C direction, a VL domain of the Fab and a CL domain of the Fab; wherein:
    the target antigen is a human leukocyte antigen (HLA)-PEPTIDE target comprising HLA subtype A*02:01 and a peptide comprising the sequence AIFPGAVPAA (SEQ ID NO: 42); and
    the first scFv and the second scFv each comprise a variable heavy chain (VH) sequence comprising the sequence set forth in SEQ ID NO:37 or SEQ ID NO:39, and a variable light chain (VL) sequence comprising the sequence set forth in SEQ ID NO:2.

2. The isolated ABP according to claim 1, wherein CD3 is CD3ε.

3. The isolated ABP according to claim 1, wherein the Fab that specifically binds CD3 comprises the antigen binding domain of OKT3.

4. The isolated ABP according to claim 1, wherein the Fab that specifically binds CD3 comprises the antigen binding domain of foralumab.

5. The isolated ABP according to claim 1, wherein the sequence comprising the CH2-CH3 domains of the first polypeptide is distinct from the sequence comprising the CH2-CH3 domains of the second polypeptide.

6. The isolated ABP according to claim 1, wherein the ABP comprises a diabody.

7. The isolated ABP according to claim 1, wherein the ABP comprises a first interchain linker of between 3 and 12 amino acids between the VH and VL of the first scFv and a second interchain linker of between 3 and 12 amino acids between the VH and VL of the second scFv.

8. The isolated ABP according to claim 1, wherein the ABP comprises a first interchain linker of 10 amino acids between the VH and VL of the first scFv and a second interchain linker of 10 amino acids between the VH and VL of the second scFv.

9. The isolated ABP of claim 1, wherein:
    (i) the VH and VL from the first scFv in the first polypeptide noncovalently interacts with the VL and VH from the second scFv in the second polypeptide, respectively, or
    (ii) the VL and VH from the first scFv in the first polypeptide noncovalently interacts with the VH and VL from the second scFv in the second polypeptide, respectively.

10. The isolated ABP of claim 9, wherein the noncovalent interactions consist of hydrophobic, electrostatic, and/or van der Waals interactions.

11. The isolated ABP according to claim 1, wherein:
    (i) the ABP is linked to a scaffold;
    (ii) the ABP is linked to a scaffold, wherein the scaffold comprises serum albumin; or
    (iii) the ABP is linked to a scaffold, wherein the scaffold comprises an Fc region.

12. The isolated ABP according to claim 11, wherein the Fc region is an isotype chosen from an IgG, an IgA, an IgD, an IgE, or an IgM.

13. The isolated ABP according to claim 11, wherein the Fc region is an IgG or IgA and is of a subclass chosen from IgG1, IgG2, IgG3, IgG4, IgA1, or IgA2.

14. An isolated polynucleotide or set of polynucleotides encoding: (i) the isolated ABP according to claim 1.

15. A cDNA encoding the isolated ABP according to claim 1.

16. A vector or set of vectors comprising the isolated polynucleotide or set of polynucleotides according to claim 14.

17. A host cell comprising the isolated polynucleotide or set of polynucleotides according to claim 14.

18. The host cell according to claim 17, wherein the host cell is CHO, HEK293, K-562, A375 cell, or a T cell.

19. A cell culture system comprising:
    a. a host cell according to claim 17, and
    b. a cell culture medium.

20. A method of producing an isolated antigen binding protein (ABP) comprising expressing the ABP within the host cell according to claim 17 and isolating the expressed ABP.

21. A pharmaceutical composition comprising the isolated ABP according to claim 1 and a pharmaceutically acceptable excipient.

22. A kit comprising the pharmaceutical composition according to claim 21.

23. A method of treating cancer in a subject in need thereof, comprising administering to the subject an effective amount of the isolated ABP according to claim 1.

24. The method according to claim 23, wherein the cancer is a solid tumor or a hematological tumor.

25. The method according to claim 23, wherein the cancer expresses or is predicted to express the HLA-PEPTIDE target.

26. A method of modulating an immune response in a subject in need thereof, comprising administering to the subject an effective amount of the isolated ABP of claim 1.

27. An isolated antigen binding protein (ABP) comprising a first scFv and a second scFv which each specifically bind a target antigen, a Fab that specifically binds CD3, and an Fc domain, wherein the ABP comprises:
    (a) a first polypeptide comprising, in an N→C direction, the first scFv and a —CH2-CH3;
    (b) a second polypeptide comprising, in an N→C direction, the second scFv, a VH domain of the Fab, a CH1 domain of the Fab, and a —CH2-CH3; and
    (c) a third polypeptide comprising, in an N→C direction, a VL domain of the Fab and a CL domain of the Fab;

wherein:

the target antigen is a human leukocyte antigen (HLA)-PEPTIDE target comprising HLA subtype A*02:01 and a peptide comprising the sequence AIFPGAVPAA (SEQ ID NO: 42); and the first scFv and the second scFv each comprise:

(i) a variable heavy chain (VH) sequence comprising complementarity-determining regions (CDR) H1 (CDR-H1), CDR-H2, and CDR-H3 comprising the sequences set forth in SEQ ID NOs 16, 22, and 27 respectively, and a variable light chain (VL) sequence comprising CDR-L1, CDR-L2, and CDR-L3 comprising the sequences set forth in SEQ ID NOs 28, 30, and 32, respectively; or (ii) a variable heavy chain (VH) sequence comprising complementarity-determining regions (CDR) H1 (CDR-H1), CDR-H2, and CDR-H3 comprising the sequences set forth in SEQ ID NOs 16, 25, and 36 respectively, and a variable light chain (VL) sequence comprising CDR-L1, CDR-L2, and CDR-L3 comprising the sequences set forth in SEQ ID NOs 28, 30, and 32, respectively.

* * * * *